(12) United States Patent
Hiscott

(10) Patent No.: US 9,790,509 B2
(45) Date of Patent: Oct. 17, 2017

(54) 5'-TRIPHOSPHATE OLIGORIBONUCLEOTIDES

(71) Applicant: John Hiscott, Rome (IT)

(72) Inventor: John Hiscott, Rome (IT)

(73) Assignee: Oregon Health & Science University, Portland, OR (US)

( * ) Notice: Subject to any disclaimer, the term of this patent is extended or adjusted under 35 U.S.C. 154(b) by 0 days.

(21) Appl. No.: 14/802,187

(22) Filed: Jul. 17, 2015

(65) Prior Publication Data

US 2016/0017334 A1    Jan. 21, 2016

Related U.S. Application Data

(60) Provisional application No. 62/026,473, filed on Jul. 18, 2014.

(51) Int. Cl.
| | |
|---|---|
| *C12N 15/11* | (2006.01) |
| *C12N 15/117* | (2010.01) |
| *A61K 39/39* | (2006.01) |
| *C12N 7/00* | (2006.01) |
| *A61K 39/12* | (2006.01) |
| *A61K 39/00* | (2006.01) |

(52) U.S. Cl.
CPC ............ *C12N 15/117* (2013.01); *A61K 39/12* (2013.01); *A61K 39/39* (2013.01); *C12N 7/00* (2013.01); *A61K 2039/5258* (2013.01); *A61K 2039/55561* (2013.01); *C12N 2310/531* (2013.01); *C12N 2320/31* (2013.01); *C12N 2760/16123* (2013.01); *C12N 2760/16134* (2013.01)

(58) Field of Classification Search
None
See application file for complete search history.

(56) References Cited

U.S. PATENT DOCUMENTS

| | | | |
|---|---|---|---|
| 2010/0129401 A1* | 5/2010 | Smith .................. | A61K 39/145 424/210.1 |
| 2011/0165123 A1 | 7/2011 | Hartmann et al. | |
| 2012/0288476 A1 | 11/2012 | Hartmann et al. | |
| 2014/0287023 A1 | 9/2014 | Hiscott et al. | |

OTHER PUBLICATIONS

Snove et al., Nature Methods, 2006, 3(9):689-695.*
Ge et al., RNA, 2010, 16:106-117, plus one additional page For Supplemental Table 1.*
Ge et al., PNAS, 2008, 101(23):8676-8681.*
Hornung V et al, Science 314, 994-997 (2006).
Pichlmair A et al, Science 314, 997-1001 (2006).
Kim DH et al, Nat Biotechol 22, 321-325 (2004).
Fujita T, Immunity 31, 4-5 (2009).
Schlee M and G Hartmann, Molecular Therapy 18, 1254-1262 (2010).
Kato H et al, J Exp Med 205, 1601-1610 (2008).
Baum A et al, Proc Natl Acad Sci USA 107, 16303-16308 (2010).
Rehwinkel J and Sousa CRE, Science 327, 284-286 (2010).
Rehwinkel J et al, Cell 140, 397-408 (2010).
Cui S et al, Molecular Cell 29, 169-179 (2008).
Goubau D et al, Nature 514, 372-375 (2014).
Goulet ML et al, PLoS Pathog 9, e1003298 (2013).
Olagnier D et al, J Virol 88, 4180-4194 (2014.
Schlee M et al, Immunity 31, 25-34 (2009).
Diebold SS et al, Science 303, 1529-1531 (2004).
Spurgers KB et al, Antiviral Res, 78, 26-36 (2008).
Sato S et al, Immunity 42, 123-132 (2015).
Binder M et al, J Biol Chem 286, 27278-27287 (2011).
Patel JR et al, EMBO Rep 14, 780-787 (2013).
Uzri D and Gehrke L, J Virol 83, 4174-4184 (2009).
Hwang SY et al, Nucleic Acids Res 40, 2724-2733 (2012).
Saito T et al, Nature 454, 523-527 (2008).
Schnell G et al, PLoS Pathog 8, e1002839 (2012).
Ichinohe T et al, J Virol 79, 2910-2919 (2005).
Kulkarni RR et al, J Virol 88, 13990-14001 (2014).
Martinez-Gil L et al, J Virol 87, 1290-1300 (2013).
Search Report Dated Sep. 13, 2016 for International Application No. PCT/US15/40861.

* cited by examiner

Primary Examiner — Stacy B Chen
(74) Attorney, Agent, or Firm — Lee & Hayes PLLC

(57) ABSTRACT

Disclosed herein are synthetic oligoribonucleotides that form hairpin loop structures. The oligoribonucleotides can be used in the treatment of viral infection including prophylactic treatments. The oligoribonucleotides can also be used as adjuvants.

8 Claims, 55 Drawing Sheets

| Name | Structure | Length | Minimum free energy |
|---|---|---|---|
| WT | 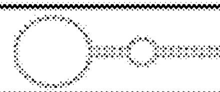 | 67 | -18.00 |
| M1 | 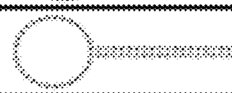 | 67 | -30.60 |
| M2 | 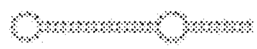 | 67 | -31.00 |
| M3 | 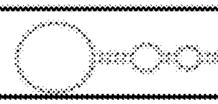 | 67 | -10.20 |
| M4 | 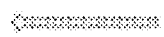 | 41 | -31.10 |
| M5 | 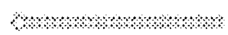 | 59 | -42.50 |
| M6 | 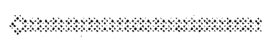 | 69 | -47.00 |
| M7 | 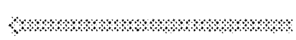 | 79 | -51.50 |
| M8 | 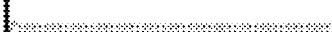 | 99 | -60.50 |
| poly (I:C) | 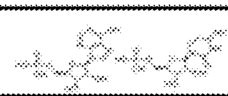 | ~300 | N/A |
| CL2 | 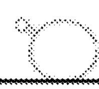 | 43 | -0.60 |
| CL9 | 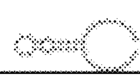 | 42 | -2.60 |

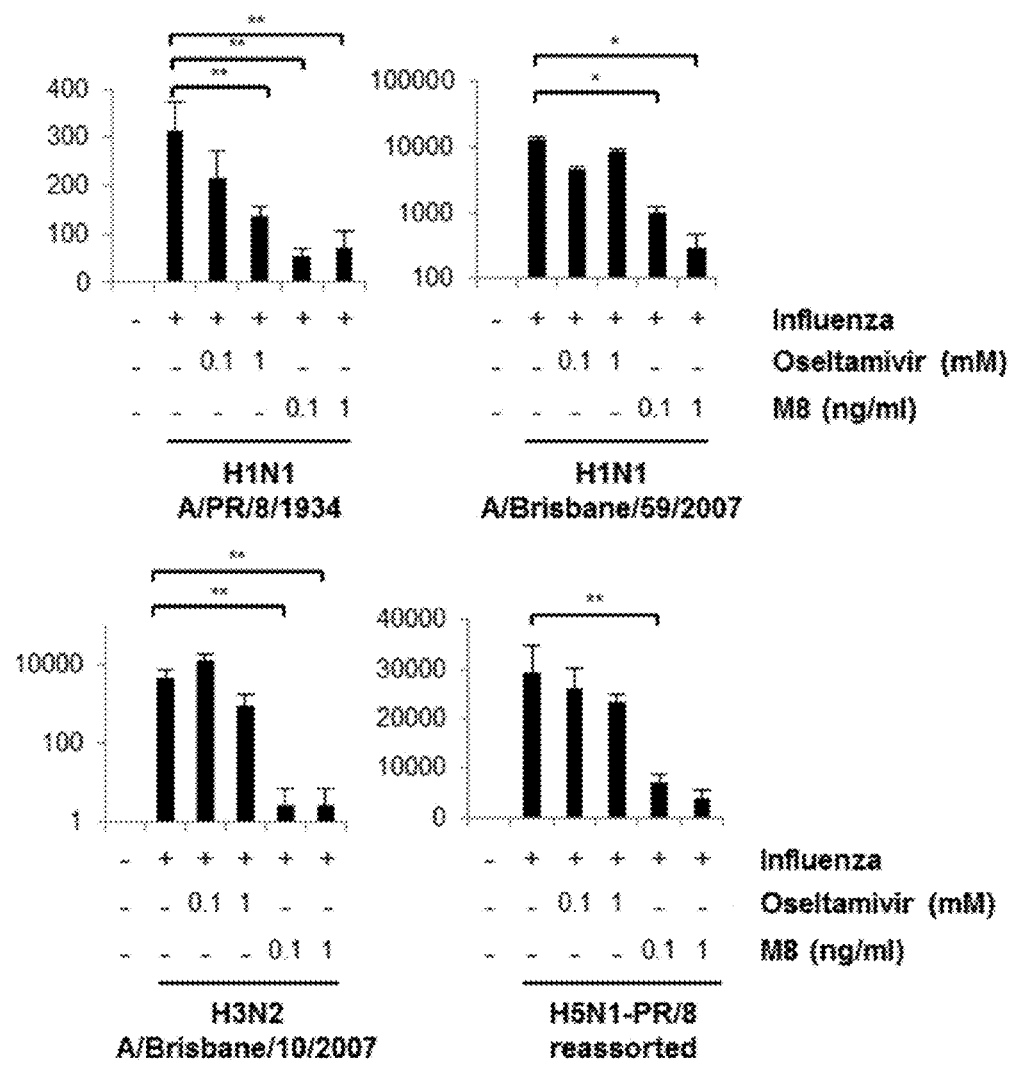

SEQUENCE LISTING

```
<160> NUMBER OF SEQ ID NOS: 127

<210> SEQ ID NO 1
<211> LENGTH: 19
<212> TYPE: RNA
<213> ORGANISM: Artificial Sequence
<220> FEATURE:
<223> OTHER INFORMATION: Oligonucleotide

<400> SEQUENCE: 1
gacgaagacc acaaaacca                                                 19

<210> SEQ ID NO 2
<211> LENGTH: 19
<212> TYPE: RNA
<213> ORGANISM: Artificial Sequence
<220> FEATURE:
<223> OTHER INFORMATION: oligonucleotide

<400> SEQUENCE: 2
ugguuuugug gucuucguc                                                 19

<210> SEQ ID NO 3
<211> LENGTH: 22
<212> TYPE: RNA
<213> ORGANISM: Artificial Sequence
<220> FEATURE:
<223> OTHER INFORMATION: oligonucleotide

<400> SEQUENCE: 3
gacgaagacc acaaaaccag au                                             22

<210> SEQ ID NO 4
<211> LENGTH: 22
<212> TYPE: RNA
<213> ORGANISM: Artificial Sequence
<220> FEATURE:
<223> OTHER INFORMATION: oligoribonucleotide
```

```
<400> SEQUENCE: 4
aucugguuuu guggucuucg uc                                              22

<210> SEQ ID NO 5
<211> LENGTH: 67
<212> TYPE: RNA
<213> ORGANISM: Artificial Sequence
<220> FEATURE:
<223> OTHER INFORMATION: oligoribonucleotide

<400> SEQUENCE: 5
gacgaagacc acaaaaccag auaaaaaaua aaauuuuaau gauaauaaug guuuguuugu     60
cuucguc                                                               67

<210> SEQ ID NO 6
<211> LENGTH: 67
<212> TYPE: RNA
<213> ORGANISM: Artificial Sequence
<220> FEATURE:
<223> OTHER INFORMATION: oligoribonucleotide

<400> SEQUENCE: 6
gacgaagacc acaaaaccag auaaaaaaua aaauuuuaau gauaauaaug guuugugguu    60
cuucguc                                                               67

<210> SEQ ID NO 7
<211> LENGTH: 67
<212> TYPE: RNA
<213> ORGANISM: Artificial Sequence
<220> FEATURE:
<223> OTHER INFORMATION: oligoribonucleotide

<400> SEQUENCE: 7
gacgaagacc acaaaaccag auaaaaaaua aaauuuuaau uuuuuaucug guuuguuugu    60
cuucguc                                                               67

<210> SEQ ID NO 8
<211> LENGTH: 67
<212> TYPE: RNA
<213> ORGANISM: Artificial Sequence
<220> FEATURE:
<223> OTHER INFORMATION: oligoribonucleotide

<400> SEQUENCE: 8
gacgaagacc acaaaaccag auaaaaaaua aaauuuuaau gauaauaaug guuuguuugu    60
cggaguc                                                               67

<210> SEQ ID NO 9
<211> LENGTH: 41
<212> TYPE: RNA
<213> ORGANISM: Artificial Sequence
<220> FEATURE:
<223> OTHER INFORMATION: oligoribonucleotide

<400> SEQUENCE: 9
gacgaagacc acaaaaccau aaugguuuug ggucuucgu c                          41

<210> SEQ ID NO 10
<211> LENGTH: 59
<212> TYPE: RNA
<213> ORGANISM: Artificial Sequence
<220> FEATURE:
<223> OTHER INFORMATION: oligoribonucleotide
```

<400> SEQUENCE: 10
gacgaagacc acaaaaccag auaaaaaaua auuuuuuauc ugguuugug gucuucguc      59

<210> SEQ ID NO 11
<211> LENGTH: 69
<212> TYPE: RNA
<213> ORGANISM: Artificial Sequence
<220> FEATURE:
<223> OTHER INFORMATION: oligoribonucleotide

<400> SEQUENCE: 11
gacgaagacc acaaaaccag auaaaaaaaa aaauaauuuu uuuuuuauc ugguuugug     60 gucuucguc                                                           69

<210> SEQ ID NO 12
<211> LENGTH: 79
<212> TYPE: RNA
<213> ORGANISM: Artificial Sequence
<220> FEATURE:
<223> OTHER INFORMATION: oligoribonucleotide

<400> SEQUENCE: 12
gacgaagacc acaaaaccag auaaaaaaaa aaaaaaaaua auuuuuuuu uuuuuuauc     60 ugguuugug gucuucguc                                                 79

<210> SEQ ID NO 13
<211> LENGTH: 99
<212> TYPE: RNA
<213> ORGANISM: Artificial Sequence
<220> FEATURE:
<223> OTHER INFORMATION: oligoribonucleotide

<400> SEQUENCE: 13
gacgaagacc acaaaaccag auaaaaaaaa aaaaaaaaaa aaaaaaaua auuuuuuuuu    60 uuuuuuuuu uuuuuuauc ugguuugug gucuucguc                             99

<210> SEQ ID NO 14
<211> LENGTH: 99
<212> TYPE: RNA
<213> ORGANISM: Artificial Sequence
<220> FEATURE:
<223> OTHER INFORMATION: oligoribonucleotide

<400> SEQUENCE: 14
gacgaagacc acaaaaccag auaauaauaa uaauaauaau aauaauaaua auuauuauua   60
uuauuauuau uauuauuauc ugguuugug gucuucguc                           99

<210> SEQ ID NO 15
<211> LENGTH: 99
<212> TYPE: RNA
<213> ORGANISM: Artificial Sequence
<220> FEATURE:
<223> OTHER INFORMATION: oligoribonucleotide

<400> SEQUENCE: 15
gcaucguaca gcugcaguua cuuaauucau ugaauaucuu augcauguac uacaugcaua    60
agauauucaa ugaauuaagu aacugcagcu guacgaugc                          99

<210> SEQ ID NO 16
<211> LENGTH: 99
<212> TYPE: RNA

```
<213> ORGANISM: Artificial Sequence
<220> FEATURE:
<223> OTHER INFORMATION: oligonucleotide

<400> SEQUENCE: 16
gacgaagacc acaaaaccag aucacacaca cacacacaca cacacacaua augugugugu      60
gugugugugu gugugugauc ugguuugug gucuucguc                             99

<210> SEQ ID NO 17
<211> LENGTH: 99
<212> TYPE: RNA
<213> ORGANISM: Artificial Sequence
<220> FEATURE:
<223> OTHER INFORMATION: oligoribonucleotide

<400> SEQUENCE: 17
gaccaaccag acaacaagag auaaaaaaaa aaaaaaaaa aaaaaaaaua auuuuuuuu       60 uuuuuuuuuu uuuuuuuauc ucuuguuguc ugguugguc                            99

<210> SEQ ID NO 18
<211> LENGTH: 89
<212> TYPE: DNA
<213> ORGANISM: Artificial Sequence
<220> FEATURE:
<223> OTHER INFORMATION: oligonucleotide

<400> SEQUENCE: 18
gacgaagaca aacaaaccat tattatcatt aaaattttat tttttatctg gttttgtggt      60
cttcgtctat agtgagtcgt attaatttc                                       89

<210> SEQ ID NO 19
<211> LENGTH: 89
<212> TYPE: DNA
<213> ORGANISM: Artificial Sequence
<220> FEATURE:
<223> OTHER INFORMATION: oligonucleotide

<400> SEQUENCE: 19
gaaattaata cgactcacta tagacgaaga ccacaaaacc agataaaaaa taaaatttta      60
atgataataa tggtttgttt gtcttcgtc                                       89

<210> SEQ ID NO 20
<211> LENGTH: 89
<212> TYPE: DNA
<213> ORGANISM: Artificial Sequence
<220> FEATURE:
<223> OTHER INFORMATION: oligonucleotide

<400> SEQUENCE: 20
gacgaagacc acaaaaccat tattatcatt aaaattttat tttttatctg gttttgtggt      60
cttcgtctat agtgagtcgt attaatttc                                       89

<210> SEQ ID NO 21
<211> LENGTH: 89
<212> TYPE: DNA
<213> ORGANISM: Artificial Sequence
<220> FEATURE:
<223> OTHER INFORMATION: oligonucleotide

<400> SEQUENCE: 21
gaaattaata cgactcacta tagacgaaga ccacaaaacc agataaaaaa taaaatttta      60
atgataataa tggttttgtg gtcttcgtc                                       89
```

<210> SEQ ID NO 22
<211> LENGTH: 89
<212> TYPE: DNA
<213> ORGANISM: Artificial Sequence
<220> FEATURE:
<223> OTHER INFORMATION: oligonucleotide

<400> SEQUENCE: 22
gacgaagaca acaaaccag ataaaaaatt aaaattttat tttttatctg gttttgtggt    60
cttcgtctat agtgagtcgt attaatttc                                    89

<210> SEQ ID NO 23
<211> LENGTH: 89
<212> TYPE: DNA
<213> ORGANISM: Artificial Sequence
<220> FEATURE:
<223> OTHER INFORMATION: oligonucleotide

<400> SEQUENCE: 23
gaaattaata cgactcacta tagacgaaga ccacaaaacc agataaaaaa taaaatttta    60 atttttatc tggtttgttt gtcttcgtc                                     89

<210> SEQ ID NO 24
<211> LENGTH: 89
<212> TYPE: DNA
<213> ORGANISM: Artificial Sequence
<220> FEATURE:
<223> OTHER INFORMATION: oligonucleotide

<400> SEQUENCE: 24
gactccgaca acaaaccat tattatcatt aaaattttat tttttatctg gttttgtggt    60
cttcgtctat agtgagtcgt attaatttc                                    89

<210> SEQ ID NO 25
<211> LENGTH: 89
<212> TYPE: DNA
<213> ORGANISM: Artificial Sequence
<220> FEATURE:
<223> OTHER INFORMATION: oligonucleotide

<400> SEQUENCE: 25
gaaattaata cgactcacta tagacgaaga ccacaaaacc agataaaaaa taaaatttta    60
atgataataa tggtttgttt gtcggagtc                                    89

<210> SEQ ID NO 26
<211> LENGTH: 63
<212> TYPE: DNA
<213> ORGANISM: Artificial Sequence
<220> FEATURE:
<223> OTHER INFORMATION: oligonucleotide

<400> SEQUENCE: 26
gacgaagacc acaaaaccat tatggttttg tggtcttcgt ctatagtgag tcgtattaat    60
ttc                                                                63

<210> SEQ ID NO 27
<211> LENGTH: 63
<212> TYPE: DNA
<213> ORGANISM: Artificial Sequence
<220> FEATURE:
<223> OTHER INFORMATION: oligonucleotide

<400> SEQUENCE: 27
gaaattaata cgactcacta tagacgaaga ccacaaaacc ataatggttt tgtggtcttc    60
gtc                                                                  63

<210> SEQ ID NO 28
<211> LENGTH: 81
<212> TYPE: DNA
<213> ORGANISM: Artificial Sequence
<220> FEATURE:
<223> OTHER INFORMATION: oligonucleotide

<400> SEQUENCE: 28
gacgaagacc acaaaaccag ataaaaaatt attttttatc tggttttgtg gtcttcgtct    60
atagtgagtc gtattaattt c                                              81

<210> SEQ ID NO 29
<211> LENGTH: 81
<212> TYPE: DNA
<213> ORGANISM: Artificial Sequence
<220> FEATURE:
<223> OTHER INFORMATION: oligonucleotide

<400> SEQUENCE: 29
gaaattaata cgactcacta tagacgaaga ccacaaaacc agataaaaaa taattttttta   60 tctggttttg tggtcttcgt c                                              81

<210> SEQ ID NO 30
<211> LENGTH: 91
<212> TYPE: DNA
<213> ORGANISM: Artificial Sequence
<220> FEATURE:
<223> OTHER INFORMATION: oligonucleotide

<400> SEQUENCE: 30
gacgaagacc acaaaaccag ataaaaaaaa aaattatttt ttttttttatc tggttttgtg   60 gtcttcgtct atagtgagtc gtattaattt c                                   91

<210> SEQ ID NO 31
<211> LENGTH: 91
<212> TYPE: DNA
<213> ORGANISM: Artificial Sequence
<220> FEATURE:
<223> OTHER INFORMATION: oligonucleotide

<400> SEQUENCE: 31
gaaattaata cgactcacta tagacgaaga ccacaaaacc agataaaaaa aaaaataatt    60
ttttttttta tctggttttg tggtcttcgt c                                   91

<210> SEQ ID NO 32
<211> LENGTH: 101
<212> TYPE: DNA
<213> ORGANISM: Artificial Sequence
<220> FEATURE:
<223> OTHER INFORMATION: oligonucleotide

<400> SEQUENCE: 32
gacgaagacc acaaaaccag ataaaaaaaa aaaaaaaatt attttttttt ttttttttatc   60 tggttttgtg gtcttcgtct atagtgagtc gtattaattt c                       101

<210> SEQ ID NO 33
<211> LENGTH: 101

```
<212> TYPE: DNA
<213> ORGANISM: Artificial Sequence
<220> FEATURE:
<223> OTHER INFORMATION: oligonucleotide

<400> SEQUENCE: 33
gaaattaata cgactcacta tagacgaaga ccacaaaacc agataaaaaa aaaaaaaaaa      60
taattttttt tttttttttta tctggttttg tggtcttcgt c                        101

<210> SEQ ID NO 34
<211> LENGTH: 101
<212> TYPE: DNA
<213> ORGANISM: Artificial Sequence
<220> FEATURE:
<223> OTHER INFORMATION: oligonucleotide

<400> SEQUENCE: 34
gaaattaata cgactcacta tagacgaaga ccacaaaacc agataaaaaa aaaaaaaaaa      60
taattttttt tttttttttta tctggttttg tggtcttcgt c                        101

<210> SEQ ID NO 35
<211> LENGTH: 121
<212> TYPE: DNA
<213> ORGANISM: Artificial Sequence
<220> FEATURE:
<223> OTHER INFORMATION: oligonucleotide

<400> SEQUENCE: 35
gaaattaata cgactcacta tagacgaaga ccacaaaacc agataaaaaa aaaaaaaaaa      60
aaaaaaaaaa taattttttt tttttttttt tttttttta tctggttttg tggtcttcgt     120
c                                                                    121

<210> SEQ ID NO 36
<211> LENGTH: 121
<212> TYPE: DNA
<213> ORGANISM: Artificial Sequence
<220> FEATURE:
<223> OTHER INFORMATION: oligonucleotide

<400> SEQUENCE: 36
gacgaagacc acaaaaccag ataataataa taataataat aataataatt attattatta     60
ttattattat tattattatc tggttttgtg gtcttcgtct atagtgagtc gtattaattt    120
c                                                                    121

<210> SEQ ID NO 37
<211> LENGTH: 121
<212> TYPE: DNA
<213> ORGANISM: Artificial Sequence
<220> FEATURE:
<223> OTHER INFORMATION: oligonucleotide

<400> SEQUENCE: 37
gaaattaata cgactcacta tagacgaaga ccacaaaacc agataataat aataataata     60
ataataataa taattattat tattattatt attattatta tctggttttg tggtcttcgt    120
c                                                                    121

<210> SEQ ID NO 38
<211> LENGTH: 121
<212> TYPE: DNA
<213> ORGANISM: Artificial Sequence
<220> FEATURE:
```

<223> OTHER INFORMATION: oligonucleotide

<400> SEQUENCE: 38

```
gcatcgtaca gctgcagtta cttaattcat tgaatatctt atgcatgtag tacatgcata    60
agatattcaa tgaattaagt aactgcagct gtacgatgct atagtgagtc gtattaattt   120
c                                                                   121
```

<210> SEQ ID NO 39
<211> LENGTH: 121
<212> TYPE: DNA
<213> ORGANISM: Artificial Sequence
<220> FEATURE:
<223> OTHER INFORMATION: oligonucleotide

<400> SEQUENCE: 39

```
gaaattaata cgactcacta gcatcgta cagctgcagt tacttaattc attgaatatc    60
ttatgcatgt actacatgca taagatattc aatgaattaa gtaactgcag ctgtacgatg   120
c                                                                   121
```

<210> SEQ ID NO 40
<211> LENGTH: 121
<212> TYPE: DNA
<213> ORGANISM: Artificial Sequence
<220> FEATURE:
<223> OTHER INFORMATION: oligonucleotide

<400> SEQUENCE: 40

```
gacgaagacc acaaaaccag atcacacaca cacacacaca cacacacatt atgtgtgtgt    60
gtgtgtgtgt gtgtgtgatc tggttttgtg gtcttcgtct atagtgagtc gtattaattt   120
c                                                                   121
```

<210> SEQ ID NO 41
<211> LENGTH: 121
<212> TYPE: DNA
<213> ORGANISM: Artificial Sequence
<220> FEATURE:
<223> OTHER INFORMATION: oligonucleotide

<400> SEQUENCE: 41

```
gaaattaata cgactcacta gacgaaga ccacaaaacc agatcacaca cacacacaca    60
cacacacaca taatgtgtgt gtgtgtgtgt gtgtgtgtga tctggttttg tggtcttcgt   120
c                                                                   121
```

<210> SEQ ID NO 42
<211> LENGTH: 121
<212> TYPE: DNA
<213> ORGANISM: Artificial Sequence
<220> FEATURE:
<223> OTHER INFORMATION: oligonucleotide

<400> SEQUENCE: 42

```
gaccaaccag acaacaagag ataaaaaaaa aaaaaaaaa aaaaaaatt attttttttt    60
tttttttttt tttttttatc tcttgttgtc tggttggtct atagtgagtc gtattaattt   120
c                                                                   121
```

<210> SEQ ID NO 43
<211> LENGTH: 121
<212> TYPE: DNA
<213> ORGANISM: Artificial Sequence
<220> FEATURE:
<223> OTHER INFORMATION: oligonucleotide

<400> SEQUENCE: 43
gaaattaata cgactcacta tagaccaacc agacaacaag agataaaaaa aaaaaaaaaa    60
aaaaaaaaaa taattttttt tttttttttt tttttttta tctcttgttg tctggttggt   120
c                                                                  121

<210> SEQ ID NO 44
<211> LENGTH: 19
<212> TYPE: DNA
<213> ORGANISM: Artificial Sequence
<220> FEATURE:
<223> OTHER INFORMATION: oligonucleotide

<400> SEQUENCE: 44
gactgggctt gtccttgct                                                19

<210> SEQ ID NO 45
<211> LENGTH: 23
<212> TYPE: DNA
<213> ORGANISM: Artificial Sequence
<220> FEATURE:
<223> OTHER INFORMATION: oligonucleotide

<400> SEQUENCE: 45
aagaagtcgt tttcctcctt tgt                                           23

<210> SEQ ID NO 46
<211> LENGTH: 20
<212> TYPE: DNA
<213> ORGANISM: Artificial Sequence
<220> FEATURE:
<223> OTHER INFORMATION: oligonucleotide

<400> SEQUENCE: 46
tgctcagaat catgcaggtc                                               20

<210> SEQ ID NO 47
<211> LENGTH: 18
<212> TYPE: DNA
<213> ORGANISM: Artificial Sequence
<220> FEATURE:
<223> OTHER INFORMATION: oligonucleotide

<400> SEQUENCE: 47
gcgtgtcagc agcaagtg                                                 18

<210> SEQ ID NO 48
<211> LENGTH: 21
<212> TYPE: DNA
<213> ORGANISM: Artificial Sequence
<220> FEATURE:
<223> OTHER INFORMATION: oligonucleotide

<400> SEQUENCE: 48
tgcccacatc aaggagtatt t                                             21

<210> SEQ ID NO 49
<211> LENGTH: 19
<212> TYPE: DNA
<213> ORGANISM: Artificial Sequence
<220> FEATURE:
<223> OTHER INFORMATION: oligonucleotide

<400> SEQUENCE: 49
tttcgggtga caaagacga                                                    19

<210> SEQ ID NO 50
<211> LENGTH: 23
<212> TYPE: DNA
<213> ORGANISM: Artificial Sequence
<220> FEATURE:
<223> OTHER INFORMATION: oligonucleotide

<400> SEQUENCE: 50
gaaagcagtt agcaaggaaa ggt                                               23

<210> SEQ ID NO 51
<211> LENGTH: 26
<212> TYPE: DNA
<213> ORGANISM: Artificial Sequence
<220> FEATURE:
<223> OTHER INFORMATION: oligonucleotide

<400> SEQUENCE: 51
gacatatact ccatgtaggg aagtga                                            26

<210> SEQ ID NO 52
<211> LENGTH: 20
<212> TYPE: DNA
<213> ORGANISM: Artificial Sequence
<220> FEATURE:
<223> OTHER INFORMATION: oligonucleotide

<400> SEQUENCE: 52
tgtgggcaat gtcatcaaaa                                                   20

<210> SEQ ID NO 53
<211> LENGTH: 21
<212> TYPE: DNA
<213> ORGANISM: Artificial Sequence
<220> FEATURE:
<223> OTHER INFORMATION: oligonucleotide

<400> SEQUENCE: 53
gaagcacttg ctacctcttg c                                                 21

<210> SEQ ID NO 54
<211> LENGTH: 22
<212> TYPE: DNA
<213> ORGANISM: Artificial Sequence
<220> FEATURE:
<223> OTHER INFORMATION: oligonucleotide

<400> SEQUENCE: 54
atcctcctat ggtacgcaca aa                                                22

<210> SEQ ID NO 55
<211> LENGTH: 26
<212> TYPE: DNA
<213> ORGANISM: Artificial Sequence
<220> FEATURE:
<223> OTHER INFORMATION: oligonucleotide

<400> SEQUENCE: 55
ctccagtatt attgaagctg ctatcc                                            26

<210> SEQ ID NO 56
<211> LENGTH: 19

<210> SEQ ID NO 56
<211> LENGTH: 19
<212> TYPE: DNA
<213> ORGANISM: Artificial Sequence
<220> FEATURE:
<223> OTHER INFORMATION: oligonucleotide

<400> SEQUENCE: 56
agccacatcg ctcagacac                                            19

<210> SEQ ID NO 57
<211> LENGTH: 19
<212> TYPE: DNA
<213> ORGANISM: Artificial Sequence
<220> FEATURE:
<223> OTHER INFORMATION: oligonucleotide

<400> SEQUENCE: 57
gcccaatacg accaaatcc                                            19

<210> SEQ ID NO 58
<211> LENGTH: 22
<212> TYPE: DNA
<213> ORGANISM: Artificial Sequence
<220> FEATURE:
<223> OTHER INFORMATION: oligonucleotide

<400> SEQUENCE: 58
gcctaattta cagcaaccat ga                                        22

<210> SEQ ID NO 59
<211> LENGTH: 22
<212> TYPE: DNA
<213> ORGANISM: Artificial Sequence
<220> FEATURE:
<223> OTHER INFORMATION: oligonucleotide

<400> SEQUENCE: 59
gcctaattta cagcaaccat ga                                        22

<210> SEQ ID NO 60
<211> LENGTH: 27
<212> TYPE: DNA
<213> ORGANISM: Artificial Sequence
<220> FEATURE:
<223> OTHER INFORMATION: oligonucleotide

<400> SEQUENCE: 60
atataggtct cttcagcatt tattggt                                   27

<210> SEQ ID NO 61
<211> LENGTH: 26
<212> TYPE: DNA
<213> ORGANISM: Artificial Sequence
<220> FEATURE:
<223> OTHER INFORMATION: oligonucleotide

<400> SEQUENCE: 61
caaggaattc ttattgttct cactca                                    26

<210> SEQ ID NO 62
<211> LENGTH: 21
<212> TYPE: DNA
<213> ORGANISM: Artificial Sequence
<220> FEATURE:
<223> OTHER INFORMATION: oligonucleotide

<400> SEQUENCE: 62

-continued tgttcctcct tgtgcatctt c                                          21

<210> SEQ ID NO 63
<211> LENGTH: 21
<212> TYPE: DNA
<213> ORGANISM: Artificial Sequence
<220> FEATURE:
<223> OTHER INFORMATION: oligonucleotide

<400> SEQUENCE: 63
tgttcctcct tgtgcatctt c                                          21

<210> SEQ ID NO 64
<211> LENGTH: 20
<212> TYPE: DNA
<213> ORGANISM: Artificial Sequence
<220> FEATURE:
<223> OTHER INFORMATION: oligonucleotide

<400> SEQUENCE: 64
tgaaccacat tgtgcaaacc                                            20

<210> SEQ ID NO 65
<211> LENGTH: 20
<212> TYPE: DNA
<213> ORGANISM: Artificial Sequence
<220> FEATURE:
<223> OTHER INFORMATION: oligonucleotide

<400> SEQUENCE: 65
ctcctccttg agcatctcgt                                            20

<210> SEQ ID NO 66
<211> LENGTH: 20
<212> TYPE: DNA
<213> ORGANISM: Artificial Sequence
<220> FEATURE:
<223> OTHER INFORMATION: oligonucleotide

<400> SEQUENCE: 66
agatgctcaa ggaggagcac                                            20

<210> SEQ ID NO 67
<211> LENGTH: 19
<212> TYPE: DNA
<213> ORGANISM: Artificial Sequence
<220> FEATURE:
<223> OTHER INFORMATION: oligonucleotide

<400> SEQUENCE: 67
gatgtggatc acggtggac                                             19

<210> SEQ ID NO 68
<211> LENGTH: 21
<212> TYPE: DNA
<213> ORGANISM: Artificial Sequence
<220> FEATURE:
<223> OTHER INFORMATION: oligonucleotide

<400> SEQUENCE: 68
atttacacca tttcgcaaag c                                          21

<210> SEQ ID NO 69
<211> LENGTH: 26
<212> TYPE: DNA
<213> ORGANISM: Artificial Sequence

```
<220> FEATURE:
<223> OTHER INFORMATION: oligonucleotide

<400> SEQUENCE: 69
cactattgcc ttatcttcag cttcta                                        26

<210> SEQ ID NO 70
<211> LENGTH: 20
<212> TYPE: DNA
<213> ORGANISM: Artificial Sequence
<220> FEATURE:
<223> OTHER INFORMATION: oligonucleotide

<400> SEQUENCE: 70
tagcctcccc aaagtcttga                                               20

<210> SEQ ID NO 71
<211> LENGTH: 21
<212> TYPE: DNA
<213> ORGANISM: Artificial Sequence
<220> FEATURE:
<223> OTHER INFORMATION: oligonucleotide

<400> SEQUENCE: 71
aaatgacctc caccatatcc a                                             21

<210> SEQ ID NO 72
<211> LENGTH: 25
<212> TYPE: DNA
<213> ORGANISM: Artificial Sequence
<220> FEATURE:
<223> OTHER INFORMATION: oligonucleotide

<400> SEQUENCE: 72
ctttgctatt ttcagacaag attca                                         25

<210> SEQ ID NO 73
<211> LENGTH: 20
<212> TYPE: DNA
<213> ORGANISM: Artificial Sequence
<220> FEATURE:
<223> OTHER INFORMATION: oligonucleotide

<400> SEQUENCE: 73
gccaggaggt tctcaacaat                                               20

<210> SEQ ID NO 74
<211> LENGTH: 20
<212> TYPE: DNA
<213> ORGANISM: Artificial Sequence
<220> FEATURE:
<223> OTHER INFORMATION: oligonucleotide

<400> SEQUENCE: 74
tgacgccctc aatcaaagta                                               20

<210> SEQ ID NO 75
<211> LENGTH: 23
<212> TYPE: DNA
<213> ORGANISM: Artificial Sequence
<220> FEATURE:
<223> OTHER INFORMATION: oligonucleotide

<400> SEQUENCE: 75
tgacttataa gcacccatgt caa                                           23
```

```
<210> SEQ ID NO 76
<211> LENGTH: 20
<212> TYPE: DNA
<213> ORGANISM: Artificial Sequence
<220> FEATURE:
<223> OTHER INFORMATION: oligonucleotide

<400> SEQUENCE: 76
tacctgtcct gcgtgttgaa                                               20

<210> SEQ ID NO 77
<211> LENGTH: 23
<212> TYPE: DNA
<213> ORGANISM: Artificial Sequence
<220> FEATURE:
<223> OTHER INFORMATION: oligonucleotide

<400> SEQUENCE: 77
tctttgggta attttggga tct                                            23

<210> SEQ ID NO 78
<211> LENGTH: 24
<212> TYPE: DNA
<213> ORGANISM: Artificial Sequence
<220> FEATURE:
<223> OTHER INFORMATION: oligonucleotide

<400> SEQUENCE: 78
gatgagtaca aaagtcctga tcca                                          24

<210> SEQ ID NO 79
<211> LENGTH: 19
<212> TYPE: DNA
<213> ORGANISM: Artificial Sequence
<220> FEATURE:
<223> OTHER INFORMATION: oligonucleotide

<400> SEQUENCE: 79
ctgcagccac tggttctgt                                                19

<210> SEQ ID NO 80
<211> LENGTH: 20
<212> TYPE: DNA
<213> ORGANISM: Artificial Sequence
<220> FEATURE:
<223> OTHER INFORMATION: oligonucleotide

<400> SEQUENCE: 80
agacagcaga gcacacaagc                                               20

<210> SEQ ID NO 81
<211> LENGTH: 17
<212> TYPE: DNA
<213> ORGANISM: Artificial Sequence
<220> FEATURE:
<223> OTHER INFORMATION: oligonucleotide

<400> SEQUENCE: 81
tggttccttc cggtggt                                                  17

<210> SEQ ID NO 82
<211> LENGTH: 23
<212> TYPE: DNA
<213> ORGANISM: Artificial Sequence
<220> FEATURE:
<223> OTHER INFORMATION: oligonucleotide
```

<400> SEQUENCE: 82
gctggacaac ttgttgttaa agg                                    23

<210> SEQ ID NO 83
<211> LENGTH: 20
<212> TYPE: DNA
<213> ORGANISM: Artificial Sequence
<220> FEATURE:
<223> OTHER INFORMATION: oligonucleotide

<400> SEQUENCE: 83
ctcagacaag gcttggcaac                                        20

<210> SEQ ID NO 84
<211> LENGTH: 20
<212> TYPE: DNA
<213> ORGANISM: Artificial Sequence
<220> FEATURE:
<223> OTHER INFORMATION: oligonucleotide

<400> SEQUENCE: 84
cactcccaaa acctgctgag                                        20

<210> SEQ ID NO 85
<211> LENGTH: 22
<212> TYPE: DNA
<213> ORGANISM: Artificial Sequence
<220> FEATURE:
<223> OTHER INFORMATION: oligonucleotide

<400> SEQUENCE: 85
tctcttcaga agtgcaaggg ta                                     22

<210> SEQ ID NO 86
<211> LENGTH: 20
<212> TYPE: DNA
<213> ORGANISM: Artificial Sequence
<220> FEATURE:
<223> OTHER INFORMATION: oligonucleotide

<400> SEQUENCE: 86
cccccactgg atctgaagta                                        20

<210> SEQ ID NO 87
<211> LENGTH: 23
<212> TYPE: DNA
<213> ORGANISM: Artificial Sequence
<220> FEATURE:
<223> OTHER INFORMATION: oligonucleotide

<400> SEQUENCE: 87
gagtgactgg aaatagggtc ttg                                    23

<210> SEQ ID NO 88
<211> LENGTH: 19
<212> TYPE: DNA
<213> ORGANISM: Artificial Sequence
<220> FEATURE:
<223> OTHER INFORMATION: oligonucleotide

<400> SEQUENCE: 88
cctgaggctt ctccaggtg                                         19

<210> SEQ ID NO 89

```
<211> LENGTH: 18
<212> TYPE: DNA
<213> ORGANISM: Artificial Sequence
<220> FEATURE:
<223> OTHER INFORMATION: oligonucleotide

<400> SEQUENCE: 89
ccaggacctt cagcgtca                                                 18

<210> SEQ ID NO 90
<211> LENGTH: 18
<212> TYPE: DNA
<213> ORGANISM: Artificial Sequence
<220> FEATURE:
<223> OTHER INFORMATION: oligonucleotide

<400> SEQUENCE: 90
cttggaagca cggcctac                                                 18

<210> SEQ ID NO 91
<211> LENGTH: 19
<212> TYPE: DNA
<213> ORGANISM: Artificial Sequence
<220> FEATURE:
<223> OTHER INFORMATION: oligonucleotide

<400> SEQUENCE: 91
cgggaacata tgcaccagt                                                19

<210> SEQ ID NO 92
<211> LENGTH: 18
<212> TYPE: DNA
<213> ORGANISM: Artificial Sequence
<220> FEATURE:
<223> OTHER INFORMATION: oligonucleotide

<400> SEQUENCE: 92
agctgtgctg gcgagaag                                                 18

<210> SEQ ID NO 93
<211> LENGTH: 19
<212> TYPE: DNA
<213> ORGANISM: Artificial Sequence
<220> FEATURE:
<223> OTHER INFORMATION: oligonucleotide

<400> SEQUENCE: 93
ttggagtcca gcatgtgtg                                                19

<210> SEQ ID NO 94
<211> LENGTH: 21
<212> TYPE: DNA
<213> ORGANISM: Artificial Sequence
<220> FEATURE:
<223> OTHER INFORMATION: oligonucleotide

<400> SEQUENCE: 94
gcgaactcat ctttgccagt a                                             21

<210> SEQ ID NO 95
<211> LENGTH: 19
<212> TYPE: DNA
<213> ORGANISM: Artificial Sequence
<220> FEATURE:
<223> OTHER INFORMATION: oligonucleotide

<400> SEQUENCE: 95
```
ccagcatctt caccgtcag                                                        19

<210> SEQ ID NO 96
<211> LENGTH: 19
<212> TYPE: DNA
<213> ORGANISM: Artificial Sequence
<220> FEATURE:
<223> OTHER INFORMATION: oligonucleotide

<400> SEQUENCE: 96
ttcagcacct gatggccta                                                        19

<210> SEQ ID NO 97
<211> LENGTH: 20
<212> TYPE: DNA
<213> ORGANISM: Artificial Sequence
<220> FEATURE:
<223> OTHER INFORMATION: oligonucleotide

<400> SEQUENCE: 97
aaagggatgt ggctggagat                                                       20

<210> SEQ ID NO 98
<211> LENGTH: 21
<212> TYPE: DNA
<213> ORGANISM: Artificial Sequence
<220> FEATURE:
<223> OTHER INFORMATION: oligonucleotide

<400> SEQUENCE: 98
cagacctgac catcattgac c                                                     21

<210> SEQ ID NO 99
<211> LENGTH: 20
<212> TYPE: DNA
<213> ORGANISM: Artificial Sequence
<220> FEATURE:
<223> OTHER INFORMATION: oligonucleotide

<400> SEQUENCE: 99
tgatgagagc cttgatctgc                                                       20

<210> SEQ ID NO 100
<211> LENGTH: 20
<212> TYPE: DNA
<213> ORGANISM: Artificial Sequence
<220> FEATURE:
<223> OTHER INFORMATION: oligonucleotide

<400> SEQUENCE: 100
gacctgaagg gaaccatcct                                                       20

<210> SEQ ID NO 101
<211> LENGTH: 20
<212> TYPE: DNA
<213> ORGANISM: Artificial Sequence
<220> FEATURE:
<223> OTHER INFORMATION: oligonucleotide

<400> SEQUENCE: 101
tgtgttttcg gtgactgtcc                                                       20

<210> SEQ ID NO 102
<211> LENGTH: 20
<212> TYPE: DNA

<213> ORGANISM: Artificial Sequence
<220> FEATURE:
<223> OTHER INFORMATION: oligonucleotide

<400> SEQUENCE: 102
ggatcagctg cagaactggt                                          20

<210> SEQ ID NO 103
<211> LENGTH: 21
<212> TYPE: DNA
<213> ORGANISM: Artificial Sequence
<220> FEATURE:
<223> OTHER INFORMATION: oligonucleotide

<400> SEQUENCE: 103
tttctgttcc aattcctcca a                                        21

<210> SEQ ID NO 104
<211> LENGTH: 27
<212> TYPE: DNA
<213> ORGANISM: Artificial Sequence
<220> FEATURE:
<223> OTHER INFORMATION: oligonucleotide

<400> SEQUENCE: 104
gaggaatagt ctacaaagga agacttg                                  27

<210> SEQ ID NO 105
<211> LENGTH: 27
<212> TYPE: DNA
<213> ORGANISM: Artificial Sequence
<220> FEATURE:
<223> OTHER INFORMATION: oligonucleotide

<400> SEQUENCE: 105
actataaagg atggagtaaa tgacagg                                  27

<210> SEQ ID NO 106
<211> LENGTH: 21
<212> TYPE: DNA
<213> ORGANISM: Artificial Sequence
<220> FEATURE:
<223> OTHER INFORMATION: oligonucleotide

<400> SEQUENCE: 106
aaggctagca gtcatccaac a                                        21

<210> SEQ ID NO 107
<211> LENGTH: 22
<212> TYPE: DNA
<213> ORGANISM: Artificial Sequence
<220> FEATURE:
<223> OTHER INFORMATION: oligonucleotide

<400> SEQUENCE: 107
agcaacttca tggctaacag tg                                       22

<210> SEQ ID NO 108
<211> LENGTH: 24
<212> TYPE: DNA
<213> ORGANISM: Artificial Sequence
<220> FEATURE:
<223> OTHER INFORMATION: oligoncucleotide

<400> SEQUENCE: 108
ccagtgtcta aagaacctgg aaac                                     24

<210> SEQ ID NO 109
<211> LENGTH: 20
<212> TYPE: DNA
<213> ORGANISM: Artificial Sequence
<220> FEATURE:
<223> OTHER INFORMATION: oligonucleotide

<400> SEQUENCE: 109
tcagggacag tggtcagttg                                                 20

<210> SEQ ID NO 110
<211> LENGTH: 20
<212> TYPE: DNA
<213> ORGANISM: Artificial Sequence
<220> FEATURE:
<223> OTHER INFORMATION: oligonucleotide

<400> SEQUENCE: 110
gacaagcctg tagcccatgt                                                 20

<210> SEQ ID NO 111
<211> LENGTH: 18
<212> TYPE: DNA
<213> ORGANISM: Artificial Sequence
<220> FEATURE:
<223> OTHER INFORMATION: oligonucleotie

<400> SEQUENCE: 111
tctcagctcc acgccatt                                                   18

<210> SEQ ID NO 112
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 112
gcaggggagt cagcagag                                                   18

<210> SEQ ID NO 113
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 113
agaggcagac gaaccatagc                                                 20

<210> SEQ ID NO 114
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 114
cccaagcctg tgagcaag                                                   18

<210> SEQ ID NO 115
<211> LENGTH: 20
<212> TYPE: DNA
<213> ORGANISM: Artificial Sequence
<220> FEATURE:

<223> OTHER INFORMATION: oligonucleotide primer

<400> SEQUENCE: 115
catacttggt ggcattctgc                                          20

<210> SEQ ID NO 116
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 116
ttgcccttta cgtatctgct c                                        21

<210> SEQ ID NO 117
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 117
gctacttctg tgcccaccat                                          20

<210> SEQ ID NO 118
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 118
ggggtgtgcc tgtctgttac                                          20

<210> SEQ ID NO 119
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 119
gatgccatct tcagcgtagg                                          20

<210> SEQ ID NO 120
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 120
acagcagaag cagccaaaat                                          20

<210> SEQ ID NO 121
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 121
gaatcttcag aggagcagca c                                        21

```
<210> SEQ ID NO 122
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 122
gctctcgata tccggtagga                                                    20

<210> SEQ ID NO 123
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 123
gcctgaccta gctaagacac ttct                                               24

<210> SEQ ID NO 124
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 124
agcactggga gtttgatgct                                                    20

<210> SEQ ID NO 125
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 125
ggcacacacc acgttctct                                                     19

<210> SEQ ID NO 126
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 126
accaagggcc attgtgaat                                                     19

<210> SEQ ID NO 127
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 127
aatcgggcca gagaatagtg                                                    20
```

5'-TRIPHOSPHATE OLIGORIBONUCLEOTIDES

FIELD

Generally, the field is RNA-based therapeutic molecules. More specifically, the field is 5'-triphoshpate oligoribonucleotide immune system agonists and pharmaceutical compositions comprising the same.

RELATED APPLICATIONS

This application is related to U.S. patent application Ser. No. 14/177,866 filed 11 Feb. 2014. The related application is incorporated by reference herein.

BACKGROUND

The innate immune system has evolved numerous molecular sensors and signaling pathways to detect, contain and clear viral infections (Takeuchi O and Akira S *Immunol Rev* 227, 75-86 (2009); Yoneyama M and Fujita T, *Rev Med Virol* 20, 4-22 (2010); Wilkins C and Gale M *Curr Opin Immunol* 22, 41-47 (2010); and Brennan K and Bowie A G *Curr Opin Microbiol* 13, 503-507 (2010); all of which are incorporated by reference herein.) Viruses are sensed by a subset of pattern recognition receptors (PRRs) that recognize evolutionarily conserved structures known as pathogen-associated molecular patterns (PAMPs). Classically, viral nucleic acids are the predominant PAMPs detected by these receptors during infection. These sensing steps contribute to the activation of signaling cascades that culminate in the early production of antiviral effector molecules, cytokines and chemokines responsible for the inhibition of viral replication and the induction of adaptive immune responses (Takeuchi O and Akira S *Cell* 140, 805-820 (2010), Liu S Y et al, *Curr Opin Immunol* 23, 57-64 (2011); and Akira S et al, *Cell* 124, 783-801 (2006); all of which are incorporated by reference herein). In addition to the nucleic acid sensing by a subset of endosome-associated Toll-like receptors (TLR), viral RNA structures within the cytoplasm are recognized by members of the retinoic acid-inducible gene-I (RIG-I)-like receptors (RLRs) family, including the three DExD/H box RNA helicases RIG-I, Mda5 and LGP-2 (Kumar H et al, *Int Rev Immunol* 30, 16-34 (2011); Loo Y M and Gale M, *Immunity* 34, 680-692 (2011); Belgnaoui S M et al, *Curr Opin Immunol* 23, 564-572 (2011); Beutler B E, *Blood* 113, 1399-1407 (2009); Kawai T and Akira S, *Immunity* 34, 637-650 (2011); all of which are incorporated by reference herein.)

RIG-I is a cytosolic multidomain protein that detects viral RNA through its helicase domain (Jiang F et al, *Nature* 479, 423-427 (2011) and Yoneyama M and Fujita T, *J Biol Chem* 282, 15315-15318 (2007); both of which are incorporated by reference herein). In addition to its RNA sensing domain, RIG-I also possesses an effector caspase activation and recruitment domain (CARD) that interacts with the mitochondrial adaptor MAVS, also known as VISA, IPS-1, and Cardif (Kawai T et al, *Nat Immunol* 6, 981-988 (2005) and Meylan E et al, *Nature* 437, 1167-1172 (2005), both of which are incorporated by reference herein.) Viral RNA binding alters RIG-I conformation from an auto-inhibitory state to an open conformation exposing the CARD domain, resulting in RIG-I activation which is characterized by ATP hydrolysis and ATP-driven translocation of RNA (Schlee M et al, *Immunity* 31, 25-34 (2009); Kowlinski E et al, *Cell* 147, 423-435 (2011); and Myong S et al, *Science* 323, 1070-1074 (2011); all of which are incorporated by reference herein). Activation of RIG-I also allows ubiquitination and/or binding to polyubiquitin. In recent studies, polyubiquitin binding has been shown to induce the formation of RIG-I tetramers that activate downstream signaling by inducing the formation of prion-like fibrils comprising the MAVS adaptor (Jiang X et al, *Immunity* 36, 959-973 (2012); incorporated by reference herein). MAVS then triggers the activation of IRF3, IRF7 and NF-κB through the IKK-related serine kinases TBK1 and IKKE (Sharma S et al, *Science* 300, 1148-1151 (2003); Xu L G et al, *Molecular Cell* 19, 727-740 (2005); and Seth R B et al, *Cell* 122, 669-682 (2005); all of which are incorporated by reference herein). This in turn leads to the expression of type I interferons (IFNβ and IFNα), as well as pro-inflammatory cytokines and anti-viral factors (Tamassia N et al, *J Immunol* 181, 6563-6573 (2008) and Kawai T and Akira S, *Ann NY Acad Sci* 1143, 1-20 (2008); both of which are incorporated by reference herein.) A secondary response involving the induction of IFN stimulated genes (ISGs) is induced by the binding of IFN to its cognate receptor (IFNα/βR). This triggers the JAK-STAT pathway to amplify the antiviral immune response (Wang B X and Fish E N *Trends Immunol* 33, 190-197 (2012); Nakhaei P et al, Activation of Interferon Gene Expression Through Toll-like Receptor-dependent and -independent Pathways, in *The Interferons*, Wiley-VCH Verlag GmbH and Co KGaA, Weinheim F R G (2006); Sadler A J and Wiliams B R, *Nat Rev Immunol* 8, 559-568 (2008); and Schoggins J W et al, *Nature* 472, 481-485 (2011); all of which are incorporated by reference herein.)

The nature of the ligand recognized by RIG-I has been the subject of intense study given that PAMPs are the initial triggers of the antiviral immune response. In vitro synthesized RNA carrying an exposed 5' terminal triphosphate (5'ppp) moiety was identified as a RIG-I agonist (Hornung V et al, *Science* 314, 994-997 (2006); Pichlmair A et al, *Science* 314, 997-1001 (2006); and Kim D H et al, *Nat Biotechol* 22, 321-325 (2004); all of which are incorporated by reference herein). The 5'ppp moiety is added to the end of all viral and eukaryotic RNA molecules generated by RNA polymerization. However, in eukaryotic cells, RNA processing in the nucleus cleaves the 5'ppp end and the RNA is capped prior to release into the cytoplasm. The eukaryotic immune system evolved the ability to distinguish viral 'non-self' 5'ppp RNA from cellular 'self' RNA through RIG-I (Fujita T, *Immunity* 31, 4-5 (2009); incorporated by reference herein). Further characterization of RIG-I ligand structure indicated that blunt base pairing at the 5' end of the RNA and a minimum double strand (ds) length of 20 nucleotides were also important for RIG-I signaling (Schlee M and G Hartmann, *Molecular Therapy* 18, 1254-1262 (2010); incorporated by reference herein). Further studies indicated that a dsRNA length of less than 300 base pairs led to RIG-I activation but a dsRNA length of more than 2000 bp lacking a 5'ppp (as is the case with poly I:C) failed to activate RIG-I. (Kato H et al, *J Exp Med* 205, 1601-1610 (2008); incorporated by reference herein).

RNA extracted from virally infected cells, specifically viral RNA genomes or viral replicative intermediates, was also shown to activate RIG-I (Baum A et al, *Proc Natl Acad Sci USA* 107, 16303-16308 (2010); Rehwinkel J and Sousa C R E, *Science* 327, 284-286 (2010); and Rehwinkel J et al, *Cell* 140, 397-408 (2010); all of which are incorporated by reference herein). Interestingly, the highly conserved 5' and 3' untranslated regions (UTRs) of negative single strand RNA virus genomes display high base pair complementarity and the panhandle structure theoretically formed by the viral genome meets the requirements for RIG-I recognition. The elucidation of the crystal structure of RIG-I highlighted the molecular interactions between RIG-I and 5'ppp-dsRNA (Cui S et al, *Molecular Cell* 29, 169-179 (2008); incorporated by reference herein), providing a structural basis for the conformational changes involved in exposing the CARD domain for effective downstream signaling.

SUMMARY

Disclosed herein is a synthetic oligoribonucleotide at least 41 nucleotides in length that can form a hairpin structure comprising at least 17 base pairs. The synthetic oligoribonucleotide further comprises a triphosphate group at its 5' end. Examples of the oligoribonucleotide can include sequences such as SEQ ID NO: 10, SEQ ID NO: 11, or SEQ ID NO: 12 described herein. The oligoribonucleotide can also be of at least 99 nucleotides in length and can form a hairpin structure of at least 48 base pairs. Examples of this aspect of the oligonucleotide can include sequences such as SEQ ID NO: 15 or SEQ ID NO: 16 described herein. In such an oligoribonucleotide, the hairpin structure can comprise at least 26 consecutive U-A base pairs. Examples of this aspect of the oligoribonucleotide can include sequences such as SEQ ID NO: 13, SEQ ID NO: 14 and SEQ ID NO: 17 described herein.

Further disclosed are pharmaceutical compositions comprising a therapeutically effective amount of any of the disclosed synthetic oligoribonucleotides and a pharmaceutically acceptable carrier. Such compositions can also include viral antigens such as an influenza virus like particle and be formulated as a vaccine.

Further disclosed are methods of treating a viral infection such as vesicular stomatitis virus, dengue virus, human immunodeficiency virus, chikungunya virus, or influenza virus.

BRIEF DESCRIPTION OF THE SEVERAL VIEWS OF THE DRAWINGS

Some of the drawings were provided in color and can be better understood through the use of color reproduction. Applicants consider the color drawings to be part of the original disclosure and reserve the right to provide color drawings in later proceedings.

FIG. 1 is a set of four bar graphs summarizing the results when lung epithelial A549 cells were transfected with VSV WT, M5, M8, poly (I:C), or CL9 aptamer at the indicated concentrations. Total RNA was extracted, subjected to reverse transcription, and analyzed by real-time PCR using CXCL10-, IL1a-, IL29-, TNFα-, and GAPDH-specific primers.

FIG. 2A is an image of a 15% TBE-urea polyacrylamide gel showing in vitro transcribed WT and selected mutants therein—M1, M2, M3, M4, and M5 after purification via spin column.

FIG. 2B is an image of a 15% TBE-urea polyacrylamide gel showing synthesized and purified WT subjected to RNase A or DNase I treatment as indicated.

FIG. 2C is an image of a 15% TBE-urea polyacrylamide gel showing synthesized and purified M5 (5'pppSEQ ID NO: 10) subjected to RNase A or DNase I treatment as indicated.

FIG. 3A is a bar graph summarizing the results of A549 cells transfected with reporter assay plasmids then transfected with the indicated RNA agonists at the given concentrations for 24 hours. IFN-β reporter gene activity was then measured by the Dual-Luciferase Reporter Assay kit.

FIG. 3B is a set of three bar graphs summarizing the results of A549 cells transfected with 0.1 ng/ml WT, M5, poly (I:C), or CL2 aptamer for 24 hours. Total RNA was extracted, subjected to reverse transcription, and analyzed by real-time PCR using ISG56-, IFNβ-, IL1a-, and GAPDH-specific primers.

FIG. 3C is an image of an immunoblot of A549 cells transfected with 0.01 ng/ml of each of the 5'pppRNA variants for 24 hours then infected or not with influenza H1N1 strain A/PR/8/34 (MOI 0.2). After 24 hours of infection, whole cell extracts were resolved by native gel electrophoresis and revealed by immunoblot using NS1, ISG56, pSTAT1, and β-actin antibodies.

FIG. 3D is a bar graph summarizing the results when A549 cells were transfected with 1 ng/ml of 5'pppRNAs including M5 (5'ppp-SEQ ID NO: 10), aptamers, or poly (I:C), then treated with dengue virus serotype 2 strain NGC (MOI 0.5). Total RNA was extracted, subjected to reverse transcription, and analyzed by real-time PCR using dengue- and GAPDH-specific primers.

FIG. 4A is a bar graph summarizing the results when A549 cells were transfected with M5, M6, M7, and M8 5'pppRNA (5'pppSEQ ID NO: 10, 5'pppSEQ ID NO: 11, 5'pppSEQ ID NO: 12, and 5'pppSEQ ID NO: 13, respectively) at a range of concentrations (0.01, 0.1, 1, and 10 ng/ml) for 18 hours then challenged with dengue virus (MOI 0.5) for 24 hours. ICS staining and flow cytometry was performed to quantify the percentage of dengue E protein-positive cells.

FIG. 4B is a bar graph summarizing the results when A549 cells were transfected with M5, M6, M7, or M8 at the indicated concentrations (0.01, 0.1, 1, and 10 ng/ml) for 18 hours then challenged with dengue virus (MOI 0.5) for 24 hours. Total RNA was extracted, subjected to reverse transcription, and analyzed by real-time PCR using dengue- and GAPDH-specific primers.

FIG. 4C is a bar graph summarizing the results when A549 cells were transfected with M8 (5'pppSEQ ID NO: 13) at low concentrations (0.1 to 0.000046 ng/ml at 1:3 dilutions). ICS staining and flow cytometry was performed to quantify the percentage of dengue E protein-positive cells.

FIG. 5 is a drawing of secondary structures of optimized oligonucleotides generated using the RNAfold Web Server (University of Vienna).

FIG. 6A is a bar graph summarizing the expression of RIG-I or TL3/MDA5 were inhibited by siRNA in A549 cells for 48 hours. Cells were then treated with M8 (0.1 ng/ml) for 24 hours, infected with dengue (MOI 0.5) and viral replication was evaluated 24 hours later by ICS staining and flow cytometry to quantify the percentage of dengue E protein-positive cells.

FIG. 6B is an image of an immunoblot of the results when A549 cells in which expression of RIG-I, TLR3, or MDA5 was knocked down, were treated or not (NT) with M8 for 24 hours. Whole cell extracts were resolved by native gel electrophoresis and revealed by immunoblot using RIG-I, TLR3, MDA5, STAT1, and β-actin antibodies.

FIG. 7A: Enhanced antiviral activity against influenza is evident in M8 (comprising SEQ ID NO: 13)-treated A549 cells. FIG. 7A is an image of an immunoblot of the results when A549 cells were pre-treated with WT, M5, or M8 (10, 1, 0.1, and 0.01 ng/ml) for 24 hours, and then infected influenza H1N1 strain A/PR/8/34 (MOI 0.2). After 24 hours of infection, whole cell extracts were resolved by native gel electrophoresis and revealed by immunoblot using NS1, pSTAT1, ISG56, and β-actin antibodies.

FIG. 7B: M8 inhibits dengue virus infection in human primary immune cells. FIG. 7B is a bar graph summarizing the results when monocyte-differentiated dendritic cells (MDDCs) were transfected with WT, M5, or M8 at the indicated concentrations (1000, 100, 10, and 1 ng/ml) for 24 hours and infected with dengue virus (MOI 10). After 24 hours, intracellular dengue replication was evaluated by ICS staining and flow cytometry to quantify the percentage of dengue E protein-positive cells.

FIG. 8A is a drawing of the structure of a sequence based on M8 (M8A-5'pppSEQ ID NO: 14). M8A was designed by changing part of the sequence of M8. Like M8, M8A is 99 nucleotides in length.

FIG. 9A is a bar graph summarizing the results when A549 cells were transfected with M8, M8A, or M8B at concentrations from (0.000001 to 1 ng/ml) for 24 hours then infected with dengue virus (MOI 0.5). After 24 hours, intracellular dengue replication was evaluated by ICS staining and flow cytometry to quantify the percentage of dengue E protein-positive cells.

FIG. 9B is a set of six bar graphs summarizing the results when A549 cells were transfected with M8, M8A, or M8B (0.01 ng/ml) for 24 hours. Total RNA was extracted, subjected to reverse transcription, and analyzed by real-time PCR using ISG56-, IFN-β-, IL-1a, IL6, CXCL10-, TNFα-,-and GAPDH-specific primers.

FIG. 10 is a timeline of mouse vaccination experiments. Numbers above line indicate weeks.

FIG. 11A is a plot showing total HA-specific IgG quantified in vaccinated mice two weeks after the booster vaccine. X axes represents sample dilutions and Y axes represents absorbance at 414 nm.

FIG. 11B is a plot of total IgG titers in sera of vaccinated mice two weeks after the booster vaccine. Titer was determined by ELISA.

FIG. 11C is a plot of titers of HA neutralizing antibodies in sera of vaccinated mice. Titer was determined by hemagglutination inhibition assay (HAI).

FIG. 11D is a plot of percent weight change (Y axes) in vaccinated mice upon challenge with reassorted H5N1 over time (days, X axes).

FIG. 12A is a Kaplan-Meier survival function of vaccinated mice upon challenge with reassorted H5N1. Green line indicates mice vaccinated with M5+VLP, dark red line indicates mice vaccinated with VLP only, and purple line indicates mice vaccinated with M5 and control mice.

FIG. 12B is a plot of the relative sickness score of mice vaccinated according to the indicated conditions upon challenge with reassorted H5N1.

FIG. 12C is a plot of apoptosis observed by TUNEL assay in lungs of vaccinated mice upon challenge with reassorted H5N1.

FIG. 13 is a set of four photomicrographs showing the results of histopathological examination of H&E stained lung sections in mice vaccinated under the indicated conditions upon challenge with reassorted H5N1. Arrow indicates presence or absence of inflammation around bronchial tubes.

FIG. 14A is a plot summarizing an RT-PCR assessment of IFN-β mRNA levels in the quadriceps muscles of mice injected with various amounts of M5 (comprising SEQ ID NO: 10) compared to control.

FIG. 14B is a plot summarizing an RT-PCR assessment of IFN-β mRNA levels in the quadriceps muscles of mice injected with various amounts of M8 compared to control.

FIG. 15A is a plot summarizing the results when mice were inoculated intravenously with 2 or 10 µg of control, WT, M5 or M8 with in vivo JetPEI then injected with chikungunya virus via the footpad. Ipsilateral foot swelling of mice was measured with a caliper over ten days.

FIG. 15B is a plot summarizing the results when mice were injected with 2 or 10 μg of control, WT, M5 or M8 along with in vivo JetPEI, then injected with chikungunya virus via the footpad. At 48 hours post-infection, RNA from the leg muscle was extracted and the number of genome copies of chikungunya RNA was measured by real time qPCR.

FIG. 16A is a schematic representation of 5'pppRNA sequences that include variations of the wild type (WT) VSV-derived 5'pppRNA (M1-M8), SELEX-selected RIG-I aptamers, and poly (I:C).

FIG. 20B is a set of bar graphs of viral titers in cell culture supernatants from (FIG. 20A) were determined by plaque assay. Data are from two independent experiments performed in triplicate and represent the means±SEM.

Figure 23A:
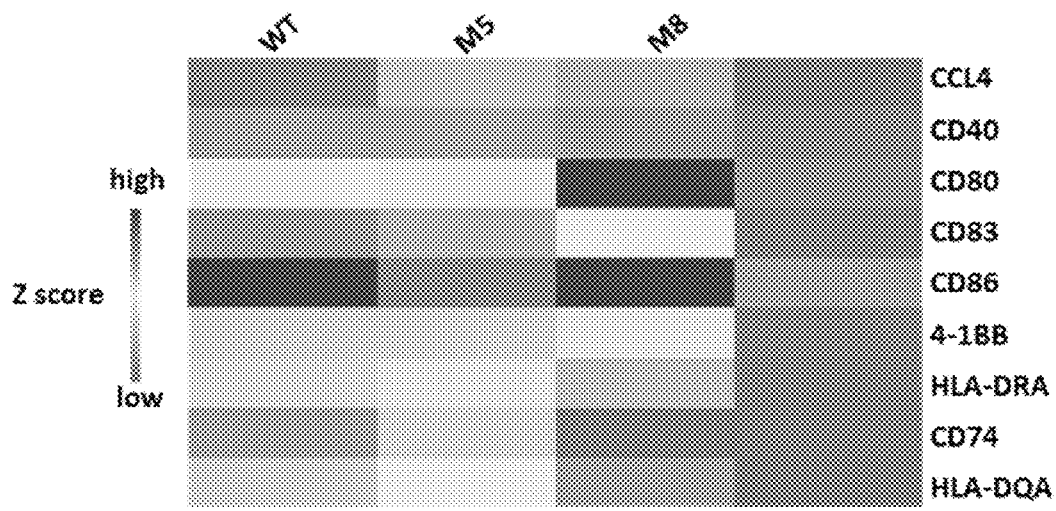
Figure 23B:
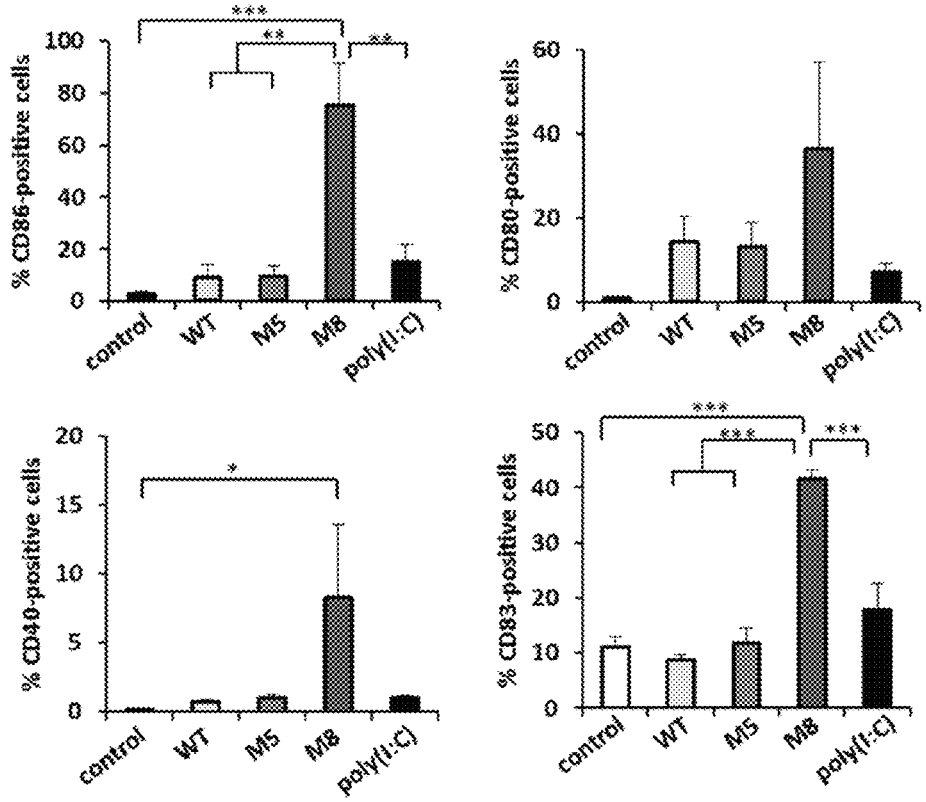

Data in FIGS. 23A and 23B were obtained by transfecting monocyte-derived dendritic cells (MDDCs) with WT, M5, or M8 5'pppRNA or poly(I:C) increases expression of activation and differentiation markers and their mRNA levels. MDDC were isolated from peripheral blood mononuclear cells (n=4), differentiated, and transfected with 10 ng WT, M5, M8, or poly(I:C) using HiPerFect transfection reagent for 24 h.

FIG. 23A is a heat map showing the results of gene expression analysis using the Fluidigm BioMark platform for the indicated genes in MDDCs transfected with 20 fmol of WT, M5, M8, or poly(I:C) for 24 h.

FIG. 23B is a set of four bar graphs showing the surface expression of the indicated activation and differentiation markers as assessed by flow cytometry (mean±SEM); * $P \leq 0.05$;  $P \leq 0.01$; * $P \leq 0.005$.

FIGS. 24A-24D summarize the Protective efficacy of a VLP vaccine adjuvanted with M5, M8 or poly(I:C). Mice (n=5) were immunized intramuscularly with 2 μg of VLP alone or combined with 5 μg M5, M8 or poly(I:C) as a 50 μL injection. Three weeks later the mice were challenged with 5,000 pfu of H5N1.

Figure 24A:
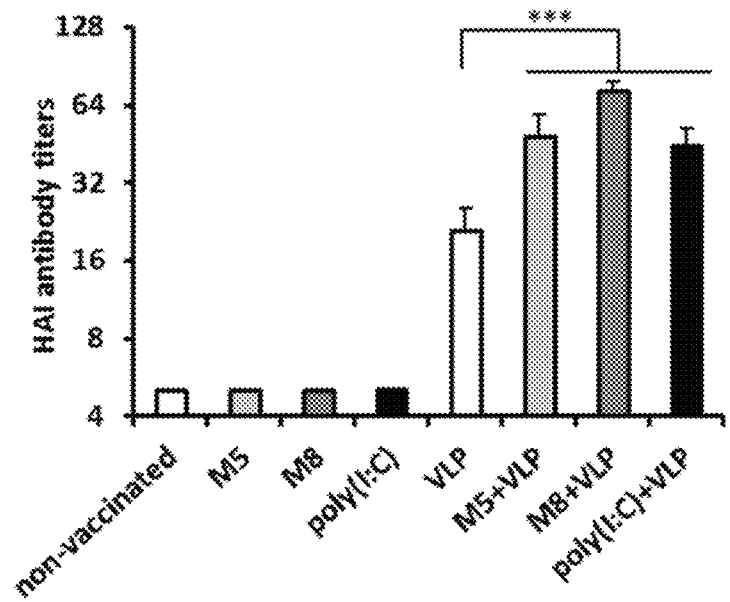

FIG. 24A is a bar graph showing hemagglutination inhibition (HAI) antibody titers in immunized mice prior to infection were determined by hemagglutination inhibition assay using horse red blood cells.

Figure 24B:
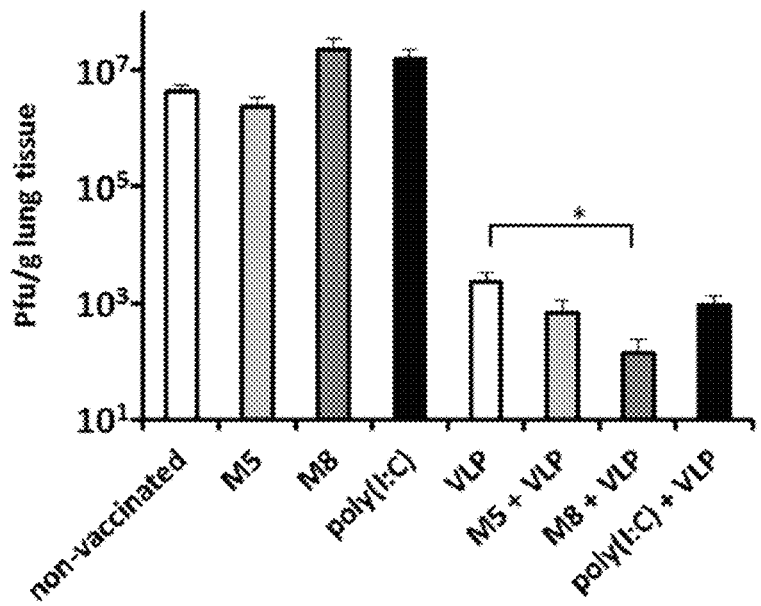

FIG. 24B is a bar graph showing the results of an assessment of viral replication in lungs of infected animals 3 days post infection by plaque assay.

Figure 24C:
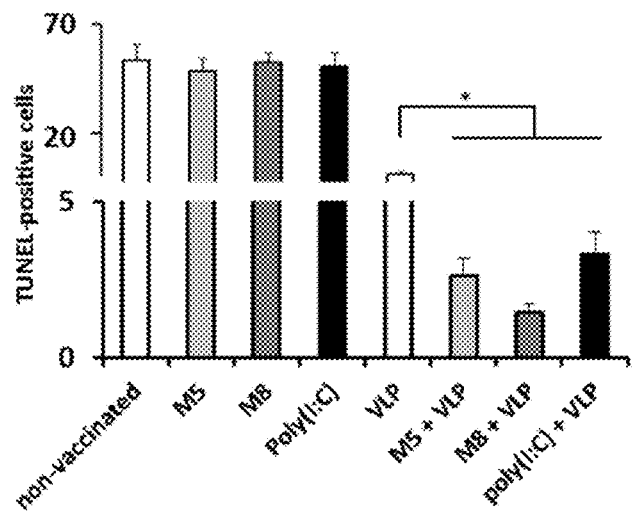

FIG. 24C is a bar graph showing TUNEL-positive (apoptotic) lung cells in infected mice were quantified using a TUNEL assay.

Figure 24D:
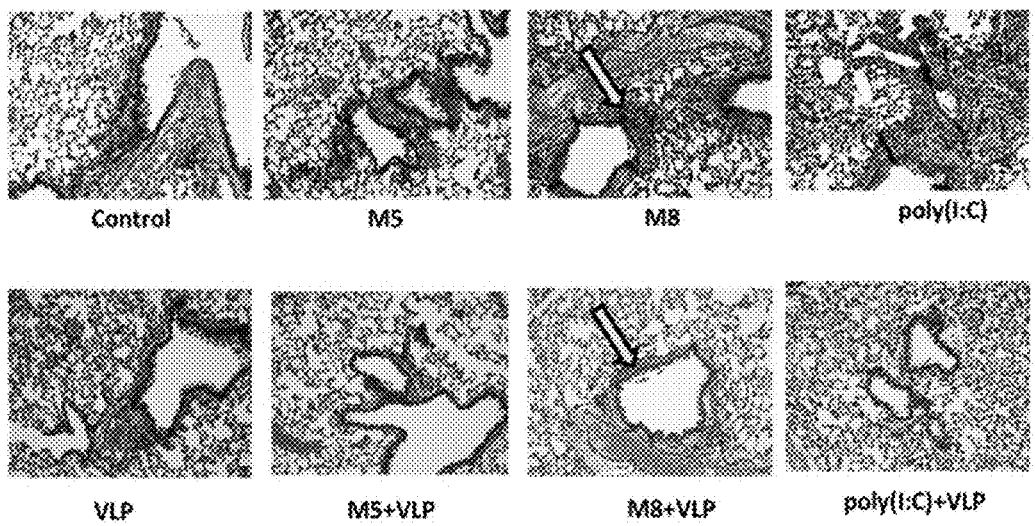

FIG. 24D is a set of eight images showing H&E staining of paraffin embedded lung cross-sections from mice 3 days after challenge. Yellow arrow indicates airways of mice that were vaccinated with either M8-only (top) or M8-VLP (bottom). All values are expressed as the mean±SEM. * P≤0.05; *** P≤0.005.

Figure 25A:
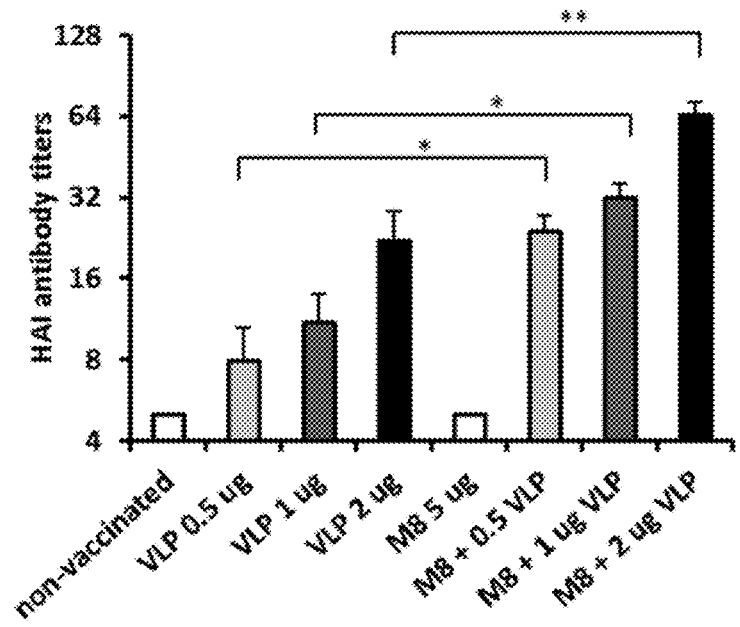

FIG. 25A is a bar graph showing the dose-response to VLP and M8 by HAI antibody titer. Mice (n=5) were immunized with the indicated doses of VLP (2 μg-0.5 μg) in combination with 5 μg of M8. Three weeks later, mice were challenged with H5N1, and lungs from infected animals were harvested 3 days post-challenge. HAI antibody titers in immunized mice prior to infection were determined by HAI assay.

Figure 25B:
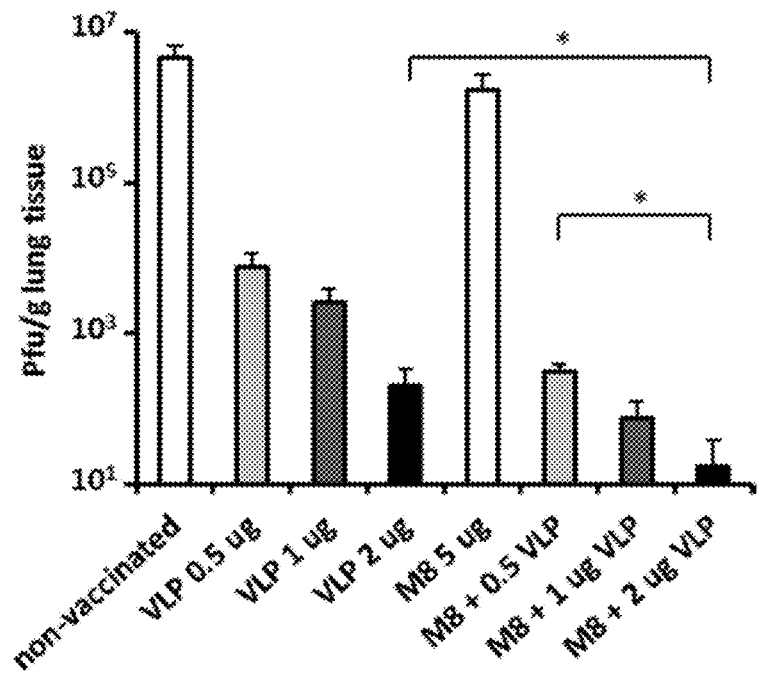

FIG. 25B is a bar graph showing the dose-response to VLP and M8 by viral plaque assay. Mice (n=5) were immunized with decreasing doses of VLP (2 μg-0.5 μg) in combination with 5 μg of M8, three weeks later challenged with H5N1, and lungs from infected animals were harvested 3 days post-challenge. Viral replication in lungs was assessed by plaque assay.

For FIG. 25C-25F, Mice were immunized with 0.5 μg of VLP with 0.1-5 μg of M8. HAI antibody titers were determined by HAI assay.

Figure 25C:
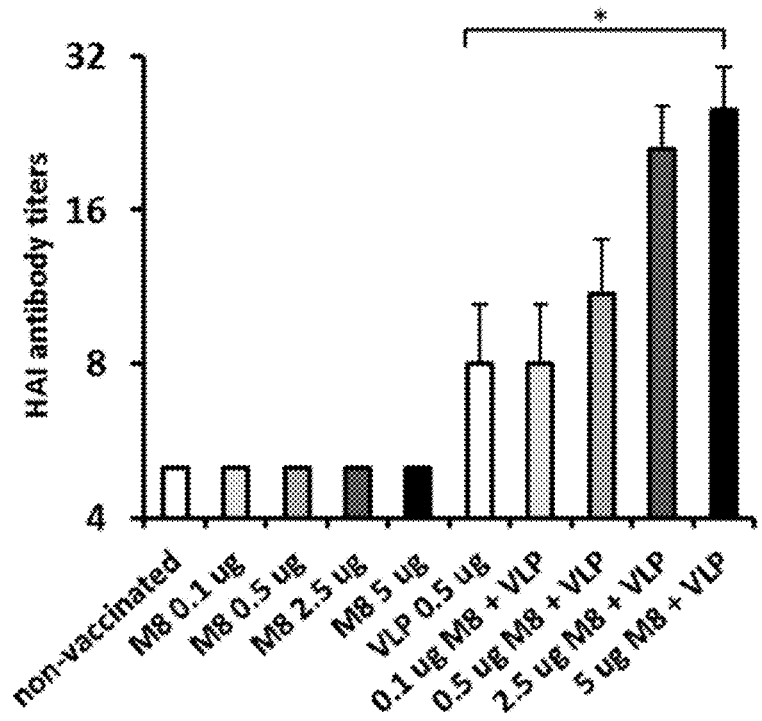

FIG. 25C is a bar graph of influenza HAI antibody titers.

Figure 25D:
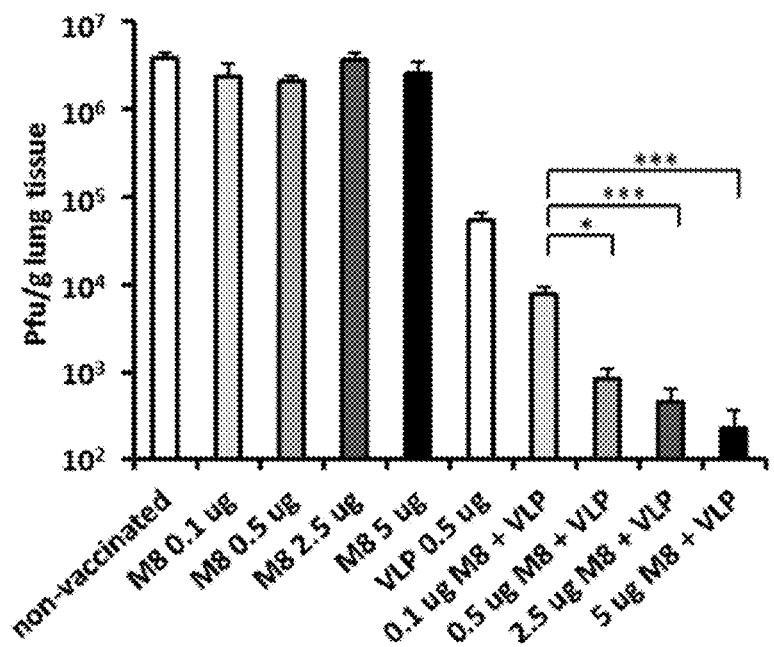

FIG. 25D is a bar graph of viral replication in lungs by plaque assay.

Figure 25E:
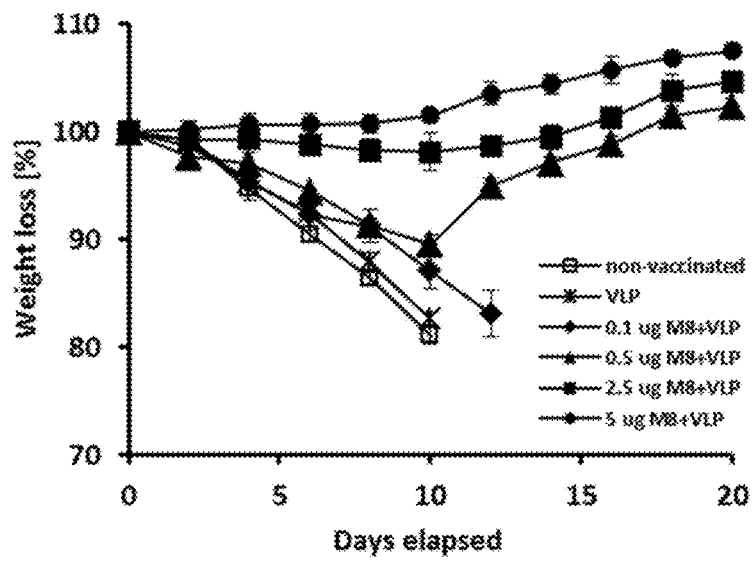

FIG. 25E is a plot of weight loss in the mice over time.

Figure 25F:
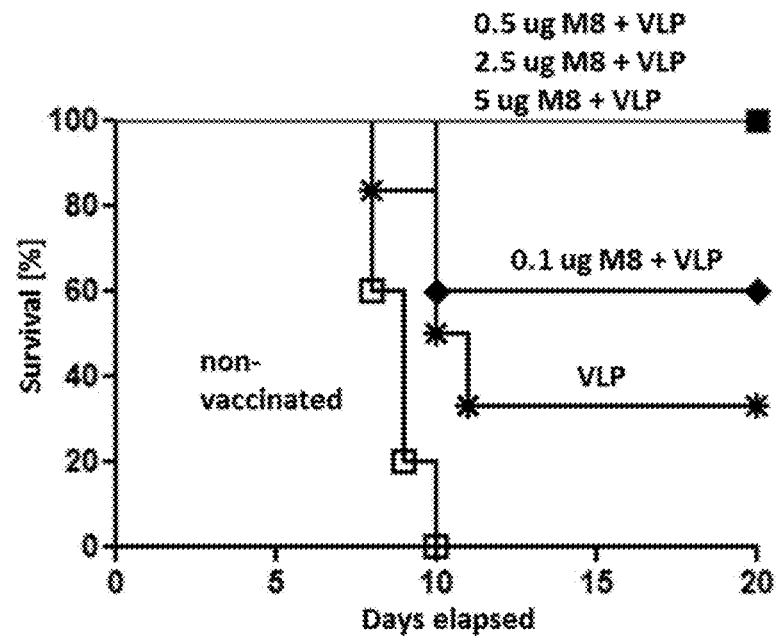

FIG. 25F is a plot of survival of the mice over time.

FIG. 26A-26D collectively show an adjuvant comparison strategy and antibody immune responses for M8, Alum, AddaVax, and poly(I:C)-adjuvanted VLP vaccine.

Figures 26A, 26B:
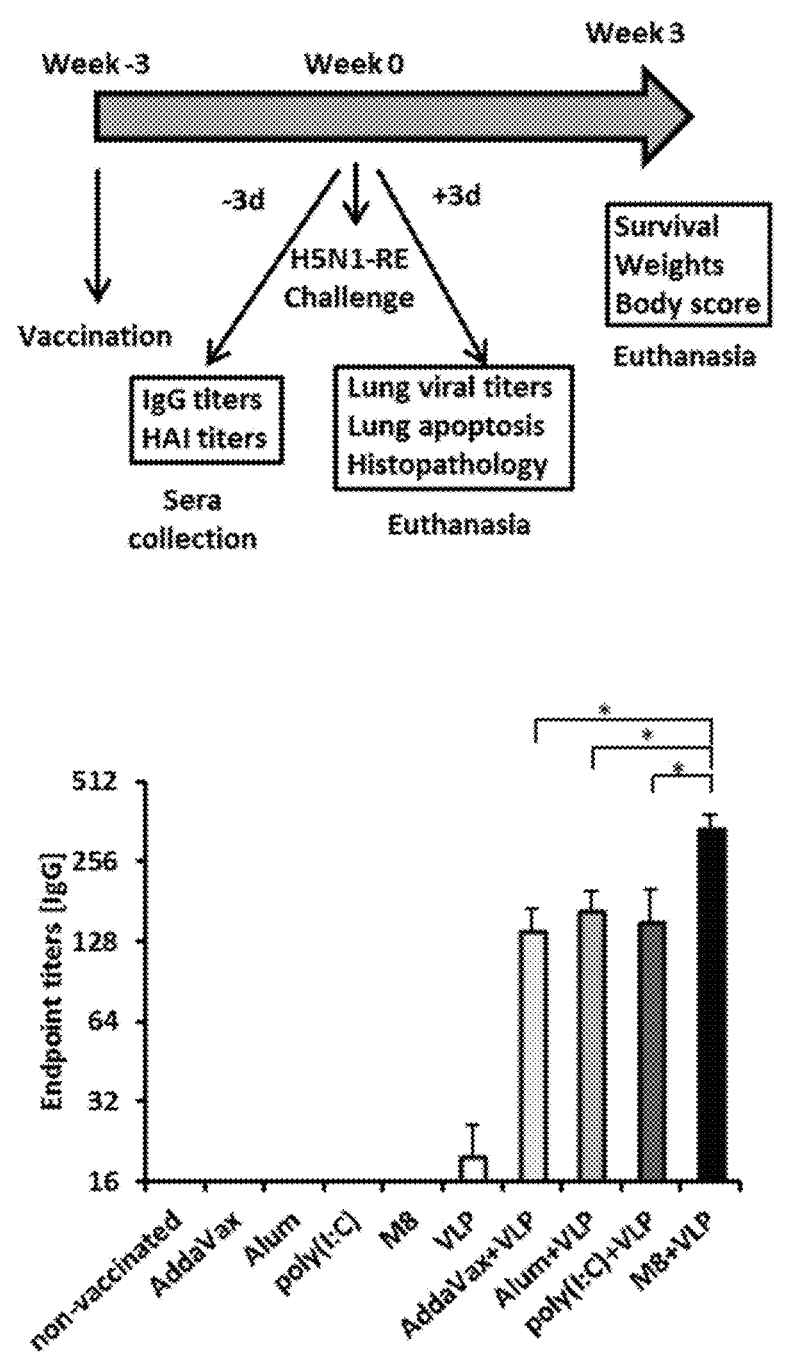

FIG. 26A is a figure describing the strategy for adjuvant comparison.

Figure 26C:
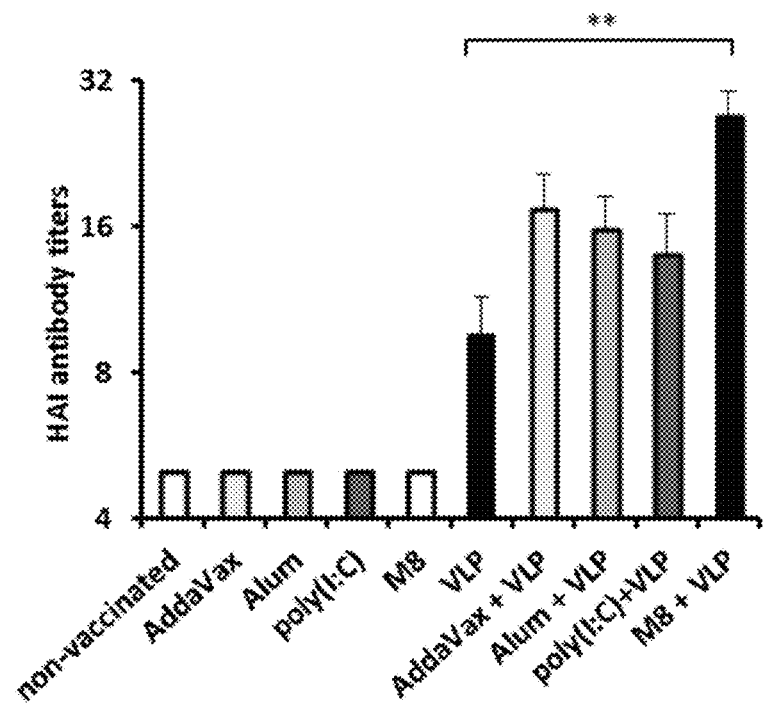
Figure 26D:
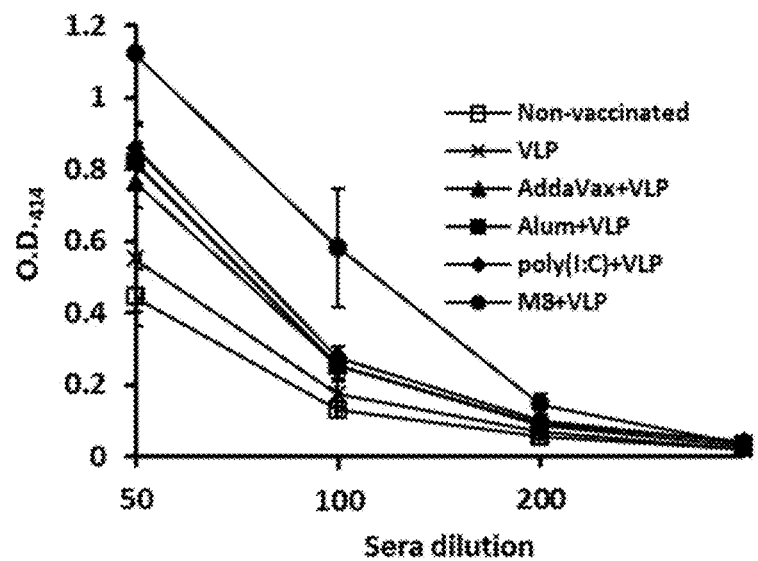

For FIGS. 26B-26D, Mice were immunized with 0.5 μg of VLP in combination with 5 μg of M8 or poly(I:C), or in combination with 50% volume of Alum or AddaVax, and five days and three weeks after immunization sera were collected.

FIG. 26B is a bar graph showing HA-specific IgG antibodies determined 3 weeks after immunization by ELISA.

FIG. 26C is a bar graph showing Influenza HAI antibody titers determined 3 weeks after immunization by HAI assay.

FIG. 26D is a plot of HA-specific IgM antibodies were determined five days after immunization by ELISA. All values are expressed as the mean±SEM. * P≤0.05;  P≤0.01; * P≤0.005; O.D., optical density; 3d, three days FIG. 27A-27D collectively show the protective efficacy of 0.5 μg of VLP in combination with 5 g of M8 or poly(I:C), or in combination with 50% volume of Alum or AddaVax. Three weeks after vaccination mice (n=8) were challenged with the lethal dose of H5N1 (5,000 pfu). All values are expressed as the mean±SEM. *** P≤0.005.

Figure 27A:
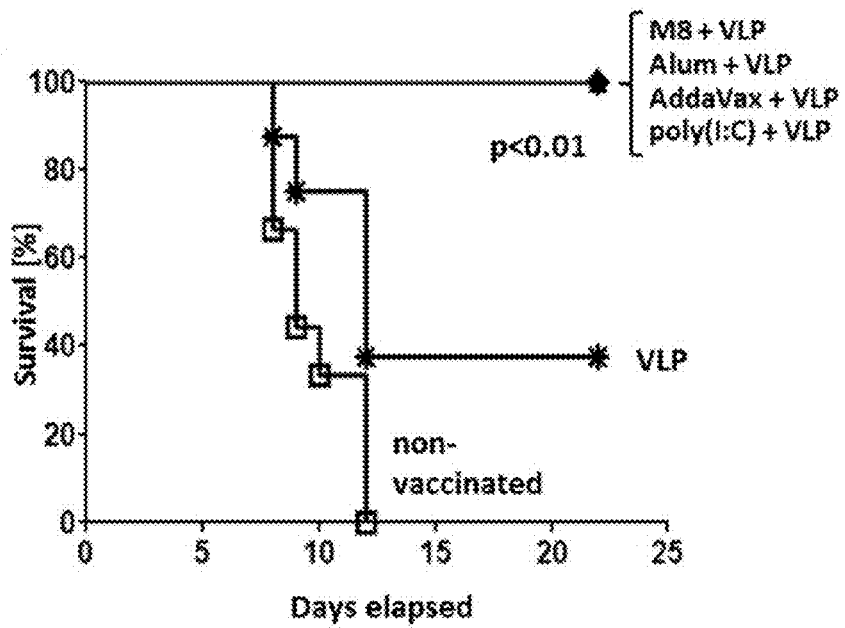

FIG. 27A is a plot showing survival.

Figure 27B:
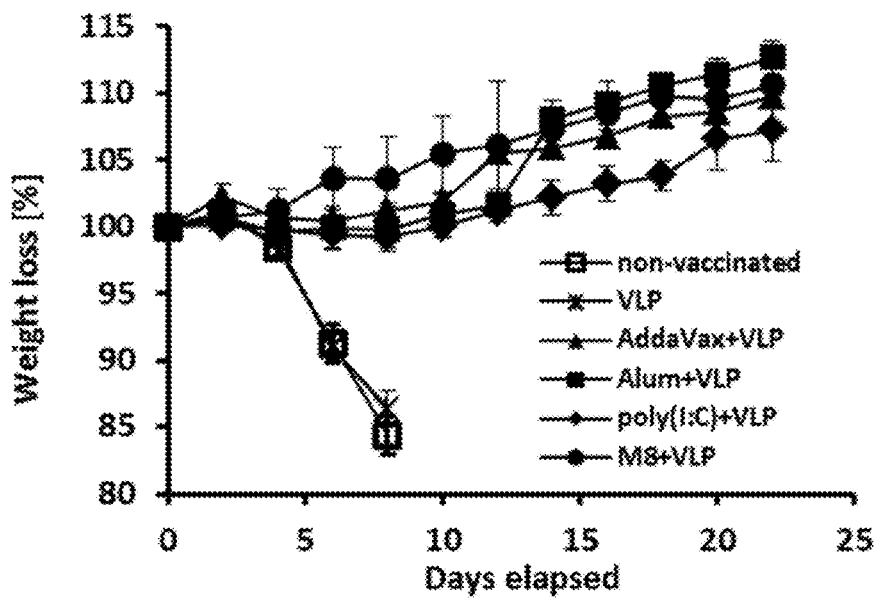

FIG. 27B is a plot showing weight.

Figure 27C:
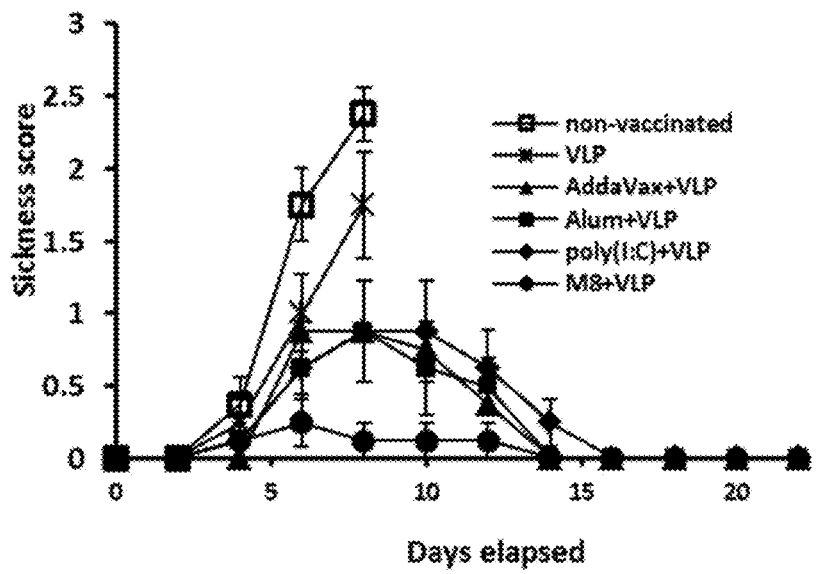

FIG. 27C is a plot showing sickness score.

Figure 27D:
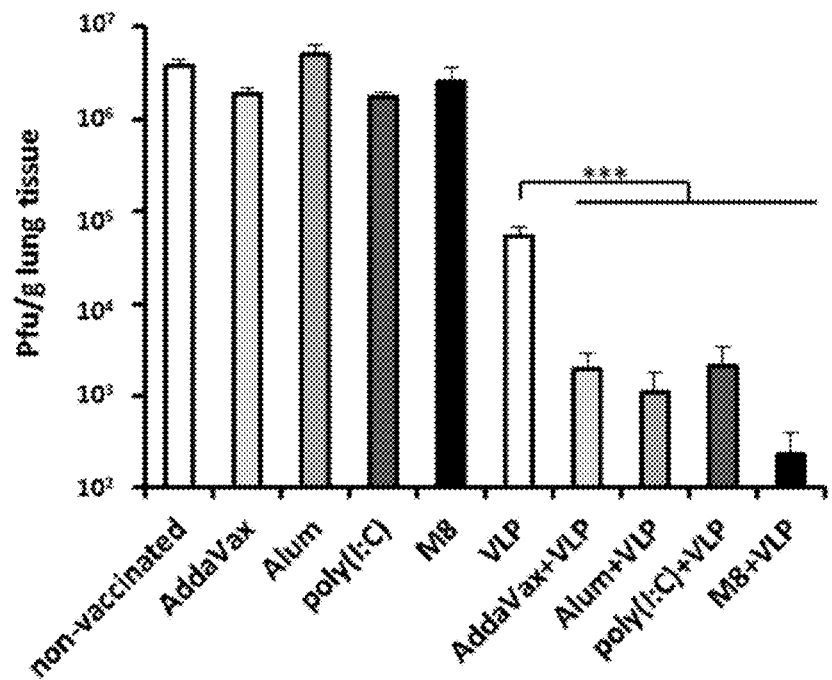

FIG. 27D is a bar graph showing viral replication in lungs was assessed by plaque assay in a separate group of immunized animals than that described above (n=5) 3 days post-infection.

FIGS. 28A-28E collectively show the long-term protective responses in mice immunized with 0.5 μg of VLP in combination with 5 μg of M8 or poly(I:C), or in combination with 50% volume of Alum or AddaVax. Mouse sera (n=8) were collected 4 (white bars) and 16 weeks (black bars) post-vaccination to determine HA-specific IgG antibodies (ELISA).

Figure 28A:
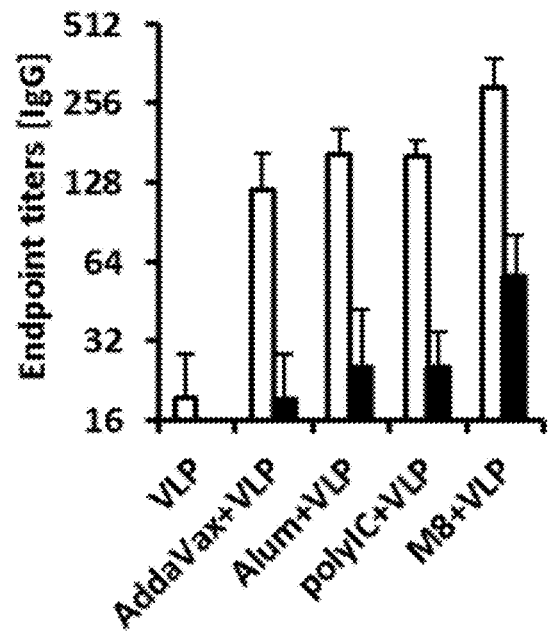

FIG. 28A is a bar graph showing HA-specific IgG antibodies by ELISA.

Figure 28B:
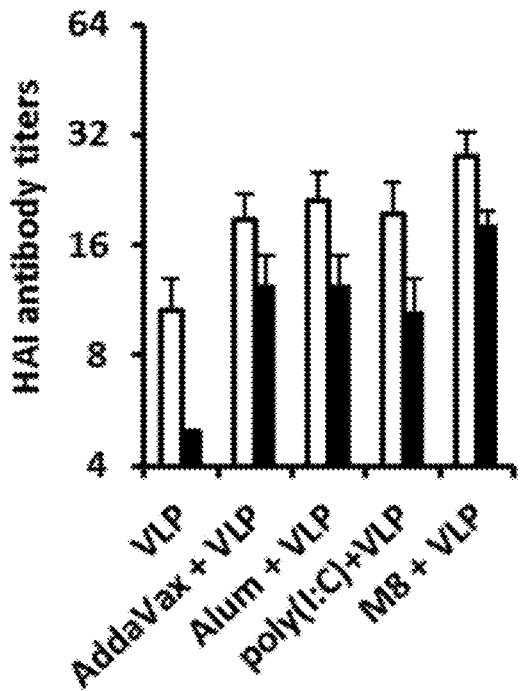

FIG. 28B is a bar graph showing HAI antibody titer by HAI assay.

Figure 28C:
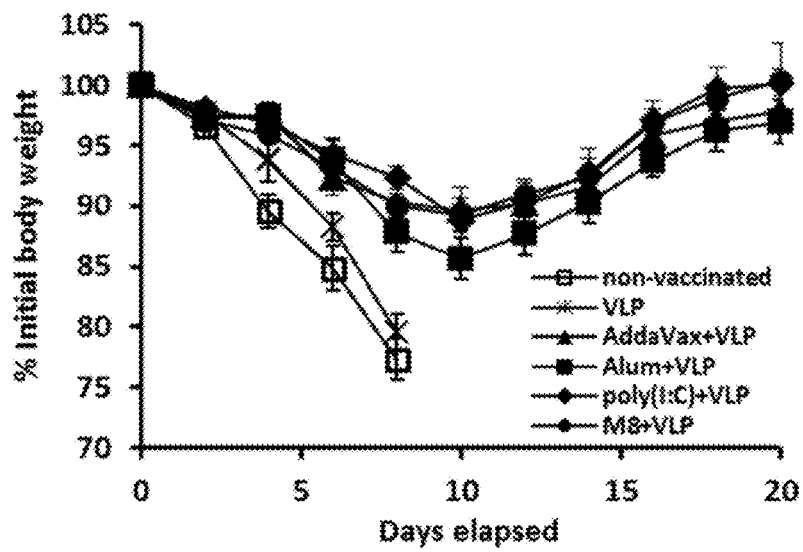

FIG. 28C is a plot showing weight of animals after challenge with a lethal H5N1 dose (5000 pfu).

Figure 28D:
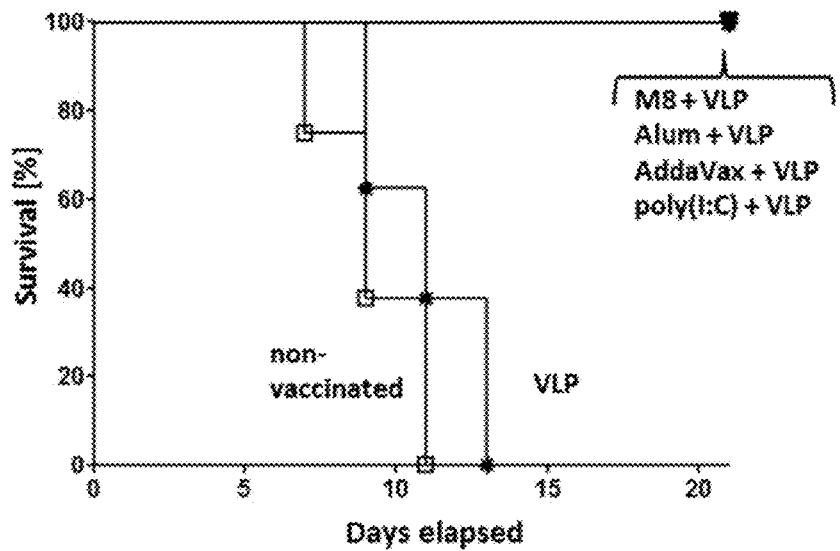

FIG. 28D is a plot showing survival of animals after challenge with a lethal H5N1 dose (5000 pfu).

FIG. 28DE is a plot showing sickness score of animals after challenge with a lethal H5N1 dose (5000 pfu.)

Figure 29A:
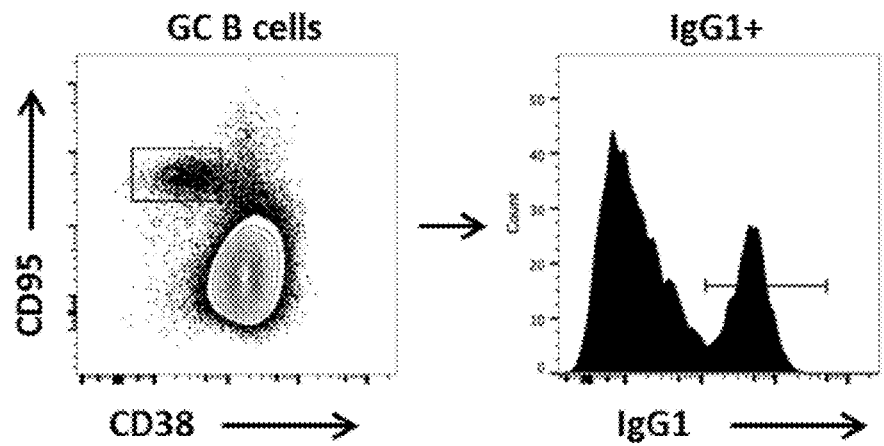
Figure 29B:
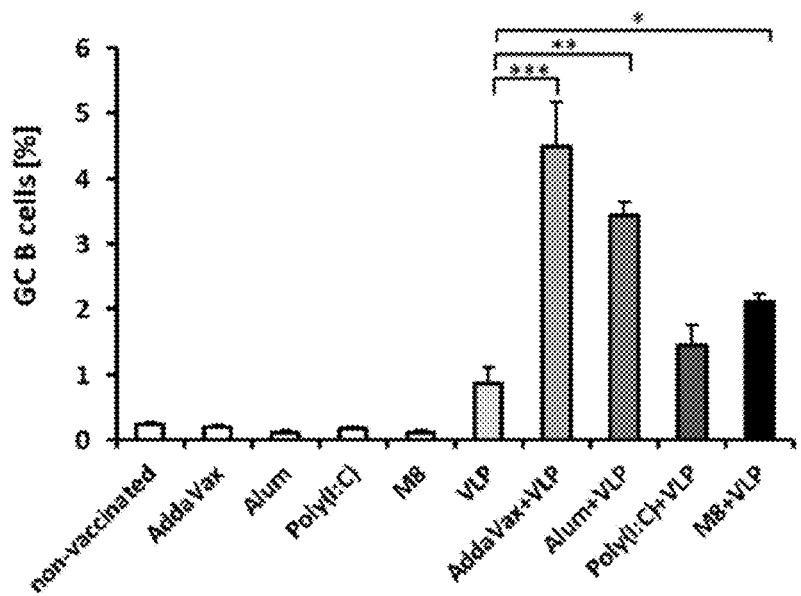
Figure 29C:
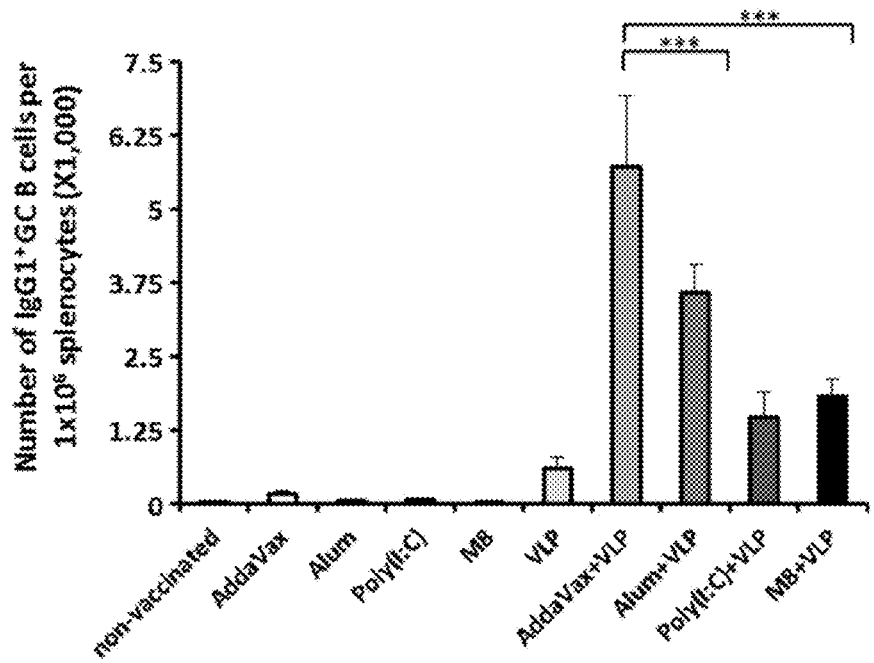

FIG. 29A-29C collectively show the quantification of germinal center (GC) B cells from spleens of IM immunized mice (n=5) by flow cytometry.

FIG. 29A illustrates the gating strategy for quantification of GC B cells.

FIG. 29B is a bar graph showing the percent GC B cells in B220$^{hi}$ splenocytes.

FIG. 29C is a bar graph showing the quantification of IgG1$^+$ GC B cells. All values are expressed as the mean±SEM. * P≤0.05;  P≤0.01; * P≤0.005.

FIG. 30A-30F collectively show the quantification of IgG subclasses from IM vaccinated animals (n=8) and intracellular cytokine levels in T cells isolated from spleens of IP vaccinated animals (n=5) after 24 h of VLP stimulation. All values are expressed as the mean±SEM. * P≤0.05;  P≤0.01; * P≤0.005

Figure 30A:
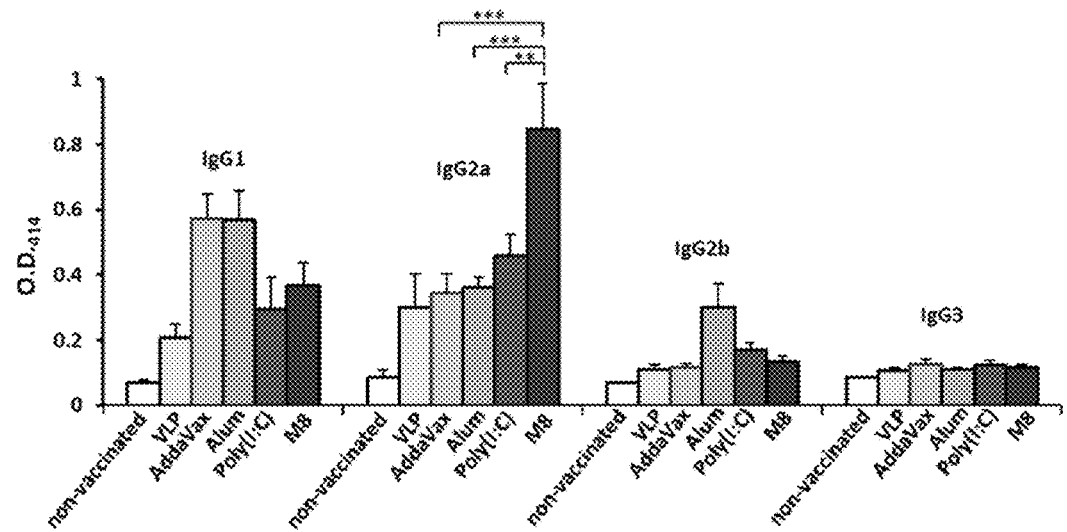

FIG. 30A is a bar graph of IgG subclasses, IgG1, IgG2a, IgG2b, and IgG3, from sera of vaccinated animals determined by ELISA using HA-coated plates.

Figure 30B:
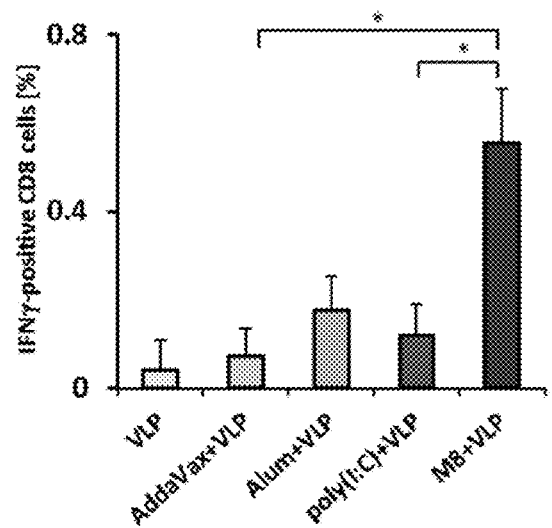

FIG. 30B is a bar graph of the percent of IFNγ$^+$ CD8$^{hi}$ cells.

Figure 30C:
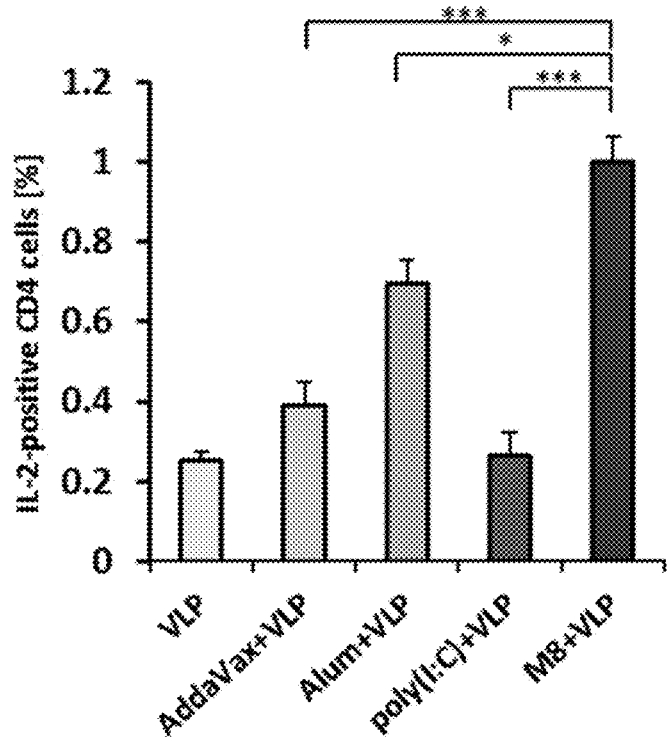

FIG. 30C is a bar graph of the percent of IL-2$^+$ CD4$^{hi}$ cells.

Figure 30D:
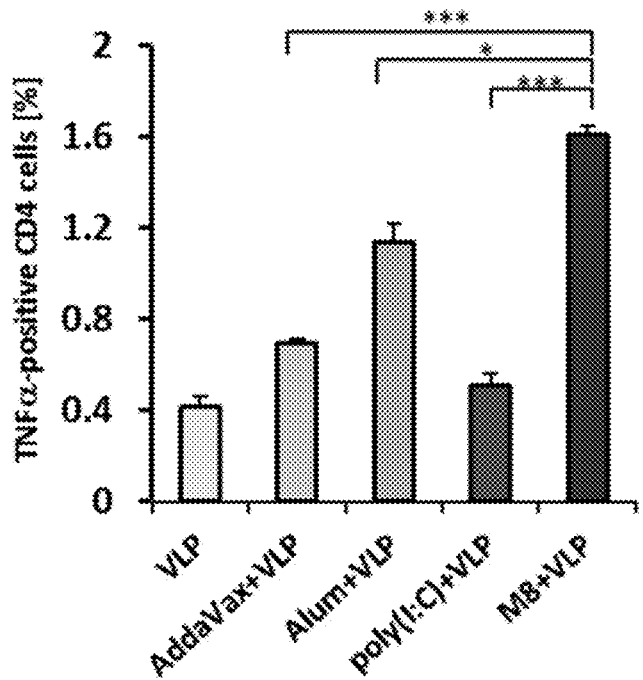

FIG. 30D is a bar graph of the percent of TNFα$^+$ CD4$^{hi}$ cells.

Figure 30E:
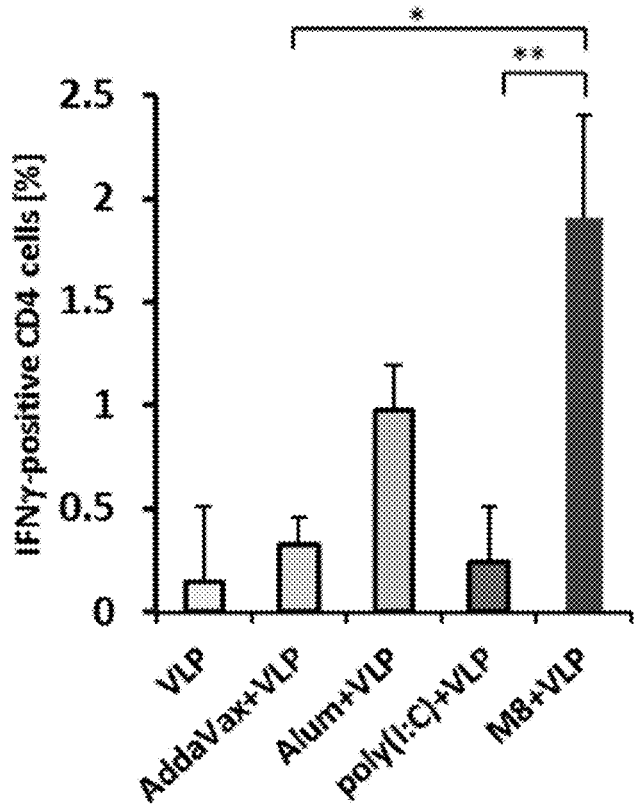

FIG. 30E is a bar graph of the percent of IFNγ$^+$ CD4$^{hi}$ cells.

Figure 30F:
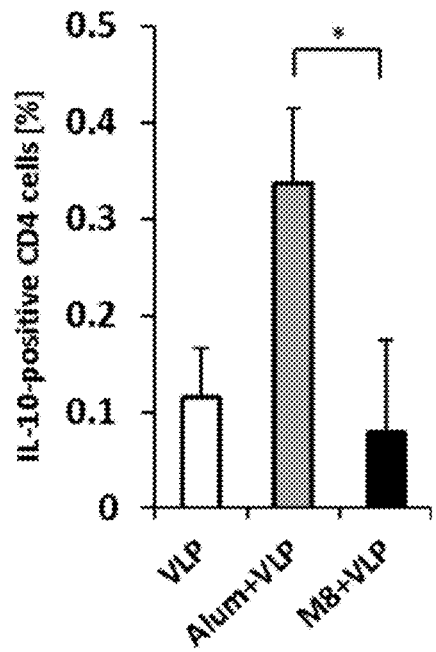

FIG. 30F is a bar graph of the percent of IL-10$^+$ CD4$^{hi}$ cells.

SEQUENCE LISTING

SEQ ID NO: 1 is a polynucleotide that makes up part of an oligoribonucleotide described herein.

SEQ ID NO: 2 is a polynucleotide that makes up part of an oligoribonucleotide described herein.

SEQ ID NO: 3 is a polynucleotide that makes up part of an oligoribonucleotide described herein.

SEQ ID NO: 4 is a polynucleotide that makes up part of an oligoribonucleotide described herein.

SEQ ID NO: 5 is an oligoribonucleotide. 5'pppSEQ ID NO: 5 is also referred to as WT (wild type) herein.

SEQ ID NO: 6 is an oligoribonucleotide. 5'pppSEQ ID NO: 6 is also referred to as M1 herein.

SEQ ID NO: 7 is an oligoribonucleotide. 5'pppSEQ ID NO: 7 is also referred to as M2 herein.

SEQ ID NO: 8 is an oligoribonucleotide. 5'pppSEQ ID NO: 8 is also referred to as M3 herein.

SEQ ID NO: 9 is an oligoribonucleotide. 5'pppSEQ ID NO: 9 is also referred to as M4 herein.

SEQ ID NO: 10 is an oligoribonucleotide. 5'pppSEQ ID NO: 10 is also referred to as M5 herein.

SEQ ID NO: 11 is an oligoribonucleotide. 5'pppSEQ ID NO: 11 is also referred to as M6 herein.

SEQ ID NO: 12 is an oligoribonucleotide. 5'pppSEQ ID NO: 12 is also referred to as M7 herein.

SEQ ID NO: 13 is an oligoribonucleotide. 5'pppSEQ ID NO: 13 is also referred to as M8 herein.

SEQ ID NO: 14 is an oligoribonucleotide. 5'pppSEQ ID NO: 14 is also referred to as M8A herein.
SEQ ID NO: 15 is an oligoribonucleotide. 5'pppSEQ ID NO: 15 is also referred to as M8B herein.
SEQ ID NO: 16 is an oligoribonucleotide. 5'pppSEQ ID NO: 16 is also referred to as M8C herein.
SEQ ID NO: 17 is an oligoribonucleotide. 5'pppSEQ ID NO: 17 is also referred to as M8D herein.
SEQ ID NO: 18 is a VSV WT forward primer.
SEQ ID NO: 19 is a VSV WT reverse primer.
SEQ ID NO: 20 is an M1 forward primer.
SEQ ID NO: 21 is an M1 reverse primer.
SEQ ID NO: 22 is an M2 forward primer.
SEQ ID NO: 23 is an M2 reverse primer.
SEQ ID NO: 24 is an M3 forward primer.
SEQ ID NO: 25 is an M3 reverse primer.
SEQ ID NO: 26 is an M4 forward primer.
SEQ ID NO: 27 is an M4 reverse primer.
SEQ ID NO: 28 is an M5 forward primer.
SEQ ID NO: 29 is an M5 reverse primer.
SEQ ID NO: 30 is an M6 forward primer.
SEQ ID NO: 31 is an M6 reverse primer.
SEQ ID NO: 32 is an M7 forward primer.
SEQ ID NO: 33 is an M7 reverse primer.
SEQ ID NO: 34 is an M8 forward primer.
SEQ ID NO: 35 is an M8 reverse primer.
SEQ ID NO: 36 is an M8A forward primer.
SEQ ID NO: 37 is an M8A reverse primer.
SEQ ID NO: 38 is an M8B forward primer.
SEQ ID NO: 39 is an M8B reverse primer.
SEQ ID NO: 40 is an M8C forward primer.
SEQ ID NO: 41 is an M8C reverse primer.
SEQ ID NO: 42 is an M8D forward primer.
SEQ ID NO: 43 is an M8D reverse primer.
SEQ ID NO: 44 is a BIRC3 forward primer.
SEQ ID NO: 45 is a BIRC3 reverse primer.
SEQ ID NO: 46 is a CCL3 forward primer.
SEQ ID NO: 47 is a CCL3 reverse primer.
SEQ ID NO: 48 is a CCL5 forward primer.
SEQ ID NO: 49 is a CCL5 reverse primer.
SEQ ID NO: 50 is a CXCL10 forward primer.
SEQ ID NO: 51 is a CXCL10 reverse primer.
SEQ ID NO: 52 is a DDX58 forward primer.
SEQ ID NO: 53 is a DDX58 reverse primer.
SEQ ID NO: 54 is a DENV2 forward primer.
SEQ ID NO: 55 is a DENV2 reverse primer.
SEQ ID NO: 56 is a GADPH forward primer.
SEQ ID NO: 57 is a GADPH reverse primer.
SEQ ID NO: 58 is an IFIT1 forward primer.
SEQ ID NO: 59 is an IFIT1 reverse primer.
SEQ ID NO: 60 is an IFIT2 forward primer.
SEQ ID NO: 61 is an IFIT2 reverse primer.
SEQ ID NO: 62 is an IFITM1 forward primer.
SEQ ID NO: 63 is an IFITM1 reverse primer.
SEQ ID NO: 64 is an IFITM2 forward primer.
SEQ ID NO: 65 is an IFITM2 reverse primer.
SEQ ID NO: 66 is an IFITM3 forward primer.
SEQ ID NO: 67 is an IFITM3 reverse primer.
SEQ ID NO: 68 is an IFNAR1 forward primer.
SEQ ID NO: 69 is an IFNAR1 reverse primer.
SEQ ID NO: 70 is an IFNAR2 forward primer.
SEQ ID NO: 71 is an IFNAR2 reverse primer.
SEQ ID NO: 72 is an IFNB1 forward primer.
SEQ ID NO: 73 is an IFNB1 reverse primer.
SEQ ID NO: 74 is an IL1A forward primer.
SEQ ID NO: 75 is an IL1A reverse primer.
SEQ ID NO: 76 is an IL1B forward primer.
SEQ ID NO: 77 is an IL1B reverse primer.
SEQ ID NO: 78 is an IL-6 forward primer.
SEQ ID NO: 79 is an IL-6 reverse primer.
SEQ ID NO: 80 is an IL-8 forward primer.
SEQ ID NO: 81 is an IL-8 reverse primer.
SEQ ID NO: 82 is an IL-10 forward primer.
SEQ ID NO: 83 is an IL-10 reverse primer.
SEQ ID NO: 84 is an IL-12A forward primer.
SEQ ID NO: 85 is an IL-12A reverse primer.
SEQ ID NO: 86 is an IL-28RA forward primer.
SEQ ID NO: 87 is an IL-28RA reverse primer.
SEQ ID NO: 88 is an IL-29 forward primer.
SEQ ID NO: 89 is an IL-29 reverse primer.
SEQ ID NO: 90 is an IRF3 forward primer.
SEQ ID NO: 91 is an IRF3 reverse primer.
SEQ ID NO: 92 is an IRF7 forward primer.
SEQ ID NO: 93 is an IRF7 reverse primer.
SEQ ID NO: 94 is an ISG15 forward primer.
SEQ ID NO: 95 is an ISG15 reverse primer.
SEQ ID NO: 96 is an MX1 forward primer.
SEQ ID NO: 97 is an MX1 reverse primer.
SEQ ID NO: 98 is an MX2 forward primer.
SEQ ID NO: 99 is an MX2 reverse primer.
SEQ ID NO: 100 is an SOCS3 forward primer.
SEQ ID NO: 101 is an SOCS3 reverse primer.
SEQ ID NO: 102 is a STAT1 forward primer.
SEQ ID NO: 103 is a STAT1 reverse primer.
SEQ ID NO: 104 is a TANK forward primer.
SEQ ID NO: 105 is a TANK reverse primer.
SEQ ID NO: 106 is a TLR3 forward primer.
SEQ ID NO: 107 is a TLR3 reverse primer.
SEQ ID NO: 108 is a TLR7 forward primer.
SEQ ID NO: 109 is a TLR7 reverse primer.
SEQ ID NO: 110 is a TNF forward primer.
SEQ ID NO: 111 is a TNF reverse primer.
SEQ ID NO: 112 is a CD40 forward primer.
SEQ ID NO: 113 is a CD40 reverse primer.
SEQ ID NO: 114 is a CD74 forward primer.
SEQ ID NO: 115 is a CD74 reverse primer.
SEQ ID NO: 116 is a CD80 forward primer.
SEQ ID NO: 117 is a CD80 reverse primer.
SEQ ID NO: 118 is a CD83 forward primer.
SEQ ID NO: 119 is a CD83 reverse primer.
SEQ ID NO: 120 is a CD86 forward primer.
SEQ ID NO: 121 is a CD86 reverse primer.
SEQ ID NO: 122 is a 4-1BB forward primer.
SEQ ID NO: 123 is a 4-1BB reverse primer.
SEQ ID NO: 124 is an HLA-DRA forward primer.
SEQ ID NO: 125 is an HLA-DRA reverse primer.
SEQ ID NO: 126 is an HLA-DQA forward primer.
SEQ ID NO: 127 is an HLA-DQA reverse primer.

DETAILED DESCRIPTION

Disclosed herein are synthetic oligoribonucleotides, each synthesized with a triphosphate group at its 5' end. The oligoribonucleotide includes: a first polynucleotide of SEQ ID NO: 1, a second polynucleotide of SEQ ID NO: 2 and a third polynucleotide of SEQ ID NO: 3 with SEQ ID NO: 3 located between SEQ ID NO: 1 and SEQ ID NO: 2. SEQ ID NO: 1 can be 5' of SEQ ID NO: 2 or SEQ ID NO: 1 can be 3' of SEQ ID NO: 2. The oligoribonucleotides can comprise any additional sequence.

In examples where SEQ ID NO: 1 is 5' of SEQ ID NO: 2, the oligoribonucleotides comprise the structure: GAC-GAAGACCACAAAACCAGAU(A)$_n$UAA(U)$_n$AUCUG-GUUUUGUGGUCUUCGUC or GACGAAGACCA- CAAAACCAGAU(U)$_n$UAA(A)$_n$AUCUGGUUUUGUGGUCUUCGUC; wherein n is any integer greater than 1. This structure indicates that the nucleotide in parentheses is repeated the number of times equal to n. For example, n can equal 2, 3, 6, 11, 16, 26, or more that 26 repeats of the nucleotide indicated in parentheses. In this example, the number of A or U nucleotides is equal.

The oligoribonucleotides can also comprise the structure: GACGAAGACCACAAAACCAGAU(AAU)$_x$U(AUU)$_y$-AUCUGGUUUUGUGGUCUUCGUC or GACGAAGAC-CACAAAACCAGAU(AUU)$_x$U(AAU)$_y$AUCUGGUUUU-GUGGUCUUCGUC; wherein x and y are any integer greater than 2. In this example the tripeptide in parentheses is repeated a number of times equal to x or y. In this example, x and y can be different numbers. For example x can equal 10 while y can equal 8.

In examples where SEQ ID NO: 1 is 3' of SEQ ID NO: 2, the oligoribonucleotides can have the structure: AUCUG-GUUUUGUGGUCUUCGUC(A)$_n$UAA(U)$_n$GAC-GAAGACCACAAAACCAGAU; or AUCUGGUUUU-GUGGUCUUCGUC(U)$_n$UAA(A)$_n$GACGAAGACCACAAAACCAGAU, wherein n is an integer greater than 1.

Alternatively, the synthetic oligoribonucleotide can be an oligoribonucleotide of at least 59 nucleotides in length that can form a hairpin structure comprising at least 29 base pairs, the synthetic oligonucleotide further comprising a triphosphate group at the 5' end of the oligoribonucleotide. In examples of these aspects, the oligoribonucleotides are at least 99 nucleotides in length that can form a hairpin structure comprising at least 49 base pairs.

The synthetic oligoribonucleotides described herein can be expressed from a DNA plasmid. Such a DNA plasmid comprises the DNA sequence that encodes the described oligoribonucleotides. The oligoribonucleotides can be transcribed as an RNA molecule that automatically folds into duplexes with hairpin loops. Typically, a transcriptional unit or cassette will contain an RNA transcript promoter sequence, such as a T7 promoter operably linked to the sequence encoding the oligoribonucleotide.

The synthetic oligoribonucleotides described herein comprise a 5'-triphosphate group. These may collectively be referred to as 5'pppRNA or individually as 5'pppSEQ ID NO: XX herein. Alternatively, individual compounds may be referred to herein by names such as WT, M5, or M8 as indicated in the Sequence Listing above.

Methods of isolating RNA, synthesizing RNA, hybridizing nucleic acids, making and screening cDNA libraries, and performing PCR are well known in the art (see, e.g., Gubler and Hoffman, *Gene* 25, 263-269 (1983); Sambrook and Russell, *Molecular Cloning: A Laboratory Manual*, Cold Spring Harbor Laboratory Press, Cold Spring Harbor N.Y., (2001)) as are PCR methods (see, U.S. Pat. Nos. 4,683,195 and 4,683,202; *PCR Protocols: A Guide to Methods and Applications*, Innis et al, Eds, (1990)). Expression libraries are also well known to those of skill in the art. Additional basic texts disclosing the general methods of use in this invention include Sambrook and Russell (2001) supra; Kriegler, *Gene Transfer and Expression: A Laboratory Manual* (1990); and *Current Protocols in Molecular Biology* (Ausubel et al., eds., 1994).

An oligoribonucleotide can also be chemically synthesized. Synthesis of the single-stranded nucleic acid makes use of common nucleic acid protecting and coupling groups, such as dimethoxytrityl at the 5'-end and phosphoramidites at the 3'-end. As a non-limiting example, small scale syntheses can be conducted on an Applied Biosystems synthesizer using a 0.2 micromolar scale protocol with a 2.5 min coupling step for 2'-O-methylated nucleotides. Alternatively, syntheses at the 0.2 micromolar scale can be performed on a 96-well plate synthesizer from Protogene. However, a larger or smaller scale of synthesis is encompassed by the invention, including any method of synthesis now known or yet to be disclosed. Suitable reagents for synthesis of the single-stranded oligonucleotides, methods of RNA deprotection, methods of RNA purification, and methods of adding phosphate groups to an oligoribonucleotide are known to those of skill in the art.

An oligoribonucleotide can be synthesized via a tandem synthesis technique, wherein both strands are synthesized as a single continuous fragment or strand separated by a linker that is subsequently cleaved to provide separate fragments or strands that hybridize to form an RNA duplex. The linker can be any linker, including a polynucleotide linker or a non-nucleotide linker. The linker can comprise any sequence of one or more ribonucleotides. The tandem synthesis of RNA can be readily adapted to both multiwell/multiplate synthesis platforms as well as large scale synthesis platforms employing batch reactors, synthesis columns, and the like.

Alternatively, the oligoribonucleotide can be assembled from two distinct single-stranded molecules, wherein one strand includes the sense strand and the other includes the antisense strand of the RNA. For example, each strand can be synthesized separately and joined together by hybridization or ligation following synthesis and/or deprotection. Either the sense or the antisense strand can contain additional nucleotides that are not complementary to one another and do not form a double stranded RNA molecule. In certain other instances, the oligoribonucleotide can be synthesized as a single continuous fragment, where the self-complementary sense and antisense regions hybridize to form an RNA duplex having a hairpin or panhandle secondary structure.

An oligoribonucleotide can comprise a duplex having two complementary strands that form a double-stranded region with least one modified nucleotide in the double-stranded region. The modified nucleotide may be on one strand or both. If the modified nucleotide is present on both strands, it may be in the same or different positions on each strand. Examples of modified nucleotides suitable for use in the present invention include, but are not limited to, ribonucleotides having a 2'-O-methyl (2'OMe), 2'-deoxy-2'-fluoro (2'F), 2'-deoxy, 5-C-methyl, 2'-O-(2-methoxyethyl) (MOE), 4'-thio, 2'-amino, or 2'-C-allyl group. Modified nucleotides having a conformation such as those described in, for example in Sanger, *Principles of Nucleic Acid Structure*, Springer-Verlag Ed. (1984), are also suitable for use in oligoribonucleotides. Other modified nucleotides include, without limitation: locked nucleic acid (LNA) nucleotides, G-clamp nucleotides, or nucleotide base analogs. LNA nucleotides include but need not be limited to 2'-O,4'-C-methylene-(D-ribofuranosyl)nucleotides), 2'-O-(2-methoxyethyl) (MOE) nucleotides, 2'-methyl-thio-ethyl nucleotides, 2'-deoxy-2'-fluoro (2'F) nucleotides, 2'-deoxy-2'-chloro (2Cl) nucleotides, and 2'-azido nucleotides. A G-clamp nucleotide refers to a modified cytosine analog wherein the modifications confer the ability to hydrogen bond both Watson-Crick and Hoogsteen faces of a complementary guanine nucleotide within a duplex (Lin et al, *J Am Chem Soc*, 120, 8531-8532 (1998)). Nucleotide base analogs include for example, C-phenyl, C-naphthyl, other aromatic derivatives, inosine, azole carboxamides, and nitroazole derivatives such as 3-nitropyrrole, 4-nitroindole, 5-nitroindole, and 6-nitroindole (Loakes, *Nucl Acids Res,* 29, 2437-2447 (2001)).

An oligoribonucleoitde can comprise one or more chemical modifications such as terminal cap moieties, phosphate backbone modifications, and the like. Examples of classes of terminal cap moieties include, without limitation, inverted deoxy abasic residues, glyceryl modifications, 4',5'-methylene nucleotides, 1-(β-D-erythrofuranosyl) nucleotides, 4'-thio nucleotides, carbocyclic nucleotides, 1,5-anhydrohexitol nucleotides, L-nucleotides, α-nucleotides, modified base nucleotides, threo pentofuranosyl nucleotides, acyclic 3',4'-seco nucleotides, acyclic 3,4-dihydroxybutyl nucleotides, acyclic 3,5-dihydroxypentyl nucleotides, 3'-3'-inverted nucleotide moieties, 3'-3'-inverted abasic moieties, 3'-2'-inverted nucleotide moieties, 3'-2'-inverted abasic moieties, 5'-5'-inverted nucleotide moieties, 5'-5'-inverted abasic moieties, 3'-5'-inverted deoxy abasic moieties, 5'-aminoalkyl phosphate, 1,3-diamino-2-propyl phosphate, 3 aminopropyl phosphate, 6-aminohexyl phosphate, 1,2-aminododecyl phosphate, hydroxypropyl phosphate, 1,4-butanediol phosphate, 3'-phosphoramidate, 5' phosphoramidate, hexylphosphate, aminohexyl phosphate, 3'-phosphate, 5'-amino, 3'-phosphorothioate, 5'-phosphorothioate, phosphorodithioate, and bridging or non-bridging methylphosphonate or 5'-mercapto moieties (see, e.g., U.S. Pat. No. 5,998,203; Beaucage et al, *Tetrahedron* 49, 1925 (1993)). Non-limiting examples of phosphate backbone modifications (i.e., resulting in modified internucleotide linkages) include phosphorothioate, phosphorodithioate, methylphosphonate, phosphotriester, morpholino, amidate, carbamate, carboxymethyl, acetamidate, polyamide, sulfonate, sulfonamide, sulfamate, formacetal, thioformacetal, and alkylsilyl substitutions (see, e.g., Hunziker et al, *Modern Synthetic Methods,* VCH, 331-417 (1995); Mesmaeker et al, *Antisense Research, ACS,* 24-39 (1994)). Such chemical modifications can occur at the 5'-end and/or 3'-end of the sense strand, antisense strand, or both strands of the oligoribonucleotide.

The sense and/or antisense strand of an oligoribonucleotide may comprise a 3'-terminal overhang having 1 to 4 or more 2'-deoxyribonucleotides and/or any combination of modified and unmodified nucleotides. Additional examples of modified nucleotides and types of chemical modifications that can be introduced into the modified oligoribonucleotides of the present invention are described, e.g., in UK Patent No. GB 2,397,818 B and U.S. Patent Publication Nos. 20040192626 and 20050282188.

An oligoribonucleotide may comprise one or more non-nucleotides in one or both strands of the siRNA. A non-nucleotide can be any subunit, functional group, or other molecular entity capable of being incorporated into a nucleic acid chain in the place of one or more nucleotide units that is not or does not comprise a commonly recognized nucleotide base such as adenosine, guanine, cytosine, uracil, or thymine, such as a sugar or phosphate.

Chemical modification of the disclosed oligoribonucleotides may also comprise attaching a conjugate to the oligoribonucleotide molecule. The conjugate can be attached at the 5'- and/or the 3'-end of the sense and/or the antisense strand of the oligoribonucleotide via a covalent attachment such as a nucleic acid or non-nucleic acid linker. The conjugate can also be attached to the oligoribonucleotide through a carbamate group or other linking group (see, e.g., U.S. Patent Publication Nos. 20050074771, 20050043219, and 20050158727). A conjugate may be added to the oligoribonucleotide for any of a number of purposes. For example, the conjugate may be a molecular entity that facilitates the delivery of the oligoribonucleotide into a cell or the conjugate a molecule that comprises a drug or label.

Examples of conjugate molecules suitable for attachment to the disclosed oligoribonucleotides include, without limitation, steroids such as cholesterol, glycols such as polyethylene glycol (PEG), human serum albumin (HSA), fatty acids, carotenoids, terpenes, bile acids, folates (e.g., folic acid, folate analogs and derivatives thereof), sugars (e.g., galactose, galactosamine, N-acetyl galactosamine, glucose, mannose, fructose, fucose, etc.), phospholipids, peptides, ligands for cellular receptors capable of mediating cellular uptake, and combinations thereof (see, e.g., U.S. Patent Publication Nos. 20030130186, 20040110296, and 20040249178; U.S. Pat. No. 6,753,423). Other examples include the lipophilic moiety, vitamin, polymer, peptide, protein, nucleic acid, small molecule, oligosaccharide, carbohydrate cluster, intercalator, minor groove binder, cleaving agent, and cross-linking agent conjugate molecules described in U.S. Patent Publication Nos. 20050119470 and 20050107325. Other examples include the 2'-O-alkyl amine, 2'-O-alkoxyalkyl amine, polyamine, C5-cationic modified pyrimidine, cationic peptide, guanidinium group, amidininium group, cationic amino acid conjugate molecules described in U.S. Patent Publication No. 20050153337. Additional examples of conjugate molecules include a hydrophobic group, a membrane active compound, a cell penetrating compound, a cell targeting signal, an interaction modifier, or a steric stabilizer as described in U.S. Patent Publication No. 20040167090. Further examples include the conjugate molecules described in U.S. Patent Publication No. 20050239739.

The type of conjugate used and the extent of conjugation to the disclosed oligoribonucleotides can be evaluated for improved pharmacokinetic profiles, bioavailability, and/or stability of the oligoribonucleotide while retaining activity. As such, one skilled in the art can screen oligoribonucleotides having various conjugates attached thereto to identify oligonucleotide conjugates having improved properties using any of a variety of well-known in vitro cell culture or in vivo animal models.

Pharmaceutical Compositions

An oligoribonucleotide may be incorporated into a pharmaceutically acceptable carrier or transfection reagent containing the oligoribonucleotides described herein. The carrier system may be a lipid-based carrier system such as a stabilized nucleic acid-lipid particle (e.g., SNALP or SPLP), cationic lipid or liposome nucleic acid complexes (i.e., lipoplexes), a liposome, a micelle, a virosome, or a mixture thereof. In other embodiments, the carrier system is a polymer-based carrier system such as a cationic polymer-nucleic acid complex (i.e., polyplex). In additional embodiments, the carrier system is a cyclodextrin-based carrier system such as a cyclodextrin polymer-nucleic acid complex (see US Patent Application Publication 20070218122). In further embodiments, the carrier system is a protein-based carrier system such as a cationic peptide-nucleic acid complex. An oligoribonucleotide molecule may also be delivered as naked RNA.

A pharmaceutical composition can be any combination of active and/or inert materials that can be administered to a subject for the purpose of treating a disease. A pharmaceutically acceptable carrier (interchangeably termed a vehicle) can be any material or molecular entity that facilitates the administration or other delivery of the pharmaceutical composition. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle.

A pharmaceutical composition can comprise an adjuvant. An adjuvant can be any compound, composition, or substance that when used in combination with an immunogenic agent augments or otherwise alters or modifies a resultant immune response. In some examples, an adjuvant increases the titer of antibodies induced in a subject by the immunogenic agent. In another example, if the antigenic agent is a multivalent antigenic agent, an adjuvant alters the particular epitopic sequences that are specifically bound by antibodies induced in a subject. In some examples, the oligoribonucleotides are added to an immunogenic agent (such as H5N1 virus-like particles) to act as an adjuvant.

Other agents that can be used as adjuvants in formulating pharmaceutical compositions used to produce an immune response include Freund's Incomplete Adjuvant (IFA), Freund's complete adjuvant, B30-MDP, LA-15-PH, montanide, saponin, aluminum salts such as aluminum hydroxide (Amphogel, Wyeth Laboratories, Madison, N.J.), alum, lipids, the MF59 microemulsion, a mycobacterial antigen, vitamin E, non-ionic block polymers, muramyl dipeptides, polyanions, amphipatic substances, ISCOMs (immune stimulating complexes, such as those disclosed in European Patent EP 109942), vegetable oil, Carbopol, aluminium oxide, oil-emulsions (such as Bayol F or Marcol 52), *E. coli* heat-labile toxin (LT), Cholera toxin (CT), and combinations thereof. Such adjuvants can be formulated with the disclosed oligoribonucleotides.

A pharmaceutical composition comprising an immunogenic protein and an adjuvant can also be termed a vaccine. In some examples, the immunogenic protein is a virus like particle. Virus-like particles (VLPs) are vaccine platforms composed of viral proteins that spontaneously assemble, mimicking the live virus but lacking genetic material and therefore without the ability to replicate. Merck's human papilloma virus (HPV) vaccine Gardasil® is a quadrivalent HPV VLP vaccine that prevents infection by HPV types 6, 11, 16, and 18, and contains Alum as adjuvant.

A therapeutically effective amount or concentration of a compound such as the disclosed oligoribonucleotides may be any amount of a composition that alone, or together with one or more additional therapeutic agents, is sufficient to achieve a desired effect in a subject. The effective amount of the agent will be dependent on several factors, including, but not limited to, the subject being treated and the manner of administration of the therapeutic composition. In one example, a therapeutically effective amount or concentration is one that is sufficient to prevent advancement, delay progression, or to cause regression of a disease, or which is capable of reducing symptoms caused by any disease, including viral infection.

In one example, a desired effect is to reduce or inhibit one or more symptoms associated with viral infection. The one or more symptoms do not have to be completely eliminated for the composition to be effective. For example, a composition can decrease the sign or symptom by a desired amount, for example by at least 20%, at least 50%, at least 80%, at least 90%, at least 95%, at least 98%, or even at least 100%, as compared to the sign or symptom in the absence of the composition.

A therapeutically effective amount of a pharmaceutical composition can be administered in a single dose, or in several doses, for example daily, during a course of treatment. However, the therapeutically effective amount can depend on the subject being treated, the severity and type of the condition being treated, and the manner of administration. For example, a therapeutically effective amount of such agent can vary from about 100 μg-10 mg per kg body weight if administered intravenously.

The actual dosages will vary according to factors such as the type of virus to be protected against and the particular status of the subject (for example, the subject's age, size, fitness, extent of symptoms, susceptibility factors, and the like) time and route of administration, other drugs or treatments being administered concurrently, as well as the specific pharmacology of treatments for viral infection for eliciting the desired activity or biological response in the subject. Dosage regimens can be adjusted to provide an optimum prophylactic or therapeutic response.

A therapeutically effective amount is also one in which any toxic or detrimental side effects of the compound and/or other biologically active agent is outweighed in clinical terms by therapeutically beneficial effects. A non-limiting range for a therapeutically effective amount of treatments for viral infection within the methods and formulations of the disclosure is about 0.0001 μg/kg body weight to about 10 mg/kg body weight per dose, such as about 0.0001 μg/kg body weight to about 0.001 μg/kg body weight per dose, about 0.001 μg/kg body weight to about 0.01 μg/kg body weight per dose, about 0.01 μg/kg body weight to about 0.1 μg/kg body weight per dose, about 0.1 μg/kg body weight to about 10 μg/kg body weight per dose, about 1 μg/kg body weight to about 100 μg/kg body weight per dose, about 100 μg/kg body weight to about 500 μg/kg body weight per dose, about 500 μg/kg body weight per dose to about 1000 μg/kg body weight per dose, or about 1.0 mg/kg body weight to about 10 mg/kg body weight per dose.

Dosage can be varied by the attending clinician to maintain a desired concentration. Higher or lower concentrations can be selected based on the mode of delivery, for example, trans-epidermal, rectal, oral, pulmonary, intranasal delivery, intravenous or subcutaneous delivery.

Determination of effective amount is typically based on animal model studies followed up by human clinical trials and is guided by administration protocols that significantly reduce the occurrence or severity of targeted disease symptoms or conditions in the subject. Suitable models in this regard include, for example, murine, rat, porcine, feline, non-human primate, and other accepted animal model subjects known in the art. Alternatively, effective dosages can be determined using in vitro models (for example, viral titer assays or cell culture infection assays). Using such models, only ordinary calculations and adjustments are required to determine an appropriate concentration and dose to administer a therapeutically effective amount of the treatments for viral infection (for example, amounts that are effective to alleviate one or more symptoms of viral infection).

Methods of Treating Viral Infections

Disclosed herein are methods of treating a subject that has or may have a viral infection comprising administering a pharmaceutical composition comprising the disclosed oligoribonucleotides to the subject. The subject may be treated therapeutically or prophylactically.

A subject can be any multi-cellular vertebrate organisms, a category that includes human and non-human mammals, such as mice. In some examples a subject is a male. In some examples a subject is a female. Further types of subjects to which the pharmaceutical composition may be properly administered include subjects known to have a viral infection (through, for example, a molecular diagnostic test or clinical diagnosis) subjects having a predisposition to contracting a viral infection (for example by living in or travelling to a region in which one or more viruses is endemic), or subjects displaying one or more symptoms of having a viral infection.

Administration of a pharmaceutical composition may be any method of providing or give a subject a pharmaceutical composition comprising the disclosed oligoribonucleotides, by any effective route. Exemplary routes of administration include, but are not limited to, injection (such as subcutaneous, intramuscular, intradermal, intraperitoneal, and intravenous), oral, sublingual, rectal, transdermal, intranasal, vaginal and inhalation routes.

Treating a subject can include any intervention that ameliorates a sign or symptom of a disease or pathological condition after it has begun to develop, whether or not the subject has developed symptoms of the disease. Ameliorating, with reference to a disease, pathological condition or symptom refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the memory and/or cognitive function of the subject, a qualitative improvement in symptoms observed by a clinician or reported by a patient, or by other parameters well known in the art that are specific to viral infections generally or specific viral infections.

A symptom can be any subjective evidence of disease or of a subject's condition, for example, such evidence as perceived by the subject; a noticeable change in a subject's condition indicative of some bodily or mental state. A sign may be any abnormality indicative of disease, discoverable on examination or assessment of a subject. A sign is generally an objective indication of disease.

The administration of a pharmaceutical composition comprising the disclosed oligoribonucleotides can be for prophylactic or therapeutic purposes. When provided prophylactically, the treatments are provided in advance of any clinical symptom of viral infection. Prophylactic administration serves to prevent or ameliorate any subsequent disease process. When provided therapeutically, the compounds are provided at (or shortly after) the onset of a symptom of disease. For prophylactic and therapeutic purposes, the treatments can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the treatments for viral infection can be provided as repeated doses within a prolonged prophylaxis or treatment regimen that will yield clinically significant results to alleviate one or more symptoms or detectable conditions associated with viral infection.

In some examples of prophylactic administration of the pharmaceutical composition, the pharmaceutical composition is administered as a vaccine comprising one or more infectious disease specific antigens in order to induce immunological memory against the one or more infectious disease organisms from which the infectious disease specific antigens were derived. The immunological memory in turn provides the subject with immunity from future infection from those infectious disease organisms such that disease from those infectious disease organisms is prevented or lessened.

Suitable methods, materials, and examples used in the practice and/or testing of embodiments of the disclosed invention are described below. Such methods and materials are illustrative only and are not intended to be limiting. Other methods, materials, and examples similar or equivalent to those described herein can be used.

EXAMPLES

The following examples are illustrative of disclosed methods. In light of this disclosure, those of skill in the art will recognize that variations of these examples and other examples of the disclosed method would be possible without undue experimentation.

Example 1

Materials and Methods

In vitro transcription and gel analysis: RIG-I agonists were synthesized by designing complementary primers with a T7 promoter (Integrated DNA Technologies), annealing them, then synthesizing with an in vitro transcription kit (Ambion) for 16 hours. RNA transcripts were DNase digested for 15 minutes at 37° C. then purified with an miRNeasy® kit (Qiagen). RNA was analyzed on a denaturing 15% TBE-urea polyacrylamide gel (Bio-Rad) following digestion with 50 ng/µl of RNase A (Ambion) or 100 mU/µl of DNase I (Ambion) for 30 minutes. Control wild type RNA is the dephosphorylated form of the WT sequence SEQ ID NO: 5 purchased from IDT.

Cell culture, transfections, and luciferase assays: Lung epithelial A549 cells were grown in F12K (ATCC) supplemented with 10% FBS (Access Cell Culture). Transfection of RNA and siRNA were performed with Lipofectamine RNAiMax® (Invitrogen) for 18-24 hours and 48 hours, respectively. Poly (I:C) LMW was purchased from Invivogen. For siRNA knockdown, A549 cells were transfected with 30 pmol of human RIG-I (sc-61480), TLR3 (sc-36685), MDA5 (sc-61010), or control siRNA (sc-37007) (Santa Cruz Biotechnologies) using Lipofectamine RNAiMax® according to the manufacturer's guidelines. For luciferase assay, 200 ng IFN-β/pGL3 and 100 ng pRL-TK plasmids were co-transfected with 5'pppRNA using Lipofectamine RNAiMax® for 24 h. Reporter gene activity was measured by Dual-Luciferase Reporter Assay (Promega) according to the manufacturer's instructions. Relative luciferase activity was measured as fold induction.

Monocyte isolation and differentiation into monocyte-derived dendritic cells: Human peripheral blood mononuclear cells (PBMC) were isolated from buffy coats of healthy, seronegative volunteers in a study approved by the IRB and by the VGTI-FL Institutional Biosafety Committee (2011-6-JH1). Written informed consent approved by the VGTI-FL Inc. ethics review board (FWA#161) was provided to study participants. Research conformed to ethical guidelines established by the ethics committee of the OHSU VGTI and Martin Health System. Briefly, PBMC were isolated from freshly collected blood using the Ficoll-Paque™ PLUS medium (GE Healthcare Bio) as per manufacturer's instructions. CD14$^+$ monocytes were isolated by positive selection using CD14 microbeads and a magnetic cells separator as per kit instructions (Miltenyi Biotech).

Purified CD14+ monocytes were cultured for 7 days in 100 mm dishes (15×10⁶ cells) in 10 mL of complete monocyte differentiation medium (Miltenyi Biotech). On day 3, the medium was replenished with fresh medium.

Quantitative real-time RT-PCR: Total RNA was isolated from cells using an RNeasy® kit (Qiagen) according to the manufacturer's instructions. RNA was reverse transcribed using the SuperScript® VILO cDNA synthesis kit (Invitrogen) according to the manufacturer's instructions. PCR primers were designed using Roche's Universal Probe Library Assay Design Center (www.universalprobelibrary.com.) Quantitative RT-PCR was performed on a LightCycler® 480 Probes Master (Roche.) All data are presented as a relative quantification with efficiency correction based on the relative expression of target gene versus GAPDH as the invariant control. Primers and probes are described in the attached Sequence Listing.

Immunoblot analyses: Whole cell extracts were separated in 4-20% acrylamide Mini-Protean® TGX precast gels (Bio-Rad) by SDS-PAGE and transferred to an Immobilon-P$^{SQ}$ PVDF membrane (Millipore) for 1 hour at 100V in a buffer containing 30 mM Tris, 200 mM glycine and 20% methanol. Membranes were blocked for 1 hour at room temperature in blocking buffer (Odyssey) then probed with the following primary antibodies: anti-RIG-I (EMD Millipore), anti-IFIT1 (Thermo Fisher Scientific), anti-pSTAT1 (Cell Signaling), anti-STAT1 (Cell Signaling), anti-pIRF3 S396 (Cell Signaling), anti-IRF3 (Cell Signaling), anti-β-actin (Odyssey), or anti-NS1.

Antibody signals were detected by immunofluorescence using the IRDye® 800CW and IRDye 680RD secondary antibodies (Odyssey) and the LI-COR imager (Odyssey.)

Flow cytometry analysis: Percentage of dengue-infected cells was determined by standard intracellular staining (ICS) using a mouse IgG2a mAb, specific for dengue E protein (clone 4G2) followed by staining with a secondary anti-mouse antibody coupled to PE (Biolegend). Prior to surface staining of dendritic cell maturation markers, MDDCs were stained for 5 minutes with human TruStain FcX (Biolegend) followed by staining with CD83-PE (Biolegend), CD86-Pacific Blue (Biolegend), or CCR7-PE Cy5 (Biolegend) for 15 minutes at 4° C. Cells were analyzed on an LSRII® flow cytometer (Becton Dickinson). Calculations and population analyses were done using FACS Diva software.

Virus Production and infection: Dengue serotype 2 strain New Guinea C (NGC) was used to infect confluent monolayers of C6/36 insect cells at an MOI of 0.5. Virus was allowed to adsorb for 1 hour at 28° C. in serum-free DMEM. Serum-free DMEM was used to wash the monolayer then replaced with DMEM/2% FBS. After 7 days of infection, the medium was harvested, cleared by centrifugation (1100 g, 10 min), and the supernatant was concentrated by centrifugation (1100 g) through a 15 ml Amicon® Centrifugal Filter Unit (Millipore). The virus was concentrated by ultracentrifugation on a sucrose density gradient (20% sucrose cushion) using a Sorvall® WX 100 Ultracentrifuge (ThermoScientific) for 2 hours at 134,000 g, 10° C. and the brake turned off. Concentrated virus was then washed to remove sucrose using a 15 ml Amicon® tube. After 2 washes, the virus was resuspended in DMEM/0.1% BSA. Titers of dengue stocks were determined by FACS, after infecting Vero cells by immunofluorescent staining of intracellular dengue E protein 24 hours post infection. For dengue challenge experiments, A549 cells were infected using dengue at an MOI of 0.5 in serum free F12K for 1 hour at 37° C. Medium was replaced with complete medium for 24 h prior to analysis. All procedures with live dengue were performed in a biosafety level 2+ facility at the Vaccine and Gene Therapy Institute-Florida.

Influenza H1N1 strain A/Puerto Rico/8/34 was amplified in Madin-Darby canine kidney (MDCK) cells and virus titer was determined by standard plaque assay. Cells were infected in 1 ml medium without FBS for 1 hour at 37° C. Inoculum was aspirated and cells were incubated with complete medium for 24 hours, prior to analysis. For viral infections, supernatants containing soluble factors induced following 5'pppRNA treatment was removed and kept aside during infection. Cells were washed once with PBS and infected in a small volume of medium without FBS for 1 h at 37° C.; then supernatant was added back for the indicated period of time. Procedures with live influenza H1N1 strain A/Puerto Rico/8/34 were performed at McGill University in a biosafety level 2+ facility.

Influenza reassortant H5N1 virus (H5N1-PR8) was generated using hemagglutinin (HA) and neuraminidase (NA) genes were derived from the H5N1 virus (HA from influenza A/Vietnam/1203/2004 and NA from influenza A/Thailand/1(KAN-1)/2004). The internal viral proteins were derived from the A/Puerto Rico/8/1934 (PR8) mouse adapted influenza A virus. The propagation of the H5N1-PR8 reassortant viruses was performed using MDCK cells. Anesthetized female BALB/c mice were infected intranasally with the lethal dose (5×10³ PFU in 50 μL PBS) of the H5N1-PR8. All procedures with influenza reassortant H5N1-PR8 were performed in a biosafety level 2+ facility at the Vaccine and Gene Therapy Institute-Florida.

Virus Like particle (VLP) vaccine: The H5N1-PR8 VLP were purified from HEK 293 T cells which were transfected using Lipofectamine2000® (Invitrogen) with 5 μg of each plasmid DNA expressing H5N1 A/Vietnam/1203/2004 HA and H5N1 A/Thailand/1(KAN-1)/2004 NA (codon optimized); and 10 μg of plasmid DNA expressing HIV gag. Cells were incubated for 72 h at 37° C. and supernatants containing VLPs were collected, sterile filtered and VLP were purified by centrifugation at 100,000×g through a 20% glycerol cushion and resuspended in PBS. Total protein was quantified using BCA protein assay (Thermo Fisher Scientific) and VLPs were aliquoted in PBS and stored at −80° C.

Sickness score: The sickness score was generated by evaluation of animal activity, hunched back, and ruffled fur. The final score was the addition of each individual score resulting in the minimum score 0 for a healthy mouse and 1-4 for a sick mouse.

In vivo administration of 5'pppRNA and influenza infection model: BALB/c mice (6-8 weeks of age, Jackson Laboratories) were housed in cage units, fed ad libitum, and cared for under USDA guidelines for laboratory animals. For vaccination, mice were anesthetized with IsoSol® (Patterson Veterinary) and vaccinated via the intramuscular route with 3 μg (based on HA content) of purified VLP (in 50 μl PBS) with or without 25 μg 5'pppRNA as adjuvant and then challenged or boosted with the same dose at week 3 with the identical vaccine formulation. The 5'pppRNA was complexed with in vivo-jetPEI® (PolyPlus, France) at an N/P ratio of 8 according to the manufacturer instructions. Animals were monitored for survival and morbidity (weight loss, ruffling fur, hunched back, lethargy) weekly during the vaccination regimen and each day during the viral challenge. Blood samples for serological analysis were collected from anesthetized mice via retro-orbital sinus. Blood was allowed to clot at room temperature and sera was removed and frozen at −80° C. after centrifugation. All procedures were in accordance with the NRC guide for the Care and Use of Laboratory Animals and the Animal Welfare Act.

Hemagglutination inhibition activity: The hemagglutination inhibition (HAI) assay was used to assess functional antibodies to the HA able to inhibit agglutination of horse red blood cells. The procedure was adapted from the Center for Disease Control influenza surveillance manual and performed as previously described.

Serological assays: A quantitative ELISA was performed to assess anti-HA specific IgG in immune serum. Purified rHA (25 ng) was used to coat each well of a 96-well plate. Plates were blocked (25° C. for 2 h) with blocking buffer (PBS pH 7.5 containing 0.05% Tween 20, 5% BSA Fraction V, and 2% bovine gelatin) and then incubated with serial dilutions of each serum sample (37° C. for >90 min). After five washes with PBS, samples were incubated (37° C. for >90 min) with horseradish peroxidase rabbit anti-mouse IgG (1:2500) diluted in blocking buffer. The unbound antibody was removed, and the wells were washed five times with PBS. Samples were then incubated (10-20 min) with 2,2'-azino-bis(3-ethylbenzothiazoline-6-sulphonic acid) (ABTS) substrate and the colorimetric change was measured as the optical density (O.D. at 414 nm) by a spectrophotometer (BioTek, Winooski, Vt., USA). The O.D. value of the sample-matched BSA-only coated plates was subtracted from the O.D of samples where plates were coated with BSA+rHA.

Histology: Lungs were harvested and prepared for immunohistochemistry using standard procedures. After euthanasia, chest cavity was opened and the lungs were gently inflated intratracheally with 4° C. 4% paraformaldehyde in PBS, removed and immersed in 4% paraformaldehyde at 4° C. overnight. The next day, the solution was replaced with 70% ethanol and tissues were kept at 4° C. for up to 2 weeks. Tissue sections were embedded in paraffin, sectioned into slices (~5 μm in thickness), and stained with hematoxylin and eosin (H&E) or left unstained. Tissue sections were imaged with a Qimaging Micropublisher® 5.0 RTV digital camera on an Olympus BX61 fluorescence microscope. To quantify the number of apoptotic lung cells, representative sections were deparaffinized and rehydrated in xylene and graded alcohols, respectively, using standard procedures, and TUNEL assay was performed according to manufacturer's instructions (Roche, Mannheim, Germany). The percentages of TUNEL-positive cells within the tissue sections were determined by counting at least 100 cells each from eight randomly selected fields.

In vivo administration of 5'pppRNA and chikungunya infection model: Control, WT, M5, or M8 5'pppRNA were administered to adult mice using a protocol similar to that of the influenza infection in vivo model. Mice were injected intramuscularly with 2 or 10 μg RNA oligonucleotides in combination with in vivo JetPEI for 24 hours then infected with chikungunya via footpad injection. Treatments were assessed via caliper for footpad swelling or viral RNA copy number via qPCR using chikungunya virus-specific primers. All procedures with chikungunya virus were performed at Oregon Health and Science University.

Example 2

Figure 1:
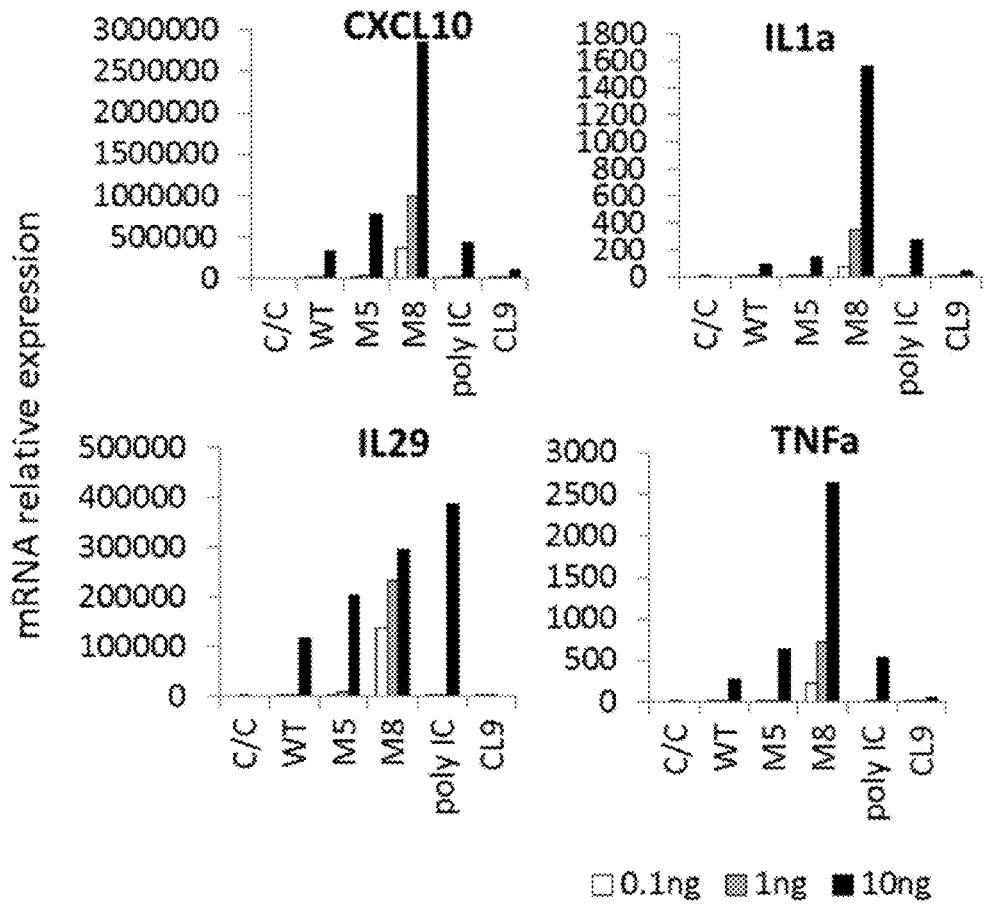
FIG. 1: M8 elicits a more robust innate response compared to other RIG-I agonists.

RIG-I Agonists Comprising Mutations Away from the 5' and 3' Termini of Vesicular Stomatitis Virus Sequence have Improved Antiviral and Anti-Inflammatory Properties Relative to Wild Type RIG-I agonists derived from the 5' and 3' termini of vesicular stomatitis virus (which is referred to as WT, WT-VSV, or 5'pppSEQ ID NO: 5 herein) were tested for antiviral and inflammatory properties. Several modified forms of oligoribonucleotides comprising a 5'triphosphate were synthesized by in vitro transcription and tested for biological activity. Several sequences displayed increased activity; however, the M5 (5'pppSEQ ID NO: 10) and M8 (5'pppSEQ ID NO: 13) 5'-triphosphate oligoribonucleotides resulted in antiviral and immune cytokine levels 10-100 times higher than WT (FIG. 1). The activity of M8 was also superior to that of TLR3 activator poly (I:C) or RIG-I agonist CL9, a SELEX-selected aptamer sequence.

Figure 2A:
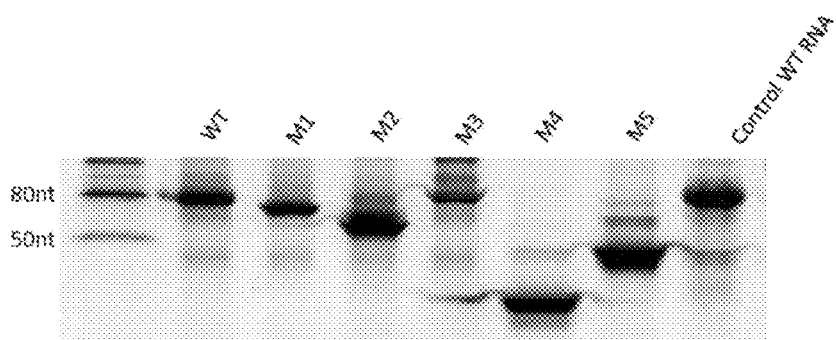
FIG. 2A: In vitro transcription of the disclosed 5'ppp-oligonribonucleotides produces a single RNA product.
Figure 2B:
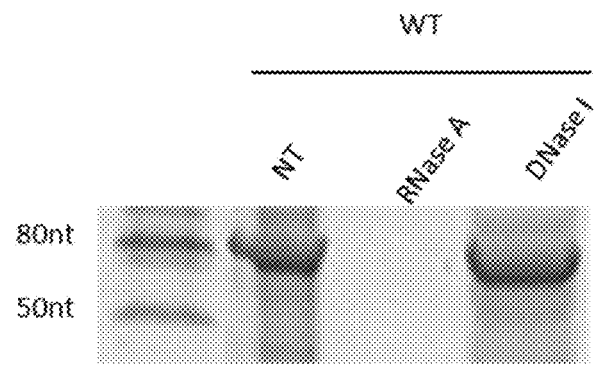
FIG. 2B: In vitro transcribed VSV WT mRNA 5'ppp-oligoribonucleotide product is sensitive to RNase.
Figure 2C:
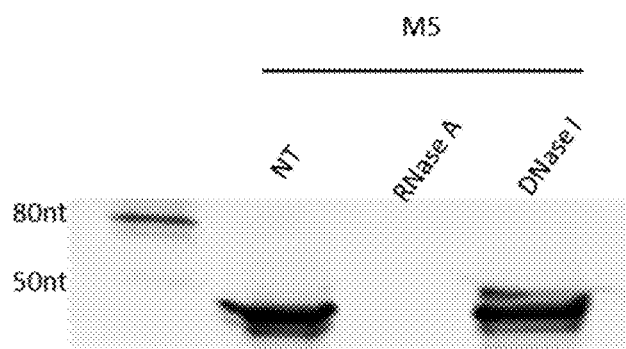
FIG. 2C: In vitro transcribed M5 product is sensitive to RNase.
Figure 3A:
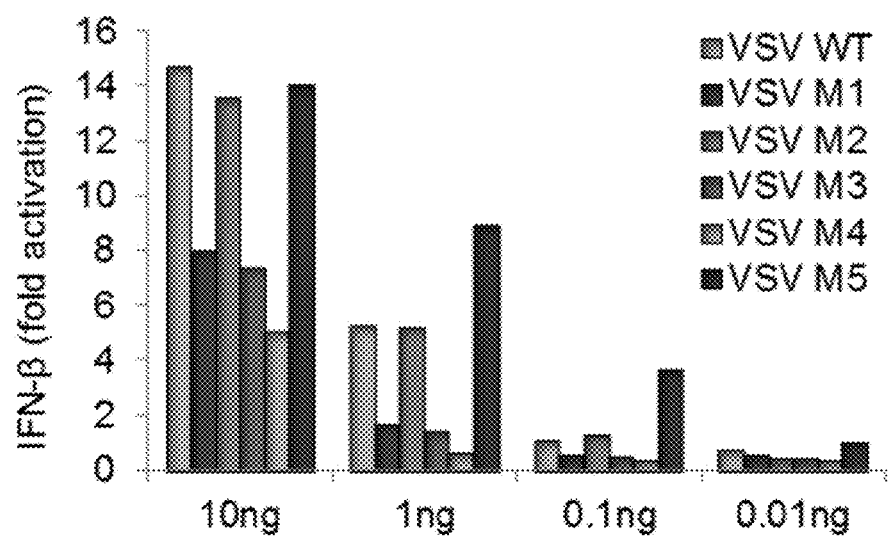
FIG. 3A: M5 is a 5'-triphosphate RIG-I agonist that induces more IFN-β than the prototypical WT structure.
Figure 3B:
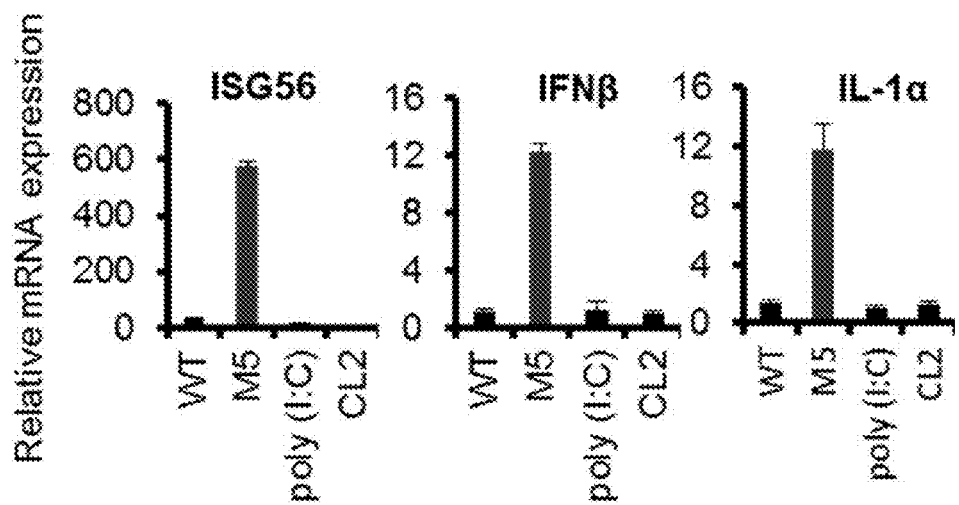
FIG. 3B: M5 induces cytokines to a higher level than other RIG-I agonists as well as other immunostimulants.
Figure 3C:
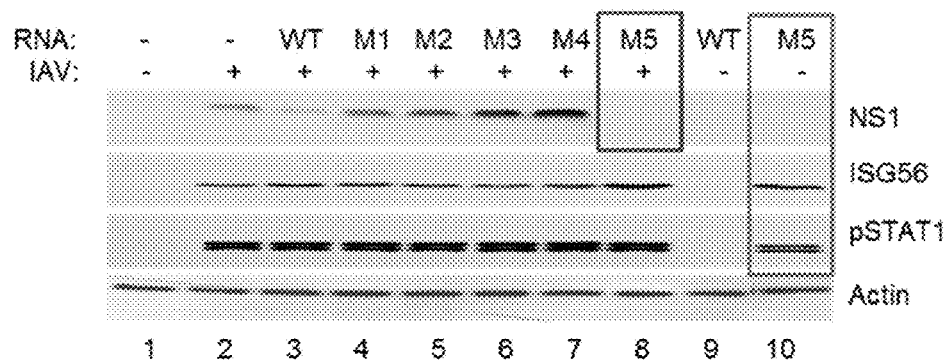
FIG. 3C: M5 inhibits influenza replication in vitro.
Figure 3D:
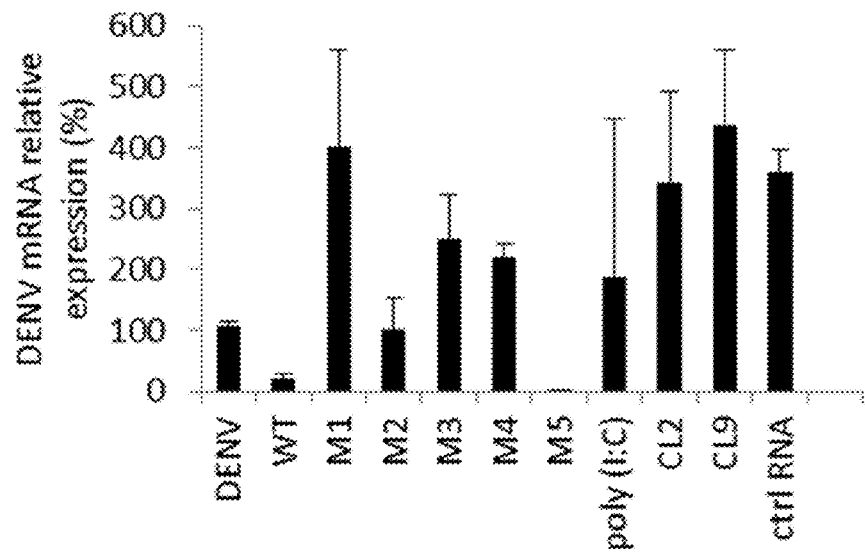
FIG. 3D: Dengue viral RNA synthesis is completely inhibited in M5-treated cells.
Figure 3E:
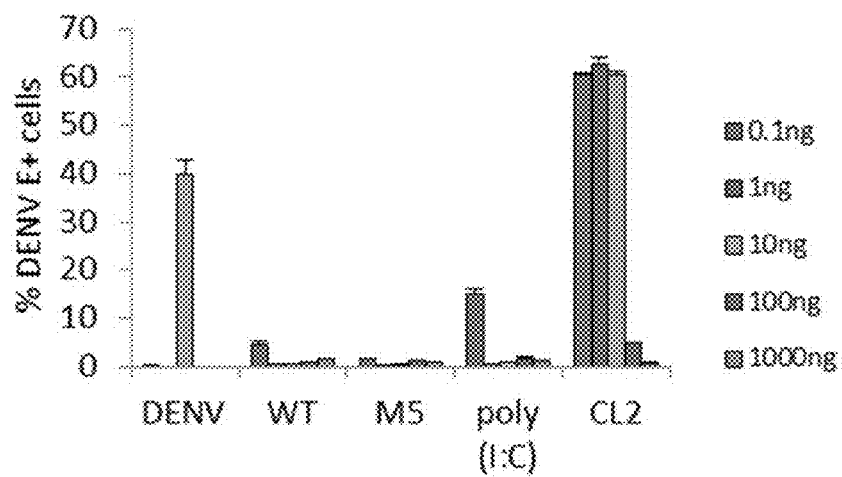
FIG. 3E: M5 (comprising SEQ ID NO: 10) antiviral activity against dengue is superior to other RIG-I agonists and other immunostimulants. A549 cells were transfected with WT, M5, poly (I:C), or CL2 aptamer at a range of concentrations for 24 hours then challenged with dengue virus (MOI 0.5) for 24 hours. Intracellular staining (ICS) and flow cytometry was performed to quantify the percentage of dengue E protein-positive cells.

The first generation of sequences, M1, M2, M3, M4, and M5, (5'pppSEQ ID NO: 6, 5'pppSEQ ID NO: 7, 5'pppSEQ ID NO: 8, 5'pppSEQ ID NO: 9, 5'pppSEQ ID NO: 10 respectively) were synthesized by in vitro transcription, and analyzed for single products (FIG. 2A) that were sensitive to RNase A but not DNase I digestion (FIGS. 2B and 2C), indicating that the in vitro transcribed products were RNA. RIG-I agonists were then assessed for IFN-β activation, cytokine stimulation, as well as virus inhibitory activity (FIG. 3). In all cases, M5 was the best candidate of the group, as it activated IFN-β at lower concentrations (FIG. 3A), stimulated antiviral and innate immune response genes—ISG56, IFNβ, and IL-1a to higher levels than wtVSV (FIG. 3B), and effectively blocked influenza (FIG. 3C) and dengue (FIGS. 3D and 3E) replication in lung epithelial cells, when compared to other RNA agonists. Other agonists were able to stimulate antiviral IFNβ production and block virus replication, but activity was approximately 10-fold lower than M5, indicating the improved activity of this novel sequence.

Figure 4A:
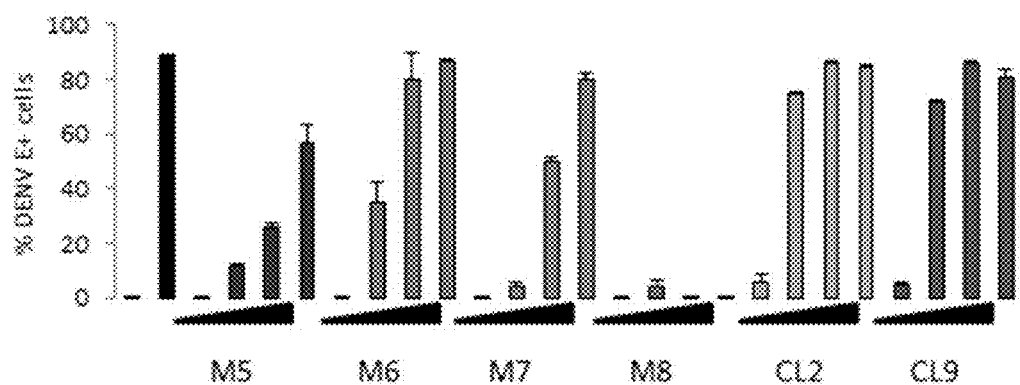
FIG. 4A: Increased dsRNA length provides enhanced antiviral activity against dengue virus.
Figure 4B:
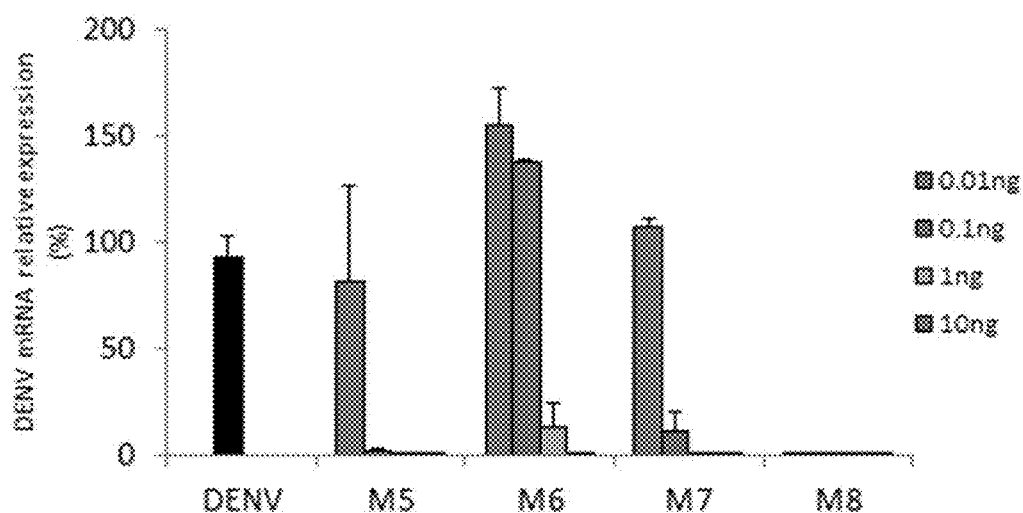
FIG. 4B: M8 completely inhibits dengue viral RNA in vitro.
Figure 4C:
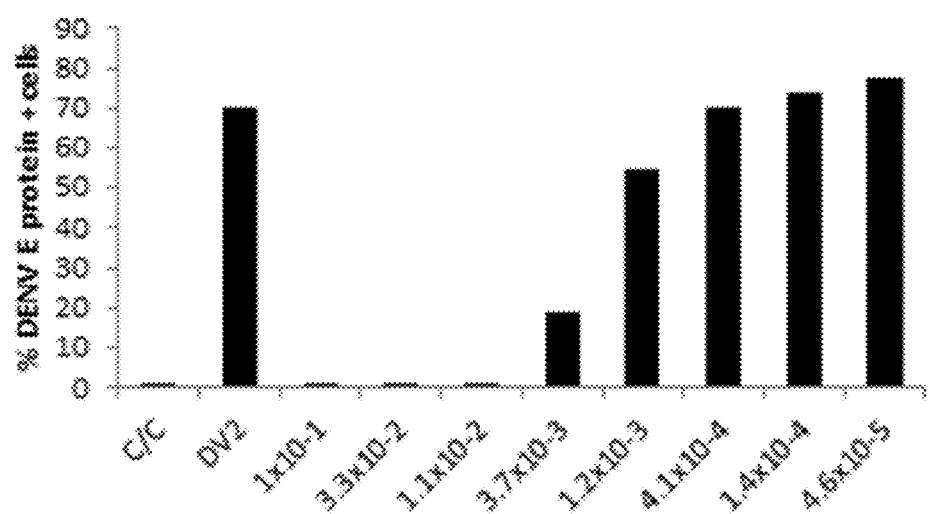
FIG. 4C: Minimal concentrations of M8 are required to completely block viral infection.

A second generation of RNA sequences based on the structure of M5 revealed that increasing the double stranded RNA length improved antiviral activity (FIG. 4). M6 (5'pppSEQ ID NO: 11) and M7 (5'pppSEQ ID NO: 12) were similar to M5 in their ability to block dengue infection, as seen by the percentage of cells positive for dengue E protein (FIG. 4A) and at the RNA level (FIG. 4B). M8 (5'pppSEQ ID NO: 13), however, at comparable concentrations, completely inhibited dengue replication at both levels (FIGS. 4A and 4B). This was further tested by lowering the concentrations used in the dengue challenge experiment and even at a concentration as low as 0.01 ng/ml, no dengue-positive cells were detected in M8-treated cells (FIG. 4C). In all previous experiments, no RNA ribonucleotide was able to elicit the tremendous viral inhibition at such a low concentration.

Figure 5:
FIG. 5: Comparison of WT, M5, and M8 5'pppRNA structures.

A comparison of the original WT 5'-triphosphate oligoribonucleotide (5'pppSEQ ID NO: 5) to the M5 and M8 sequences reveal that although the 5'-triphosphate tail and portions of the double stranded region remain intact (FIG. 5), structure and sequence are altered, indicating their importance in antiviral and inflammatory activity.

Figure 6A:
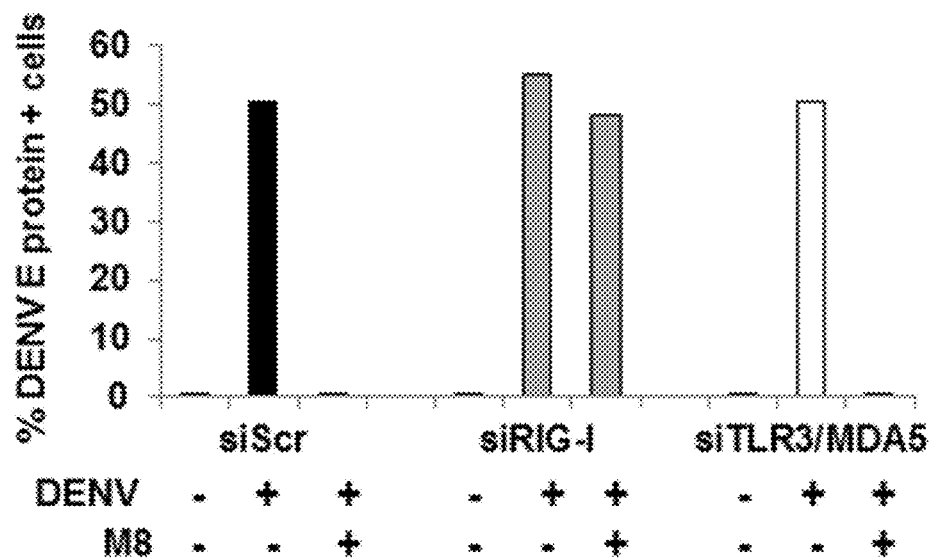
FIG. 6A: The antiviral activity of M8 works through RIG-I.
Figure 6B:
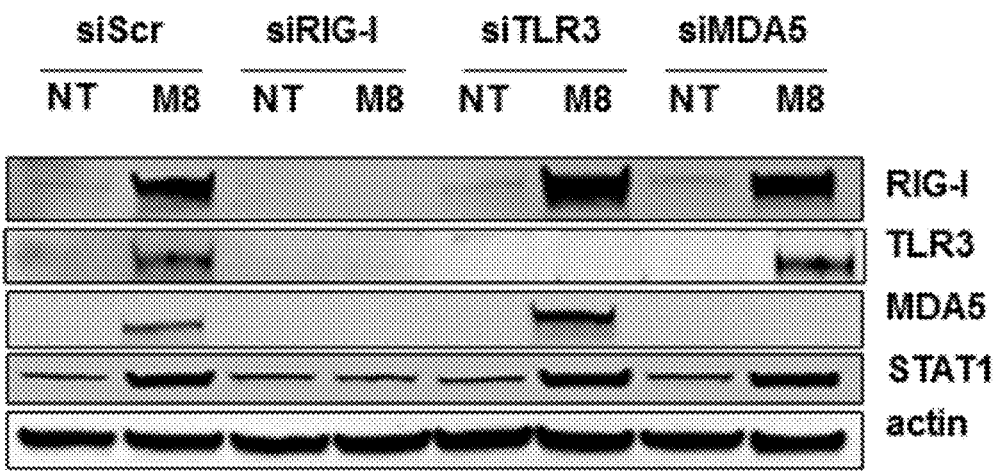
FIG. 6B: M8 activity is dependent on the RIG-I.

To ensure that M8 acts as a RIG-I agonist, cells were knocked down for the RIG-I sensor, or TLR3/MDA5 sensors before treatment with M8. Upon M8 treatment and dengue infection of cells, the absence of RIG-I rendered the M8-treated cells sensitive to virus replication (FIG. 6A), whereas silencing TLR3 and MDA5 (two distinct RNA sensors) did not affect M8 function. This result demonstrates that M8 activity signals through the RIG-I pathway. This result is further supported by the fact that RIG-I depleted cells treated with M8 were unable to upregulate the expression of STAT-1, a component of the IFN antiviral pathway, whereas in the absence of TLR3 and MDA5 sensors, M5-treated cells stimulated the antiviral pathway (FIG. 6B).

Figures 7A, 7B:
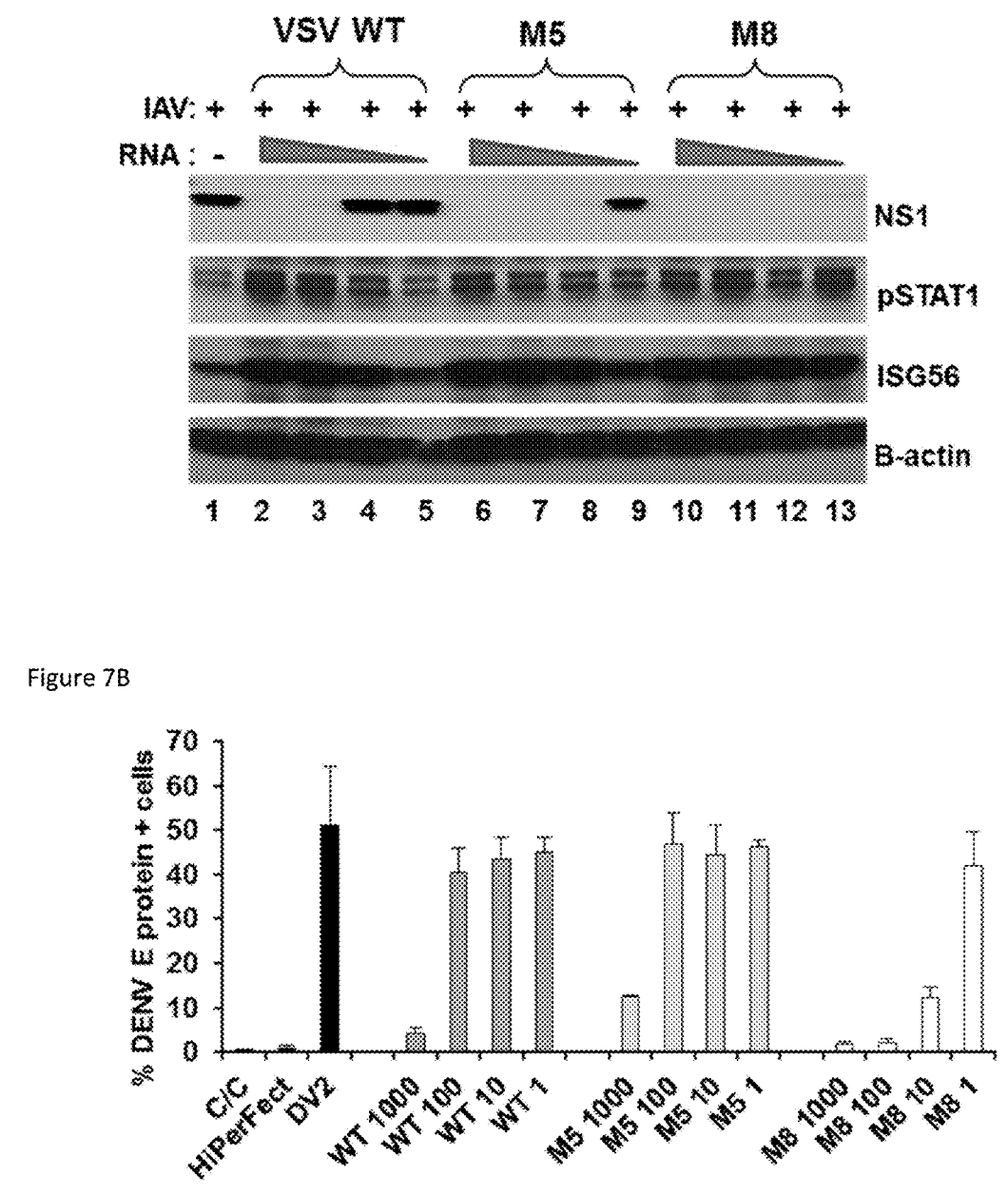
Figure 7C:
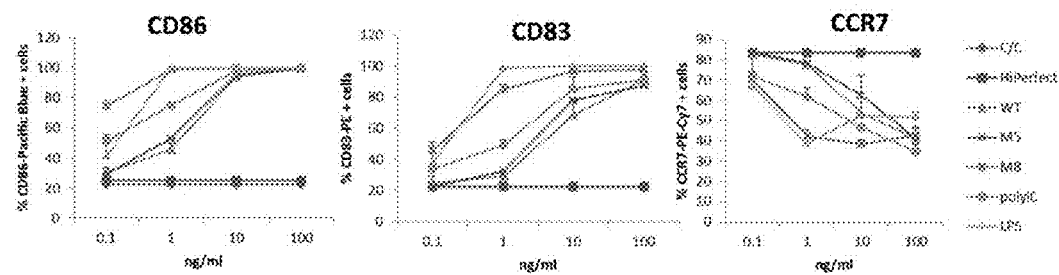
FIG. 7C: M8 (comprising SEQ ID NO: 13) induces primary human dendritic cell maturation. MDDC were transfected with WT, M5, M8, poly (I:C), or LPS (1 ng/ml) for 24 hours. After 36 hours, CD83, CD86, and CCR7 expression levels were evaluated by surface staining and flow cytometry.
Figure 7C:
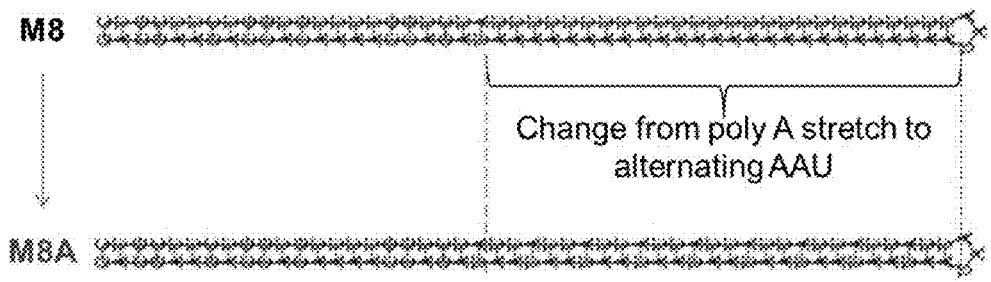

WT, M5, and M8 RNA were assessed for their ability to inhibit different viruses and/or different disease models. In each assay, M8 was more active than WT and M5. Influenza (FIG. 7A) and dengue viruses (FIG. 7B) in A549 and human immune cells respectively were inhibited by M8 at lower concentrations than WT or M5. In monocyte-derived dendritic cells, M8 induced dendritic cell maturation as effectively as the positive control LPS (FIG. 7C); the increase in surface markers CD86 and CD83 illustrate the maturation of DC. This ability of M8 to drive dendritic cell maturation indicates that this RNA sequence can not only stimulate innate antiviral capacity, but also increase the antigen presenting capacity of DC, a function that stimulates the transition from innate to adaptive cellular immunity.

Figure 8B:
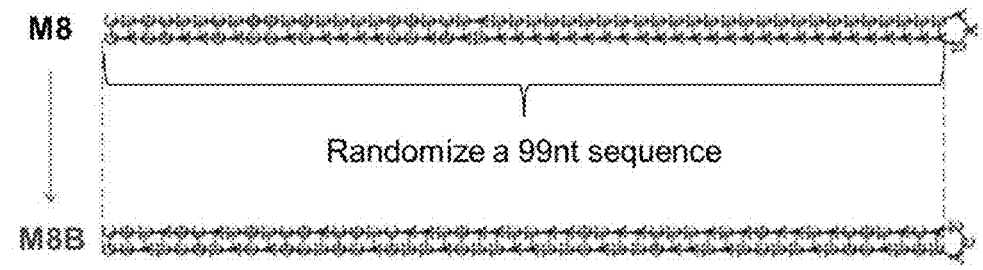
FIG. 8B is a drawing of a second sequence based on M8 (M8B-5'pppSEQ ID NO: 15) M8B was designed by changing the entire sequence of M8. Like M8 and M8A, M8B is 99 nucleotides in length Secondary structures in both FIG. 8A and FIG. 8B were generated with the RNAfold Web Server (University of Vienna).
Figure 9A:
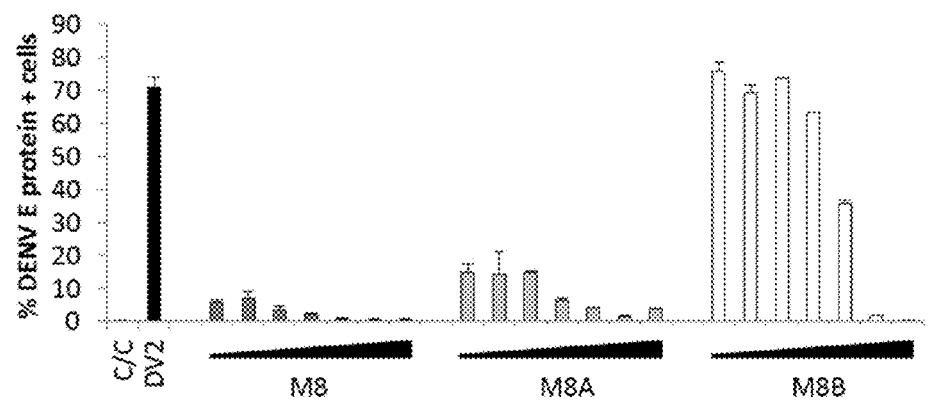
FIG. 9A: M8-derived sequences inhibit DENV replication more effectively than modified forms of M8.
Figure 9B:
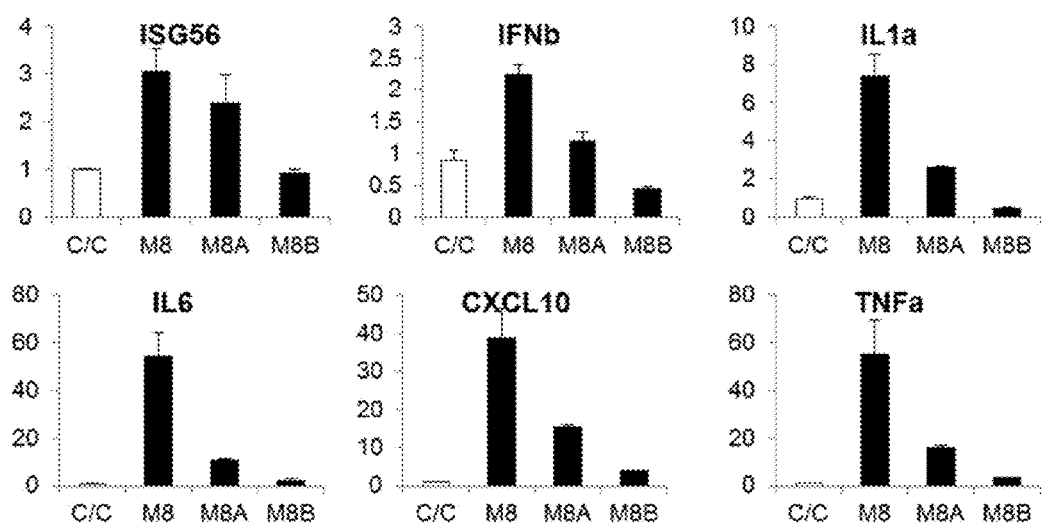
FIG. 9B: M8 induces antiviral cytokines more effectively than modified forms of M8.

Further characterization of the RNA oligonucleotides led to redesign of the M8 sequence (FIG. 8). The sequence length was maintained at 99 nucleotides; however, half of the sequence was modified with alternating AAU (adenine, adenine, uracil) bases (M8A-5'pppSEQ ID NO: 14) or the entire sequence was randomized (M8B-5'pppSEQ ID NO: 15). Upon viral challenge, M8 performed better than its two variants, although M8A still significantly inhibited dengue replication (FIG. 9A). M8B blocked virus at a higher concentration of 1ng/ml. The enhanced activity of M8 versus M8A and M8B was also evident in the expression of several cytokines and antiviral genes (FIG. 9B), suggesting that primary RNA sequence also influences the activity of the RNA agonist.

Figure 10:
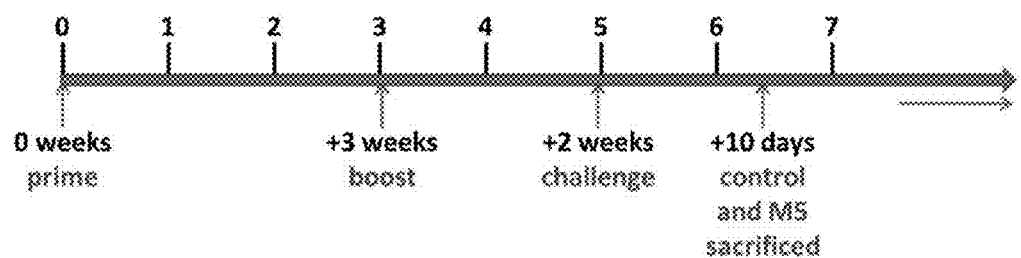
FIG. 10: Vaccination Schedule.
Figure 11A:
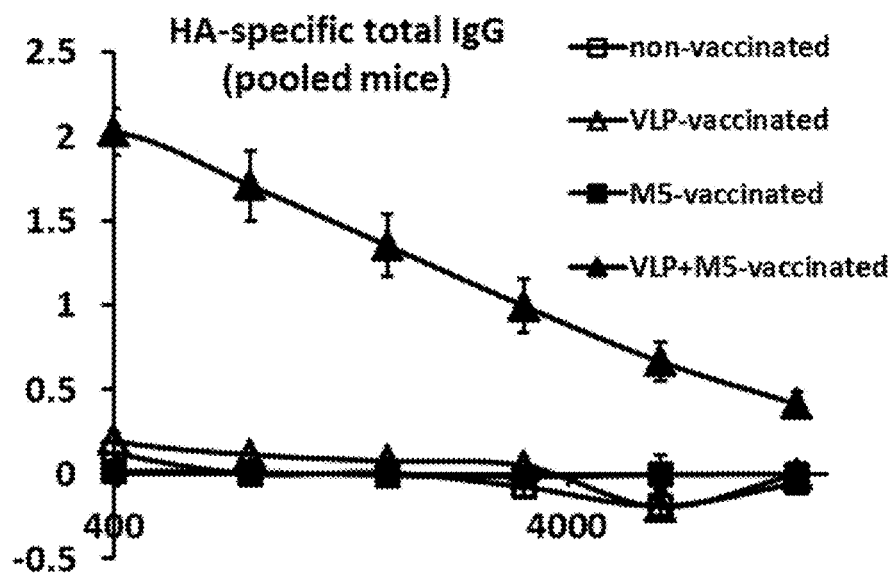
FIG. 11A: Vaccination with a virus like peptide-M5 combination increases HA-specific total IgG compared to VLP or M5 alone.
Figure 11B:
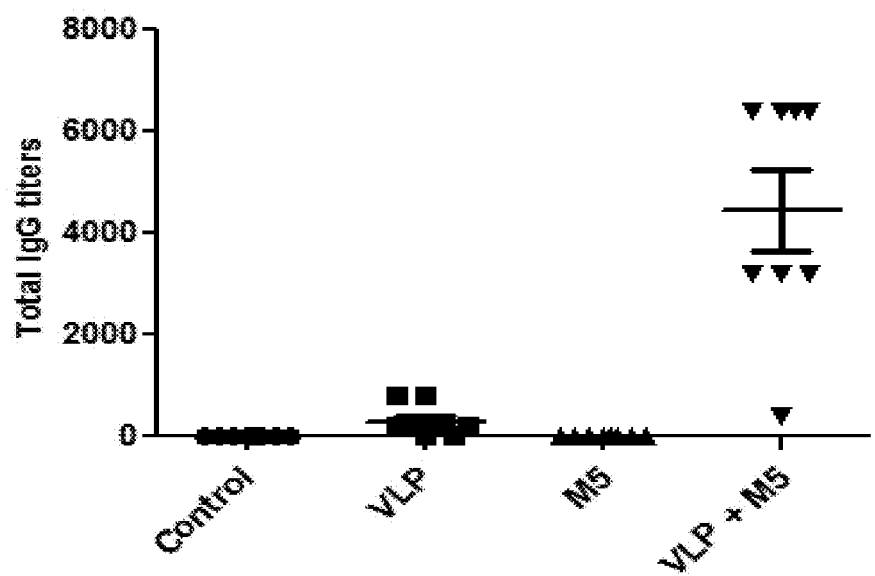
FIG. 11B: Total IgG titers are enhanced in VLP-M5 treated mice.
Figure 11C:
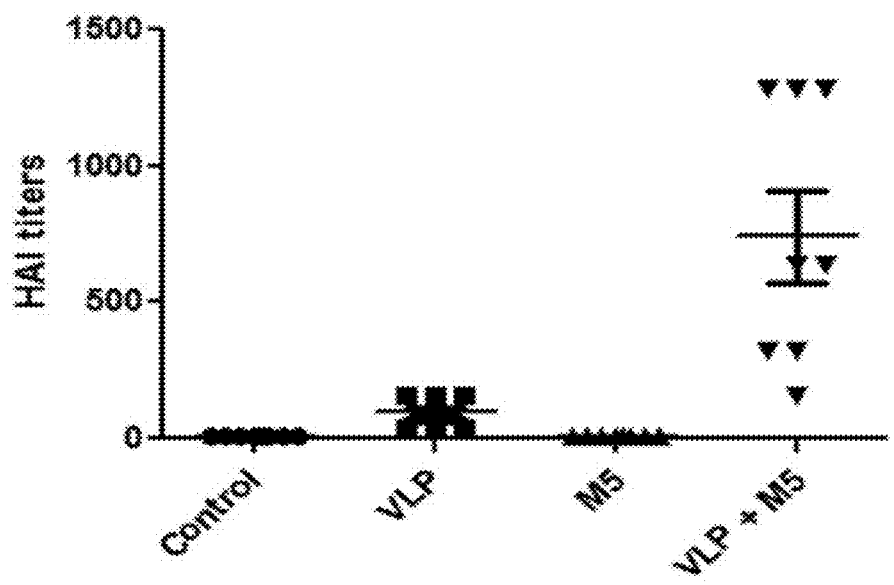
FIG. 11C: VLP-M5 vaccination induces higher neutralizing antibody titers against influenza.
Figure 11D:
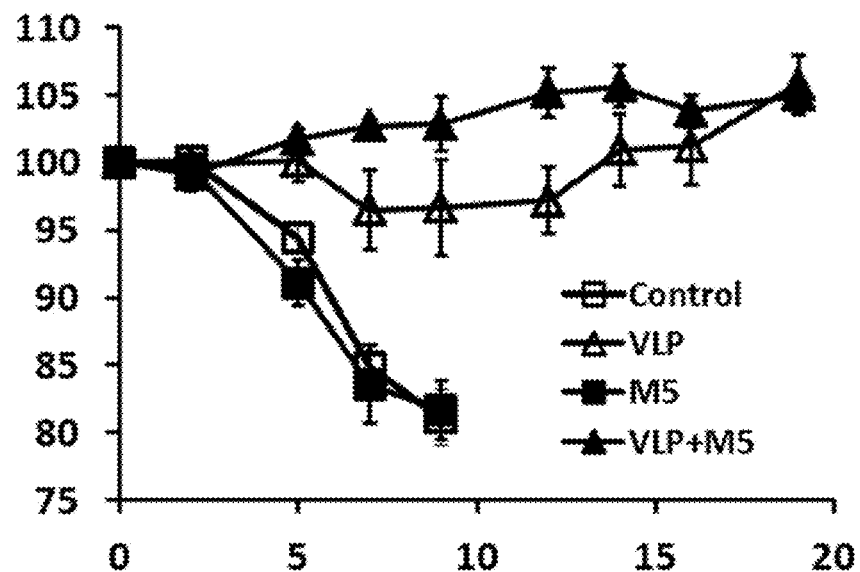
FIG. 11D: VLP- and VLP+M5-treated mice are protected from lethal influenza virus challenge.
Figure 12A:
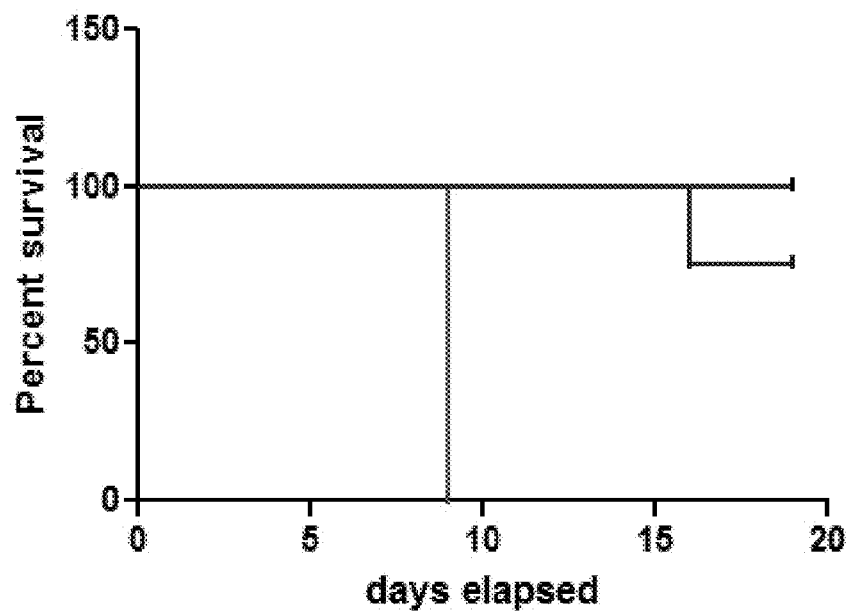
FIG. 12A: VLP-M5 vaccinated mice survive lethal challenge of influenza A.
Figure 12B:
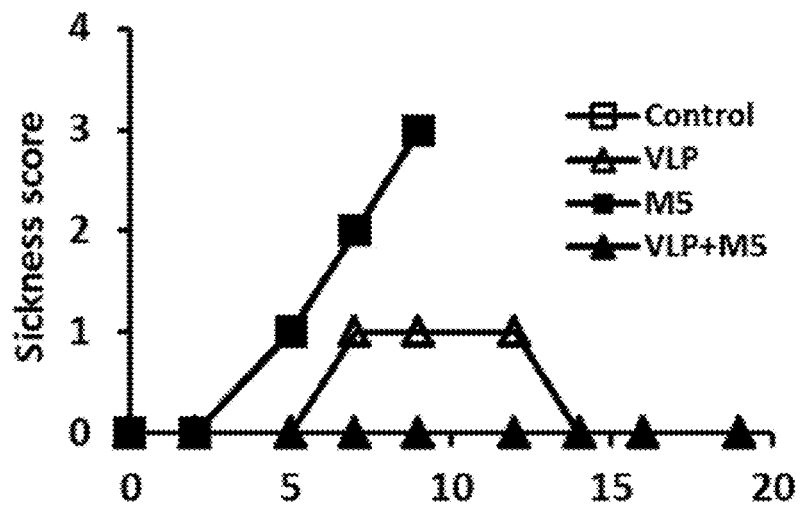
FIG. 12B: VLP-M5 vaccinated mice do not develop pathologic illness after challenge with H5N1.
Figure 12C:
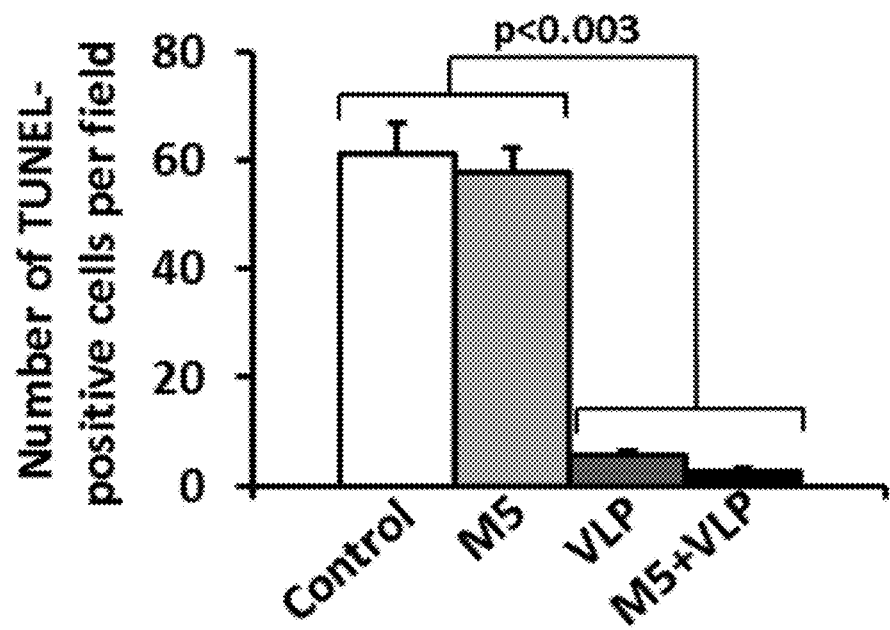
FIG. 12C: Influenza-induced cell death was inhibited in VLP and VLP-M5 vaccinated animals.
Figure 13:
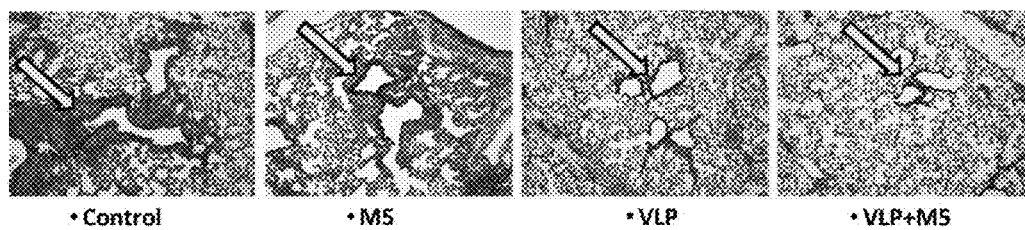
FIG. 13: Inflammation in bronchial airways of animal challenged with reassorted H5N1.

The novel sequences M5 and M8 were then evaluated in vivo for their antiviral and adjuvant activities. To assess the capacity of M5 to increase antibody responses to influenza virus like particle (VLP) vaccination, Balb/c mice were injected intramuscularly (IM) with 25 µg of M5, 3 mg VLP (based on haemagglutinin (HA) content) or the combination of VLP-M5 (FIG. 10). Three weeks after the first vaccination, a same-dose booster vaccine was injected. Two weeks after the second dose, mice were bled and serum was isolated to determine total HA-specific IgG antibody titers. Addition of M5 increased HA-specific (FIGS. 11A and 11B) as well as neutralizing antibody titers (FIG. 11C), as determined by HA-specific ELISA and haemagglutination inhibition assays (HAI), respectively. Mice were then challenged with a lethal dose of the reassorted H5N1 virus (5,000 plaque forming units/animal) intranasally, and their weight, survival, and sickness score were assessed over three weeks. Control and M5-vaccinated mice continuously losing weight and were humanely euthanized at nine days post-challenge (FIG. 11D). Mice vaccinated only with VLPs lost weight, displayed mild signs of sickness, and two mice had to be euthanized at day 16 (FIGS. 12A and 12B). Only mice vaccinated with VLP+M5 continuously gained weight and displayed no overt signs of infection. Post-mortem examination of lung tissues revealed increased apoptotic cell death (TUNEL-positive cells) in the control group and in mice vaccinated with M5 (FIG. 12C). Additionally, H&E staining revealed increased inflammation in the bronchial airways in control and in mice vaccinated with M5 (FIG. 13, yellow arrow).

Figure 14A:
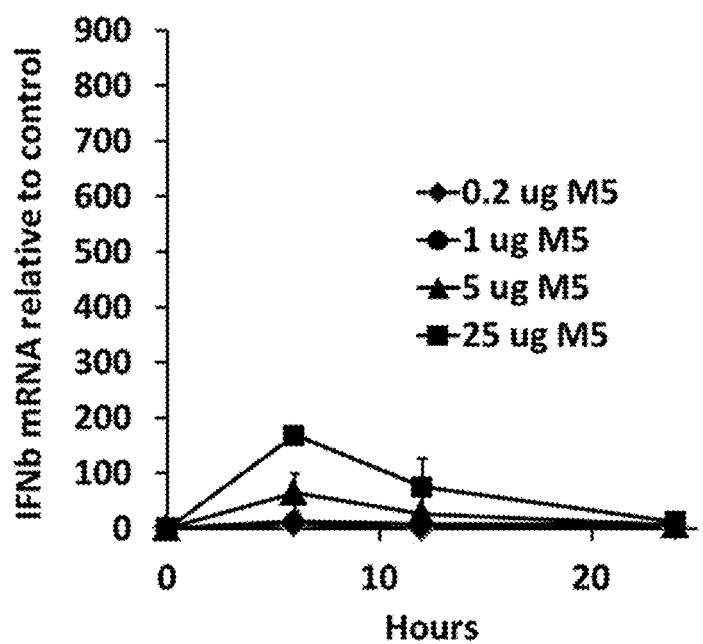
FIG. 14A: Intramuscular inoculation of M5 stimulates antiviral IFN-β mRNA in mouse skin.
Figure 14B:
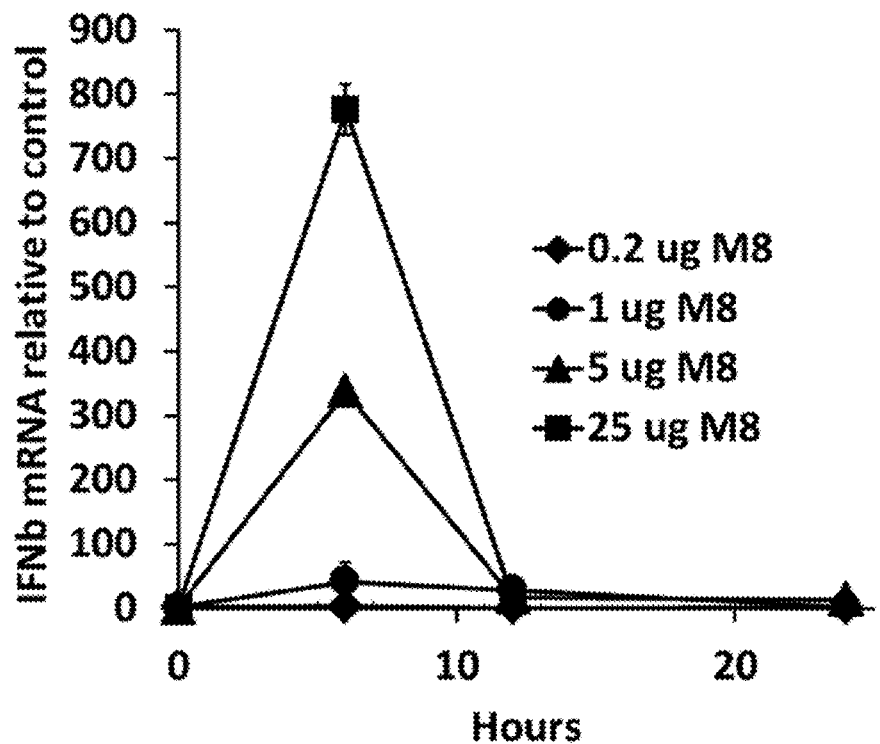
FIG. 14B: Intramuscular inoculation of M8 stimulates antiviral IFN-β mRNA in mouse skin.

To evaluate the activity of M5 and M8 with a different route of administration, mice were injected intramuscularly (as with a vaccine) with of WT, M5 or M8 and the induction of IFNβ mRNA levels after injection were measured. At indicated time points, muscles were harvested, RNA isolated, and the levels of IFNβ were determined by RT-PCR (FIGS. 14A and 14B). Based on these results, M8 induces 3-5 fold higher levels of IFNβ mRNA 6 h post-injection.

Figure 15A:
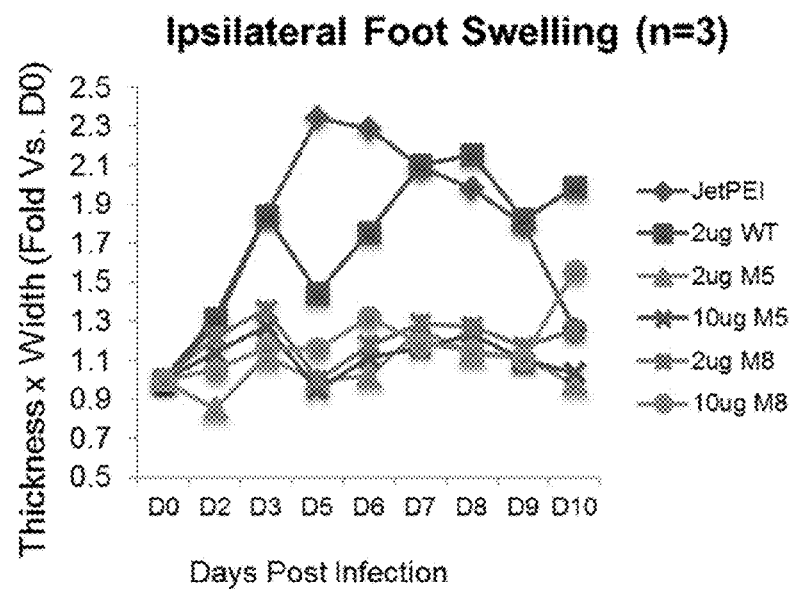
FIG. 15A: M5 and M8 prevent foot swelling associated with chikungunya infection.
Figure 15B:
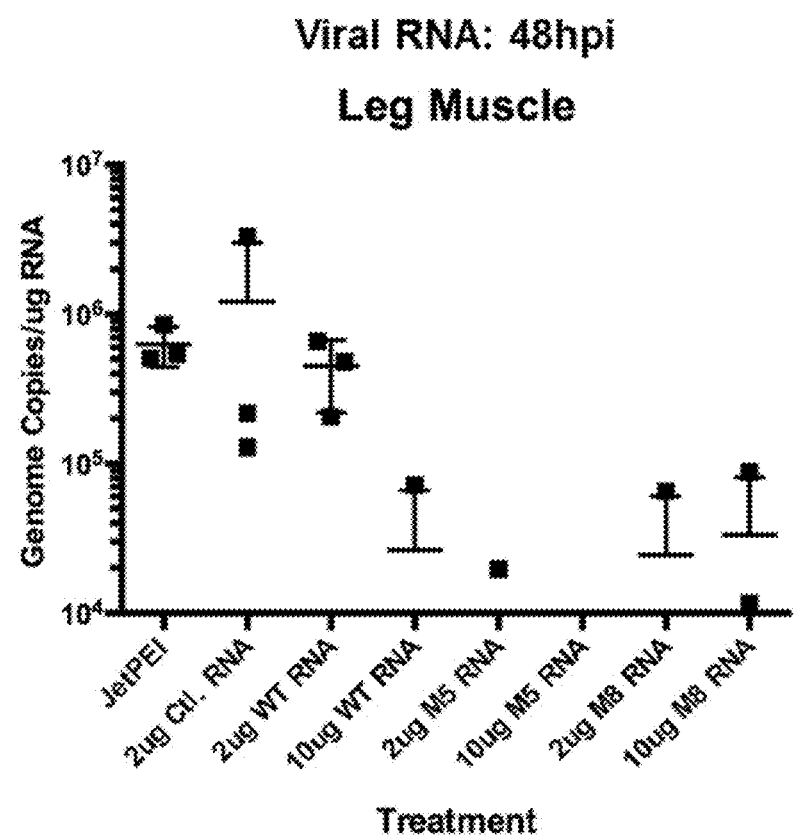
FIG. 15B: Chikungunya viremia is reduced in M5 and M8 treated mice.

In vivo antiviral activity of M5 and M8 sequences was also examined in a murine model of chikungunya virus pathogenesis, in which swelling of the footpad is used as a marker of inflammation and arthritis. Both 2 and 10 µg of either M5 or M8 were efficient in preventing swelling in the ipsilateral foot pad (FIG. 15A). M5 and M8 also inhibited chikungunya viremia (virus in the blood), as assessed by measuring chikungunya viral RNA levels in the blood (FIG. 15B).

Example 3

Sequence Specific Modifications Enhance the Broad-Spectrum Antiviral Response Activated by RIG-I Agonists The cytosolic RIG-I (retinoic acid-inducible gene I) receptor plays a pivotal role in the initiation of the immune response against RNA virus infection by recognizing short 5'-triphosphate (5'ppp)-containing viral RNA and activating the host antiviral innate response. Disclosed herein are novel 5'ppp RIG-I agonists of various lengths, structures, and sequences. The generation of the antiviral and inflammatory responses in human epithelial A549 cells, human innate immune primary cells, and murine models of influenza and chikungunya viral pathogenesis were evaluated. A 99-nucleotide, uridine-rich hairpin 5'-pppRNA termed M8 stimulated an extensive and robust interferon response compared to other modified 5'-pppRNA structures, RIG-I aptamers, or poly(I•C). Manipulation of the primary RNA sequence alone was sufficient to modulate antiviral activity and inflammatory response. These mechanisms were dependent exclusively on RIG-I and independent of MDA5 and TLR3. Both prophylactic and therapeutic administration of M8 effectively inhibited influenza virus and dengue virus replication in vitro. Furthermore, multiple strains of influenza virus that were resistant to oseltamivir, an FDA-approved therapeutic treatment for influenza, were highly sensitive to inhibition by M8. Finally, prophylactic M8 treatment in vivo prolonged survival and reduced lung viral titers of mice challenged with influenza virus, as well as reducing chikungunya virus-associated foot swelling and viral load. Altogether, these results demonstrate that 5'-pppRNA can be rationally designed to achieve a maximal RIG-I-mediated protective antiviral response against human-pathogenic RNA viruses.

The development of novel therapeutics to treat human-pathogenic RNA viral infections is an important goal to reduce spread of infection and to improve human health and safety. Disclosed herein is an RNA agonist with enhanced antiviral and inflammatory properties against influenza, dengue, and chikungunya viruses. A novel, sequence-dependent, uridine-rich RIG-I agonist generated a protective antiviral response in vitro and in vivo and was effective at concentrations 100-fold lower than prototype sequences or other RNA agonists, highlighting the robust activity and potential clinical use of the 5'-pppRNA against RNA virus infection. Altogether, the results identify a novel, sequence-specific RIG-I agonist as an attractive therapeutic candidate for the treatment of a broad range of RNA viruses, a pressing issue in which a need for new and more effective options.

Human-pathogenic RNA viral infections, including influenza, dengue, and chikungunya, pose significant threats to human health and safety. For this reason, the development of prophylactic and therapeutic antivirals to treat and limit spread of infection remains a growing unmet medical need. Currently, there are no therapeutics for the prevention or treatment of dengue or chikungunya infections, and approved antiviral compounds to treat influenza have significant problems associated with their use. For instance, anti-influenza agents such as amantadine and rimantadine block virus uncoating but are not recommended for currently circulating influenza A or B virus strains because of widespread resistance (Drinka P J and Haupt T, *J Am Geriatr Soc* 55, 923-926 (2007); incorporated by reference herein). Oseltamivir, a neuraminidase inhibitor, is also active against influenza A and B viruses at early stages of infection but has given rise to drug-resistant mutants (Bloom J D et al, *Science* 328, 1272-1275 (2010); incorporated by reference herein). Therapies that harness and activate the natural immune defense may circumvent the issues of the emergence of drug resistance and off-target effects. The innate immune system provides the initial barrier against viral infection, initiating a cascade of signaling pathways and sensors that detect and clear the intruding virus. RNA viruses possess pathogen-associated molecular patterns (PAMPs) that are sensed by pattern recognition receptors (PRR) (Brennan K and Bowie A G, *Curr Opin Microbiol* 13, 503-507 (2010); Tekeuchi O and Akira S, *Immunol Rev* 227, 75-86 (2009); Wilkins C and Gale Jr. M, *Curr Opin Immunol* 22, 41-47 (2010); Yoneyama M and Fujita T, *Rev Med Virol* 20, 4-22 (2010); and Akira S et al, *Cell* 124, 783-801 (2006); all of which are incorporated by reference herein). Toll-like receptor (TLR) and RIG-I (retinoic acid-inducible gene I)-like receptor (RLR) families generate an innate immune response upon recognition of broadly conserved PAMPs on viruses and bacteria Goubau D et al, Immunity 38, 855-860 (2013); incorporated by reference herein). RIG-I recognizes short double-stranded RNA (dsRNA) oligonucleotides of <100 nucleotides in length bearing 5'-triphosphate or 5'-diphosphate termini (Goubau D et al, *Nature* 514, 372-375 (2014); incorporated by reference herein), while MDA5 generally recognizes longer, dsRNA (>300 nucleotides) lacking a 5'-triphosphate moiety. RIG-I detects viral RNA through its helicase domain (Bamming D and Horvath C M, *J Biol Chem* 284, 9700-9712 (2009); Fujita T et al, *Biochimie* 89, 754-760 (2007); Jiang X et al, *Immunity* 36, 959-973 (2012); and Schmidt A et al, *J Mol Med (Berl)* 80, 5-12 (2011); all of which are incorporated by reference herein), leading to conformational changes that expose the effector caspase activation and recruitment domain (CARD), which in turn interacts with the mitochondrial adaptor MAVS (Kawai T et al, *Nat Immunol* 6, 981-988 (2005); Komuro A et al, *Cytokine* 43, 350-358 (2008); and Meylan E et al, *Nature* 437, 1167-1172 (2005); all of which are incorporated by reference herein). MAVS serves as a signaling platform for protein complexes that trigger activation of the transcription factors NF-κB, interferon (IFN)-regulatory factor 3 (IRF-3), and IFN regulatory factor 7 (IRF-7), leading to the induction of antiviral programs that include production of type I IFN as well as proinflammatory cytokines and antiviral factors (Belgnaoui S M et al, *Curr Opin Immunol* 23, 564-572 (2011); Kawai T and Akira S, *Ann NY Acad Sci* 1143, 1-20 (2008); Pichlmair A et al, *Science* 314, 997-1001 (2006); Rehwinkel J and Reis e Sousa C, *Science* 327, 284-286 (2010); Rehwinkel J et al, *Cell* 140, 397-408 (2010); and Takeuchi O and Akira S, *Cell* 140, 805-820 (2010); all of which are incorporated by reference herein). A secondary response is induced by IFN binding to the type I IFN receptors (IFN-α/βR), which activate the JAK-STAT pathway and induce interferon-stimulated genes (ISGs) and the antiviral immune response (Sadler A J and Williams B R, *Nat Rev Immunol* 8, 559-568 (2008) and Schoggins J W et al, *Nature* 472, 481-485 (2011); both of which are incorporated by reference herein). More recently, RIG-I has been shown to function as both an innate sensor and an antiviral factor by triggering downstream interferon signaling events and disrupting the interaction between hepatitis B virus (HBV) polymerase and pgRNA (Sato S et al, *Immunity* 42, 123-132 (2015); incorporated by reference herein). Overall, novel therapies specifically targeting the RIG-I pathway have the potential to elicit a broad-spectrum, antiviral, inflammatory, and immune modulatory response and thus represent an attractive strategy for the design and development of novel and improved antiviral therapies.

The antiviral activity of a short in vitro synthesized 5'-triphosphate RNA (5'-pppRNA) derived from the 5' and 3' untranslated regions (UTRs) of the vesicular stomatitis virus (VSV) genome (termed wild-type [WT] 5'-pppRNA) herein has been disclosed (Goulet M L et al, *PLoS Pathog* 9, e1003298 (2013); incorporated by reference herein). Pretreatment with WT 5'-pppRNA activated the RIG-I signaling pathway and triggered a robust antiviral response that significantly decreased infection by several pathogenic viruses, including dengue virus, hepatitis C virus (HCV), H1N1 influenza virus A/PR/8/34, and HIV-1. In vivo, intravenous delivery of the WT 5'-pppRNA stimulated an antiviral state that inhibited a broad spectrum of RNA viruses and protected mice from lethal influenza virus challenge (Olagnier D et al, *J Virol* 88, 4180-4194 (2014); incorporated by reference herein).

The nature of the ligand recognized by RIG-I has been the subject of numerous studies. Structural motifs, lengths, and sequences of virus-derived 5'-pppRNA and other RNA agonists have been analyzed and found to play critical roles in the response to viral infection. In vitro-synthesized RNA with a 5'-terminal triphosphate moiety was first identified as a RIG-I agonist (Hornung V et al, *Science* 314, 994-997 (2006) and Schlee M et al, *Immunity* 31, 25-34 (2009); both of which are incorporated by reference herein) however, more recently, it was discovered that a 5'-diphosphate terminus could also be recognized by RIG-I to mediate an antiviral response (Goubau et al, 2014 supra). RIG-I stimulation was dependent on double stranded RNA at least 20 nucleotides long possessing blunt base pairing at the 5' end Schlee M and Hartmann G, *Mol Ther* 18, 1254-1262 (2010); incorporated by reference herein). Ligands recognized by RIG-I include double-stranded RNA, found in conserved 5' and 3' UTRs of negative single-strand RNA virus genomes, displaying high base pair complementarity and a panhandle structure.

Most studies on RIG-I antiviral properties have used virus derived 5'-pppRNA or defective interfering particles or commercially available synthetic 5'-pppRNA to trigger the RIG-I antiviral response. In the present study, we report for the first time the sequence-specific activity of a novel RIG-I agonist active against a number of RNA viruses both in vitro and in vivo. Modifications to the structure, length, and sequence of a prototypical 5'-triphosphate-containing RNA significantly potentiated the host antiviral response against influenza, dengue and chikungunya virus infections while maintaining the specificity for interaction with the RIG-I cytosolic sensor.

Figure 16B:
FIG. 16B is an image of a gel showing in vitro transcribed 5'pppRNA that was DNase-treated, purified and then run on a denaturing TBE-urea gel.

5'-pppRNA sequence and structure determine antiviral activity: Optimization of the prototypical VSV-derived WT 5'-pppRNA (Goulet et al, 2013 supra and Schlee et al, 2009 supra) resulted in novel structures with enhanced antiviral activity compared to the short form of polyinosinic-poly(C) [poly(I•C)], a well-known and -characterized TLR3 agonist, or the SELEX-selected RIG-I aptamers CL2 and CL9 Hwang S Y et al, *Nucleic Acids Res* 40, 2724-2733 (2012); incorporated by reference herein). A representation of the predicted secondary structure of each of the agonists generated is included in FIG. 16A. The 5'-triphosphate RNA agonists were generated by in vitro transcription as previously described (Goulet et al 2013 supra), and gel analysis revealed a single product (FIG. 16B) susceptible to digestion by RNase A but not by DNase I. In the first generation of modified sequences, modifications to the primary RNA sequence that eliminated mismatch in the double-stranded RNA (dsRNA) region (M1), removed the panhandle sequence (M2), introduced additional bases to the dsRNA region (M3), or generated a short dsRNA pin loop (M4) did not enhance agonist activity when assayed for IFN-γ induction or antiviral effects. However, the addition of extra base pairs to the M4 sequence resulted in a 59-nucleotide dsRNA structure (M5) that induced higher levels of IFN-γ and ISG56 and inhibited influenza virus and dengue virus (DenV) replication more effectively than the prototypical WT 5'-pppRNA. Further modification of M5, via the addition of AU base pairs to increase the length of the dsRNA stem structure (M6 to M8), further enhanced antiviral activity. Human lung epithelial A549 cells treated with M8 were protected from DenV infection at concentrations ~2-log lower than those treated with M5. The enhanced antiviral activity of M5 and M8 was increased 10- and 100-fold, respectively, compared to WT, as measured by antiviral activity and stimulation of innate immune molecules (FIGS. 16C to 16G).

Figure 16C:
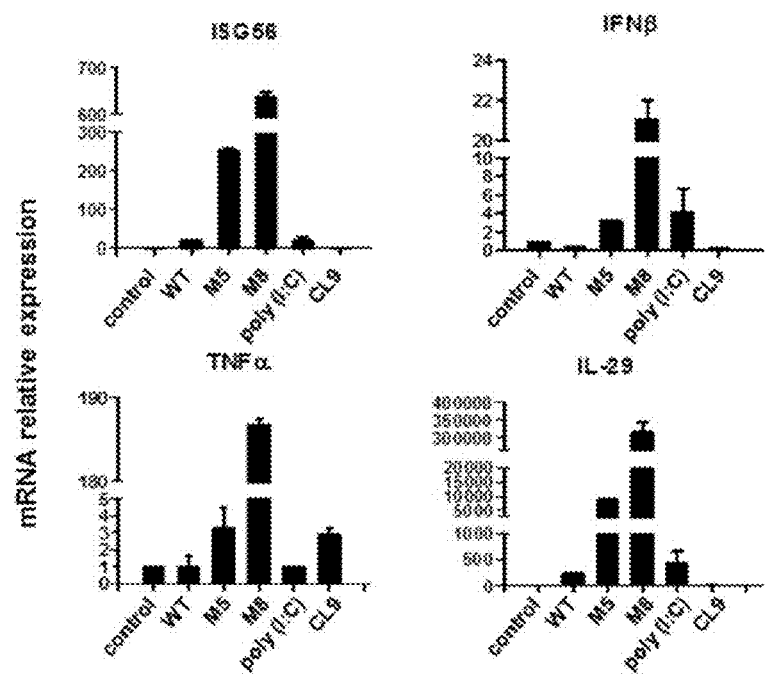
FIG. 16C is a set of bar graphs showing the results from A549 cells that were transfected with WT, M5, M8, CL9 aptamer, or poly (I:C) (2 fmol) using Lipofectamine RNAiMax. After 24 h, cells were harvested and total mRNA was isolated. Antiviral and inflammatory gene expression was determined by qPCR. Data are from two independent experiments performed in triplicate and represent the means±SEM.
Figure 16D:
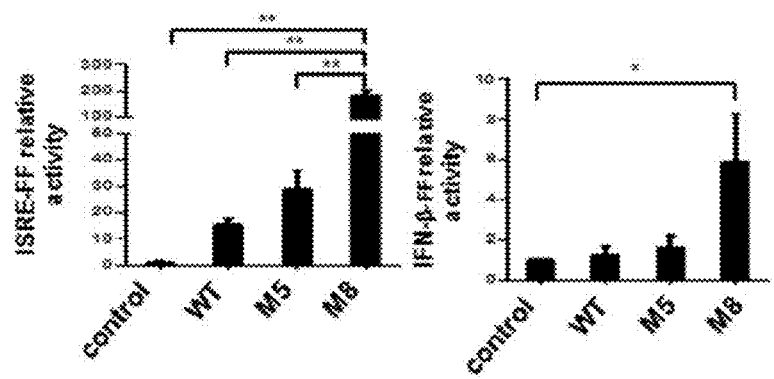
FIG. 16D is a set of bar graphs showing the results from HEK293T cells that were co-transfected ISRE or IFN-β promoter reporter plasmid (200 ng) along with WT, M5, or M8 5'pppRNA (10 ng/ml). Luciferase activity was analyzed 24 h post-transfection by the Dual-Luciferase Reporter assay. Relative luciferase activity was measured as fold induction relative to the basal level of reporter gene. Data are from two independent experiments performed in triplicate and represent the means±SEM.
Figure 16E:
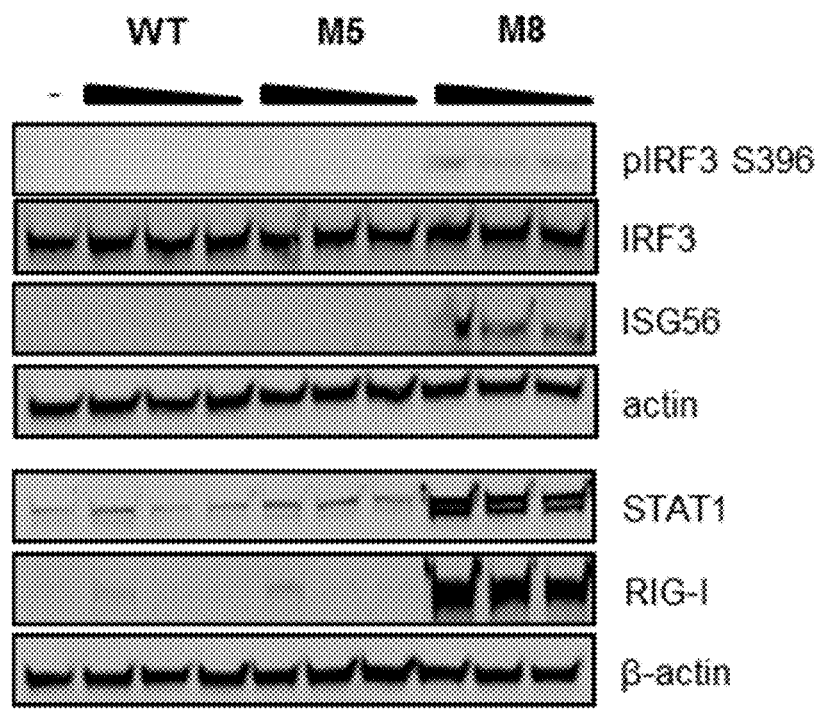
FIG. 16E is an image of an immunoblot showing the results from A549 cells that were transfected with 5'pppRNA (0.1, 1, or 10 ng/ml) and whole cell extracts were prepared, resolved by SDS-PAGE, and analyzed by immunoblotting for IRF3 pSer396, IRF3, ISG56, STAT1, RIG-I, and β-actin 24 h later. One representative Western blot out of three independent triplicates is shown.
Figure 16F:
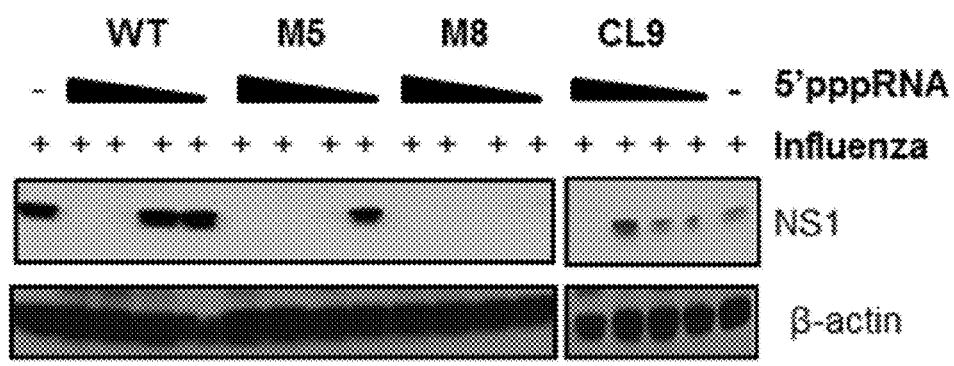
FIG. 16F is an image of an immunoblot showing the results from A549 cells that were transfected with 5'pppRNA or CL9 aptamer (0.01, 0.1, 1, or 10 ng/ml) for 24 h then infected with influenza (MOI 0.2) for 24 h. Whole cell extracts were prepared, resolved by SDS-PAGE, and analyzed by immunoblotting for influenza viral protein NS1 and β-actin. One representative Western blot from one experiment is shown.
Figure 16G:
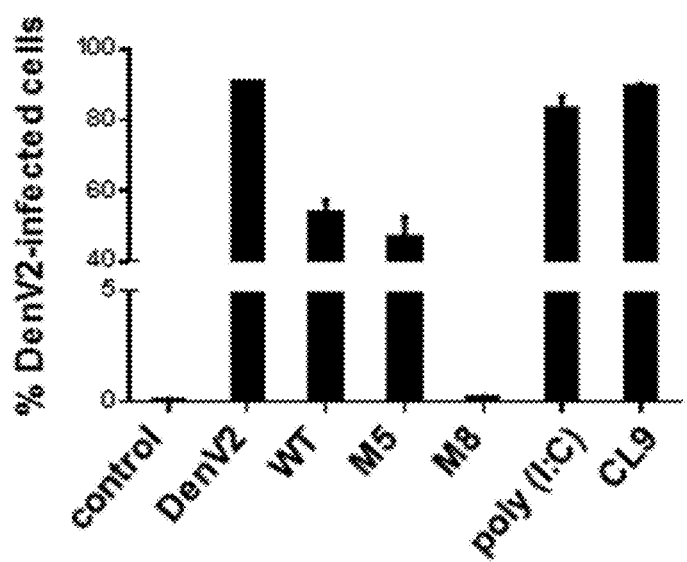
FIG. 16G is a bar graph showing the results from A549 cells that were transfected with WT, M5, or M8 5'pppRNA, poly (I:C), or CL9 aptamer (1 ng/ml) for 24 h then challenged with dengue virus (MOI 0.5). Percentage of infected cells was determined 24 h post-infection by intracellular staining of DENV E protein expression. Data are from two independent experiments performed in triplicate and represent the means±SEM.

To examine the relative activities of the optimized agonist, A549 cells were transfected with WT, M5, or M8 5'-pppRNAs, and expression of various cytokines and IFN-stimulated genes (ISG) was evaluated by quantitative PCR; equimolar amounts of RNA were used to compensate for the disparities in agonist length. Expression of the interferon-stimulated gene ISG56, type I and III interferons (IFN-γ and interleukin 29 [IL-29]), and the cytokine tumor necrosis factor alpha (TNF-α), measured at the RNA level, was significantly higher in M8-treated cells than in cells treated with other agonists (FIG. 16C). ISG56, IFN-γ, TNF-α, and IL-29 mRNA expression levels in M8-treated cells were 33.7-, 47.9-, 1,397.3-, and 185.0-fold higher than those in WT-treated cells, respectively. Increased mRNA expression levels were accompanied by enhanced interferon-stimulated response element (ISRE) and IFN-γ activity in a luciferase reporter assay (FIG. 16D) and by increased phosphorylation of IRF3 at S396 and expression of ISG56, STAT1, and RIG-I protein (FIG. 16E) in M8-treated cells compared to WT- or M5-treated cells. At low (0.01-ng/ml) concentrations of M8, A549 cells were completely protected from influenza virus infection, whereas cells treated with WT, M5, or CL9 aptamer displayed detectable NS1 protein expression at 24 h after infection (FIG. 16F). Similarly, cells treated with M8 and then challenged with DenV were completely protected against infection (FIG. 16G). Production of IFN-γ within the supernatant of 5'-pppRNA-treated cells was 17.8-fold greater in M8-treated samples than in the WT, as measured by enzyme-linked immunosorbent assay (ELISA), and transfer of the supernatant from M8-treated A549 cells onto freshly seeded cells 24 h later inhibited dengue replication as efficiently as direct treatment of M8, suggesting that antiviral cytokine production is associated with the enhanced antiviral properties of M8. The 5'-triphosphate moiety was required to generate the antiviral response. In addition, M8 was not cytotoxic to A549 cells, since high concentrations of agonist did not reduce cell viability. Altogether, these results identify a 5'-pppRNA RIG-I agonist with enhanced antiviral activity against influenza virus and dengue virus infections.

Figure 17A:
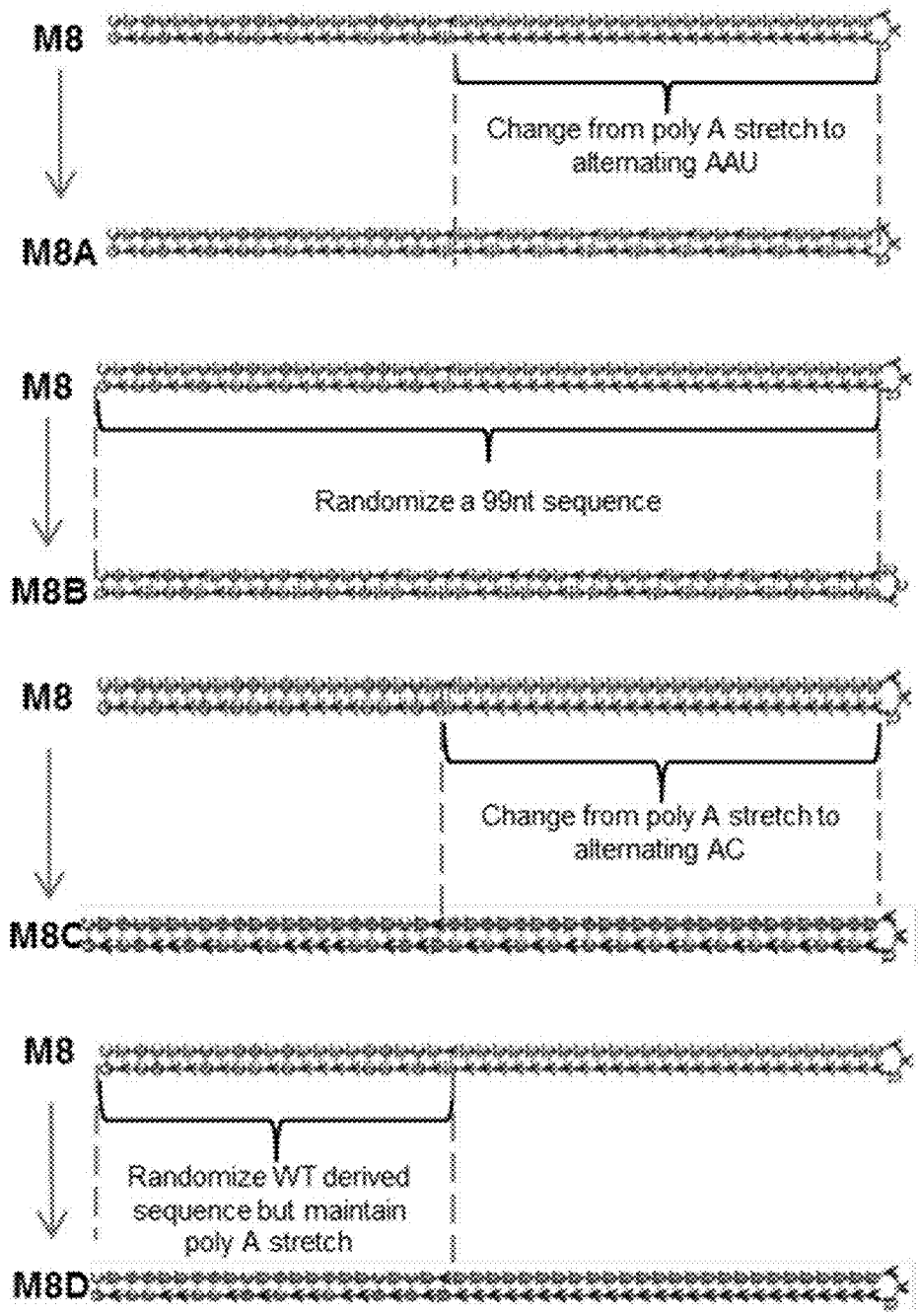
FIG. 17A is a schematic representation of modifications to the M8 5'pppRNA. Sequence changes were made to the poly AU base-pair stretch (MBA, M8C), the WT-derived blunt-end (M8D), and the entire sequence (M8B) while keeping the structure intact.
Figure 17B:
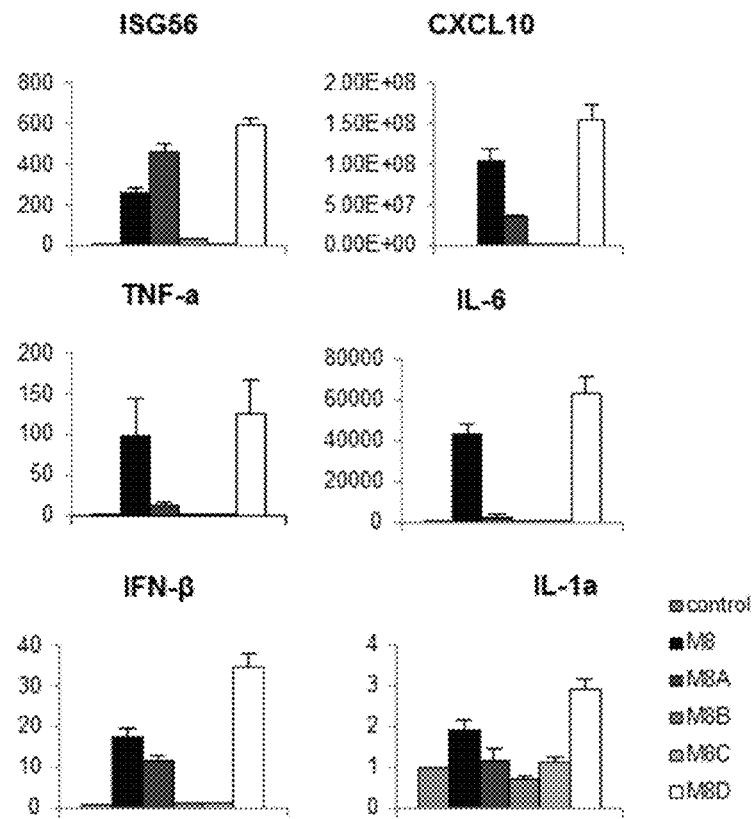
FIG. 17B is a set of bar graphs showing the results of A549 cells that were transfected with 5'pppRNA (1 ng/ml) using Lipofectamine RNAiMax®. After 24 h, cells were harvested and total mRNA was isolated. Antiviral and inflammatory gene expression was determined by qPCR. Data are from one experiment performed in triplicate and represent the means±SEM.
Figure 17C:
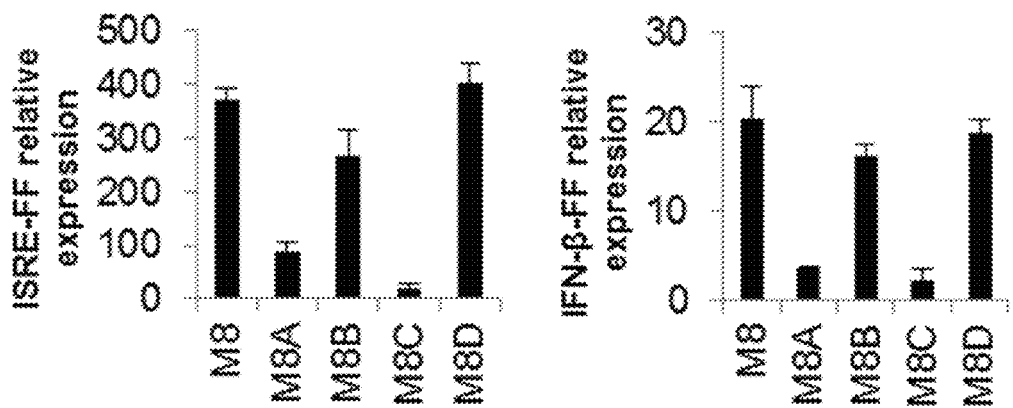
FIG. 17C is a set of bar graphs showing the results of HEK293T cells that were co-transfected ISRE or IFN-β promoter reporter plasmid (200 ng) along with 5'pppRNA (10 ng/ml). Luciferase activity was analyzed 24 h post-transfection by the Dual-Luciferase Reporter assay. Relative luciferase activity was measured as fold induction relative to the basal level of reporter gene. Data are from one experiment performed in triplicate and represent the means±SEM.
Figure 17D:
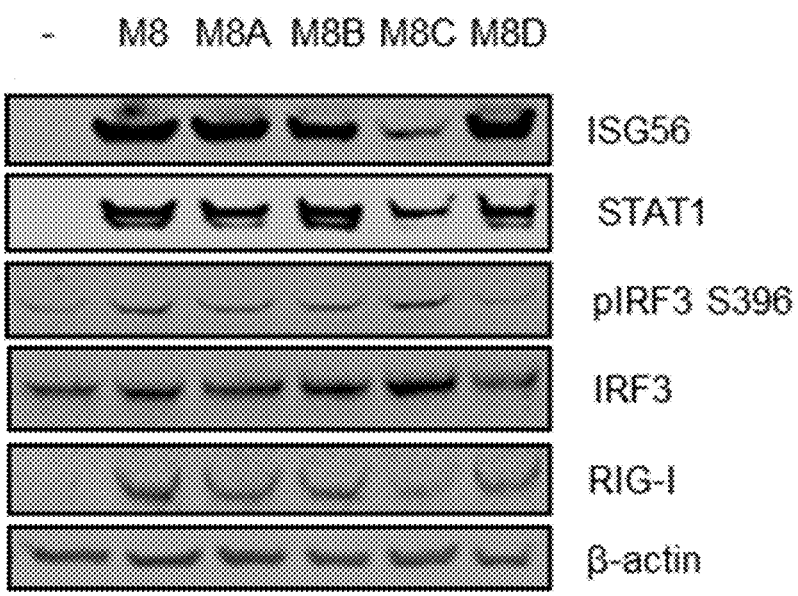
FIG. 17D is an image of an immunoblot showing the results of A549 cells that were transfected with 5'pppRNA (1 ng/ml) for 24 h. Whole cell extracts were prepared, resolved by SDS-PAGE, and analyzed by immunoblotting for ISG56, STAT1, pIRF3 S396, IRF3, RIG-I, and β-actin. One representative Western blot from one experiment is shown.
Figure 17E:
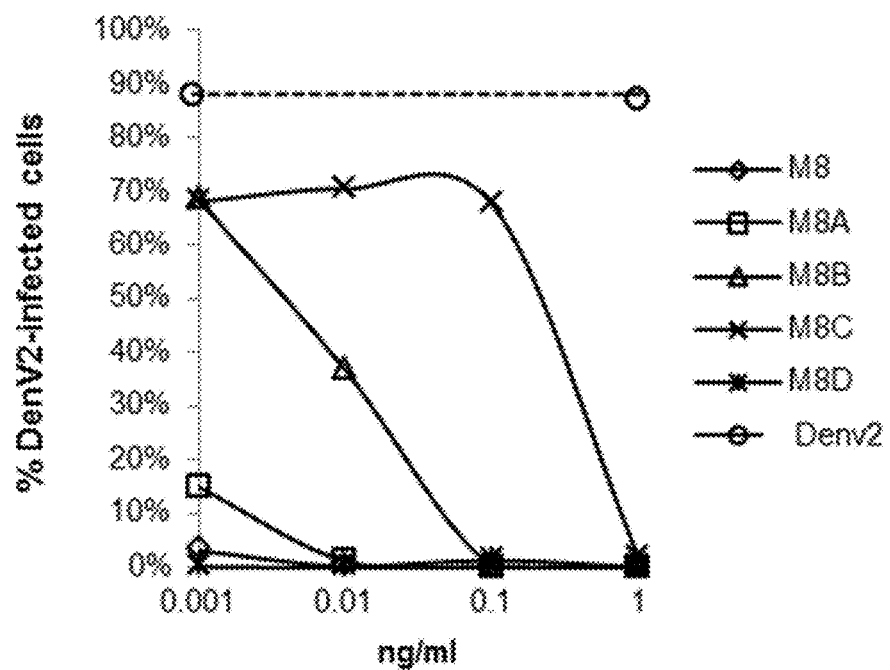
FIG. 17E is a plot showing the results of A549 cells that were transfected with 5'pppRNA (0.001-10 ng/ml) using Lipofectamine RNAiMax for 24 h then challenged with dengue virus (MOI 0.1) for 24 h. Percentage of infected cells was determined by intracellular staining of DENV E protein expression. Data are from one experiment performed in triplicate and represent the means±SEM.

Antiviral activity is dependent on RNA structure: The enhanced activity of M8 appeared to be the consequence of modification of sequence, length, and ultimately structure of the RNA. To examine whether sequence alone was sufficient to alter the antiviral and inflammatory activity, new sequence modifications that maintained the 99-nt looped structure were introduced into the M8 sequence (FIG. 17A). Substitution of the poly(U) stretch with alternating AAUs (M8A) or ACs (M8C), randomization of the entire 99-nt sequence (M8B), and randomization of the WT derived region while leaving the poly(U) stretch intact (M8D) all resulted in varied effectiveness. Those with no (M8D) or minor (M8A) changes to the poly(U) stretch maintained the inducibility of ISGs, as exemplified by increased expression of chemokines, cytokines (CXCL10, IL-6, IL-1α, and TNF-α), and inflammatory and antiviral mRNA (ISG56 and IFN-γ) (FIG. 17B). ISRE and IFN-γ relative activities of M8B and M8D measured by luciferase assay were comparable to those of the original M8 sequence (FIG. 17C). Although all variants were capable of inducing expression of ISG56, STAT1, and RIG-I, M8C had the lowest activity (FIG. 17D). Sequence modification alone was sufficient to alter viral inhibition properties (FIG. 17E). While M8, M8A, and M8D at 0.01 ng/ml completely abrogated DenV replication, the number of DenV positive cells was reduced to 35% and 70%, respectively, when M8B and M8C were used as RIG-I agonists. Further sequence modifications, including insertion of a CCC motif to the poly(U) region, replacement of the poly(U) region with alternating AAC, or introduction of AAAAA segments throughout the sequence, resulted in decreased antiviral and inflammatory activity (data not shown), thus demonstrating that the poly(U) moiety was critical for M8 activity.

Figure 18A:
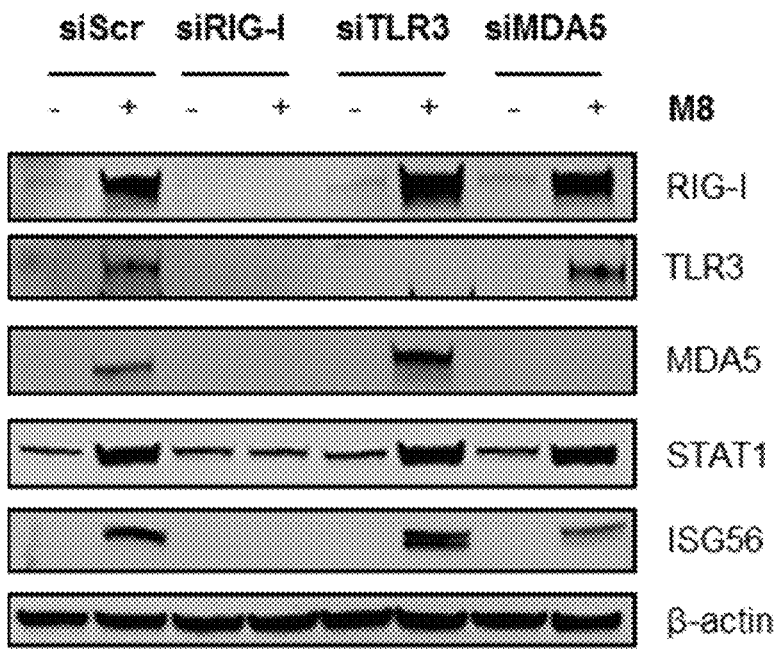
FIG. 18A is an image of an immunoblot showing the results of A549 cells that were transfected with control, RIG-I, TLR3, or MDA5 (30 pmol). After 48 h, M8 5'pppRNA (0.1 ng/ml) was transfected and 24 h after treatment, whole cell extracts were analyzed by SDS-PAGE and immunoblotted for RIG-I, TLR3, MDA5, STAT1, ISG56, and β-actin. One representative Western blot out of three independent triplicates is shown.
Figure 18B:
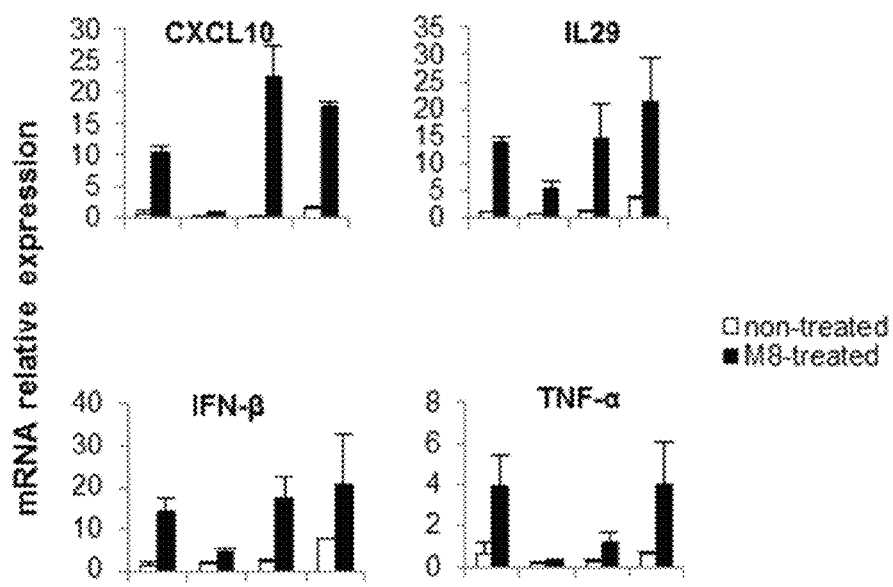
FIG. 18B is a set of bar graphs showing the results of A549 cells that were transfected with siRNA and M8 5'pppRNA as in (18A), and antiviral and inflammatory gene expression was determined by qPCR. Data are from one experiment performed in triplicate and represent the means±SEM.
Figure 18C:
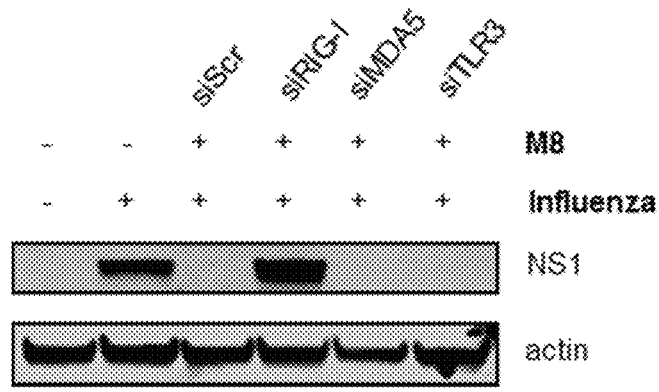
FIG. 18C is an image of an immunoblot showing the results of A549 cells were transfected with siRNA and M8 5'pppRNA as in (18A) then challenged with H3N2 Brisbane A/59/2007 (MOI 0.2) for 24 h. Whole cell extracts were prepared, analyzed by SDS-PAGE, and immunoblotted for influenza viral protein NS1 and β-actin. One representative Western blot out of three independent triplicates is shown.
Figure 18D:
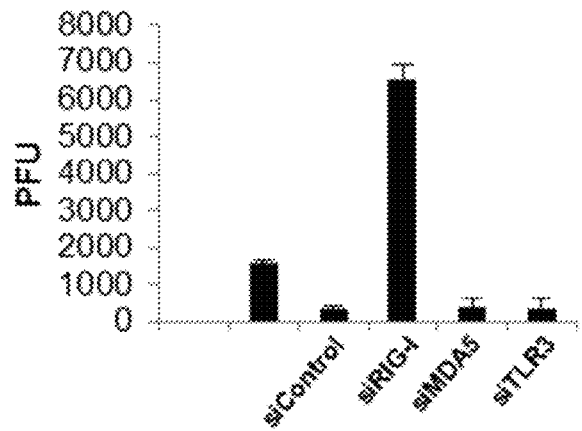
FIG. 18D is a bar graph of viral titers in cell culture supernatants as determined by plaque assay. Data are from two independent experiments performed in triplicate and represent the means±SEM.
Figure 18E:
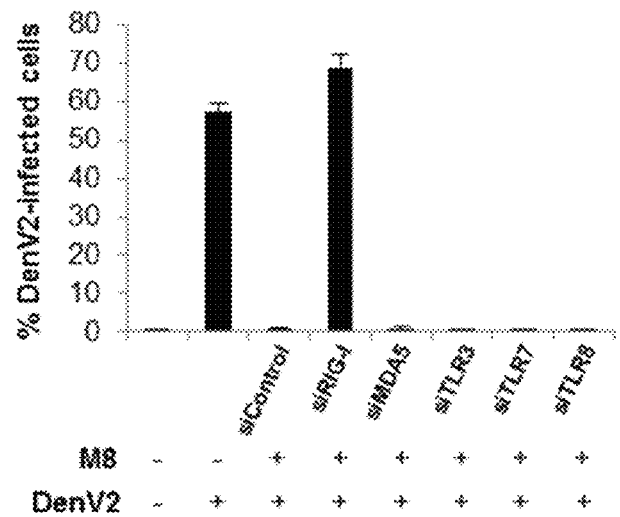
FIG. 18E is a bar graph showing the results of A549 cells that were transfected with siRNA for the indicated pattern recognition receptors and 5'pppRNA as in (18A) then challenged with dengue virus (MOI 0.1) for 24 h. Percentage of infected cells was determined by intracellular staining of DENV E protein expression. Data are from one experiment performed in triplicate and represent the means±SEM.
Figure 18F:
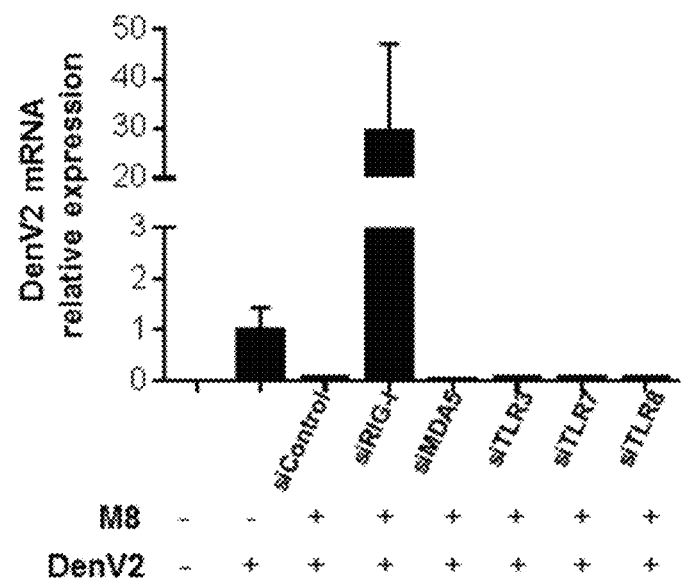
FIG. 18F is a bar graph showing the results of DenV mRNA from cells harvested from (FIG. 18E) that was quantified by qPCR. Data are from one independent experiment performed in triplicate and represent the means±SEM.

M8 Activity is dependent on functional RIG-I signaling: To ensure that the novel RNA agonist maintained specificity for the RIG-I pathway, siRNA directed against various RNA sensors was used to knock down RIG-I, TLR3, and MDA5, respectively. While MDA5 and TLR3 knockdown did not affect M8-mediated antiviral activity (FIG. 18A) as determined by immunoblot analysis of several ISGs, cells knocked down for RIG-I failed to induce a ISG56 or STAT1 response compared to siRNA control-treated cells. Additionally, RIG-I knockdown abolished TLR3 and MDA5 expression, suggesting an upstream regulatory activity of RIG-I on other pattern recognition receptors. In the absence of RIG-I, M8 was unable to induce secretion of type I and III interferon, CXCL10, or TNF-α, whereas MDA5 or TLR3 knockdown did not block antiviral and inflammatory activities (FIG. 18B). Moreover, RIG-I was required for M8-induced antiviral activity against influenza virus and dengue virus replication (FIGS. 18C to 18F), as determined by the diminished expression of influenza NS1 viral protein (FIG. 18C) and decreased DenV titer (FIG. 18D) in cells lacking RIG-I. The absence of RIG-I also resulted in an increase in viral protein compared to influenza virus-infected control cells, indicating that the loss of the RIG-I sensor enhanced viral replication. Additionally, to rule out the possibility that the poly(U)-rich moiety of M8 was recognized by TLR7 and TLR8, known targets of single stranded poly(U)-RNA molecules (Diebold S S et al, Science 303, 1529-1531 (2004); incorporated by reference herein), expression of these receptors was blocked. M8 was able to block DenV infection-based on evaluation of DenV 2E protein expression by ICS staining and by quantification of viral RNA (FIGS. 3E and F)—despite the absence of TLR7 and TLR8, Altogether, these data indicate that the M8 5'-pppRNA antiviral activity is RIG-I specific.

Figure 19A:
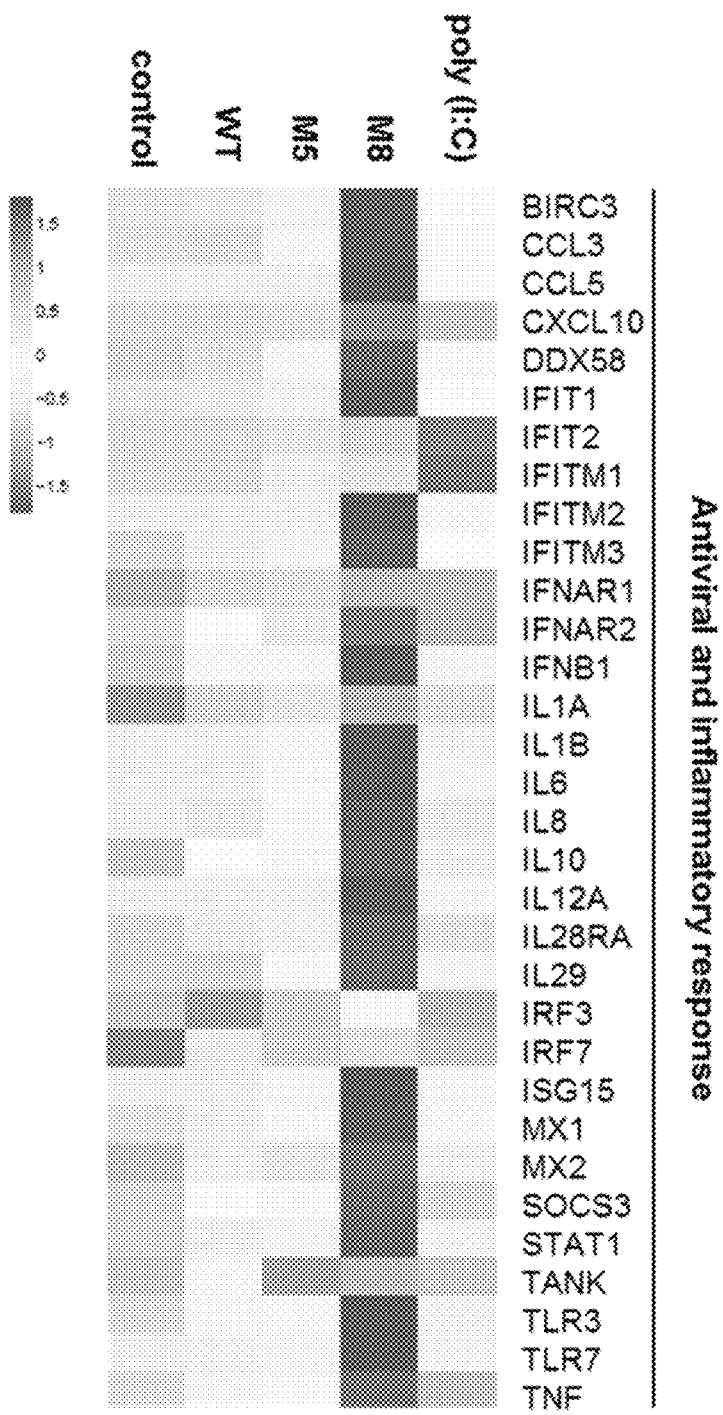
FIG. 19A is a heatmap showing the results of Mo-DCs that were transfected with 20 fmol of WT, M5, or M8 5'pppRNA or poly (I:C). After 24 h, samples were analyzed by high throughput analysis of gene expression by Fluidigm BioMark qPCR. Gene expression levels were calculated using the ΔΔCt method and gene-wise standardized expression (z-score) was generated for each gene. The scale represents z-score values where red shows an up-regulation and blue a down-regulation in gene expression. Heat map is representative of three individual donors.
Figure 19B:
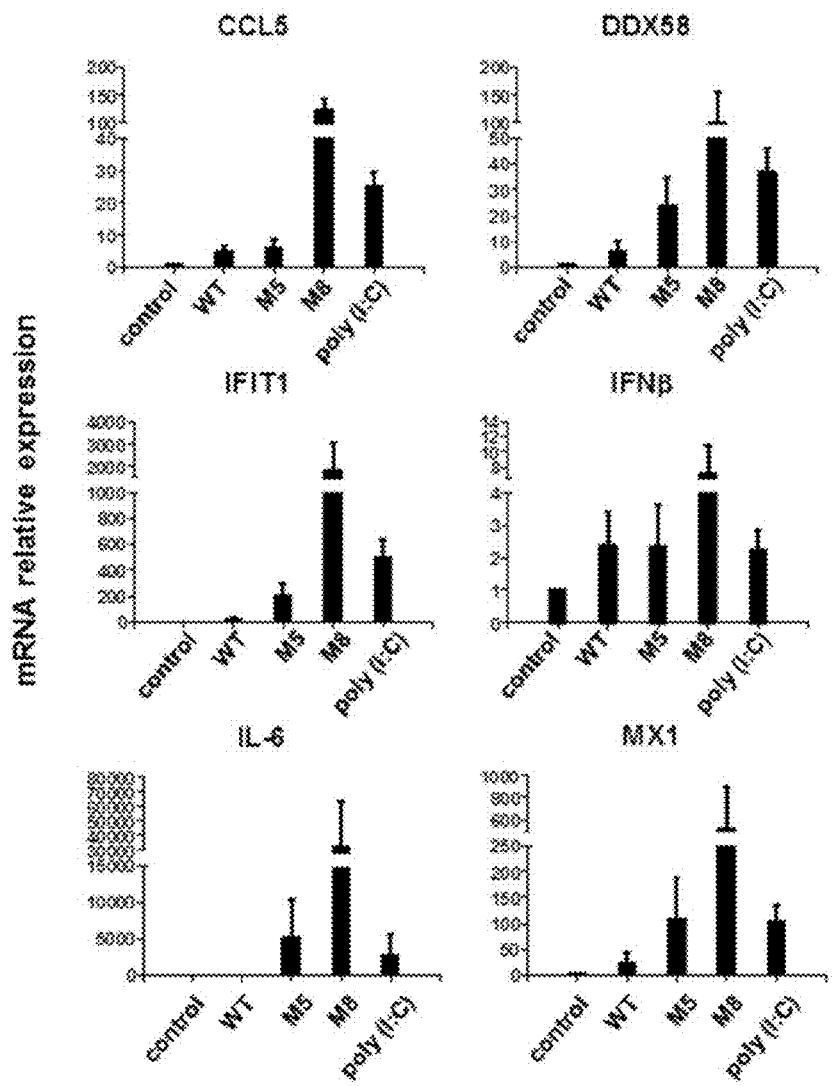
FIG. 19B is a set of bar graphs showing selected genes from BioMark qPCR analysis that are represented to show quantitative differences in RNA treatment. Data are from three independent experiments and represent the means±SEM.
Figure 19C:
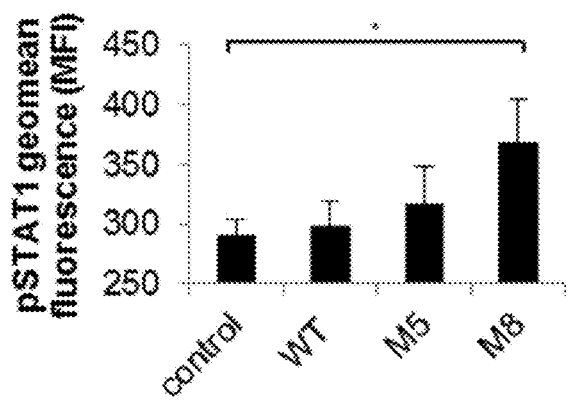
FIG. 19C is a bar graph showing the results of Mo-DCs that were transfected with WT, M5, or M8 5'pppRNA (10 ng/ml) for 24 h. pSTAT1 expression is represented as geomean fluorescence as measured by flow cytometry analysis. Data are from one independent experiment performed in triplicate and represent the means±SEM.
Figure 19D:
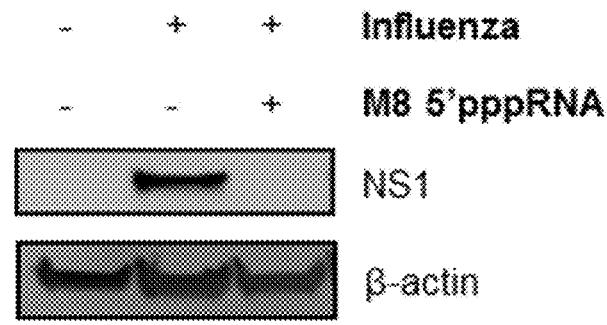
FIG. 19D is an image of an immunoblot showing the results of Mo-DCs were transfected with M8 5'pppRNA (10 ng/ml) for 24 h then challenged with influenza H3N2 Brisbane A/59/2007 (MOI 2) for 24 h. Whole cell extracts were prepared, analyzed by SDS-PAGE, and immunblotted for influenza viral protein NS1 and β-actin. One representative Western blot from one experiment is shown.
Figure 19E:
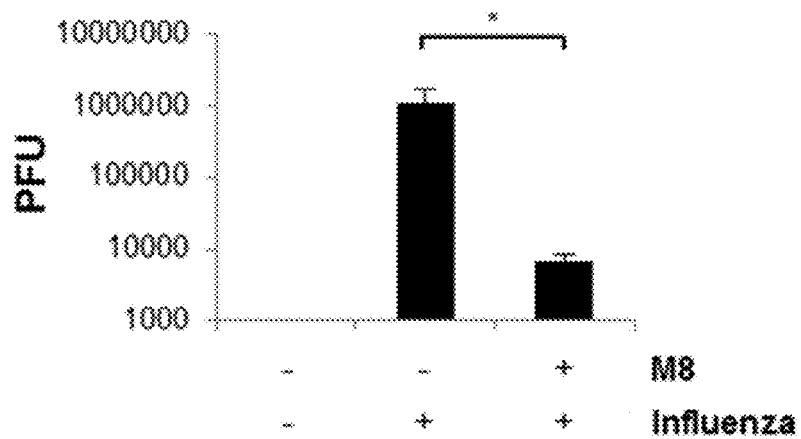
FIG. 19E is a bar graph of viral titers in cell culture supernatants that were determined by plaque assay. Data are from one experiment performed in triplicate and represent the means±SEM.
Figure 19F:
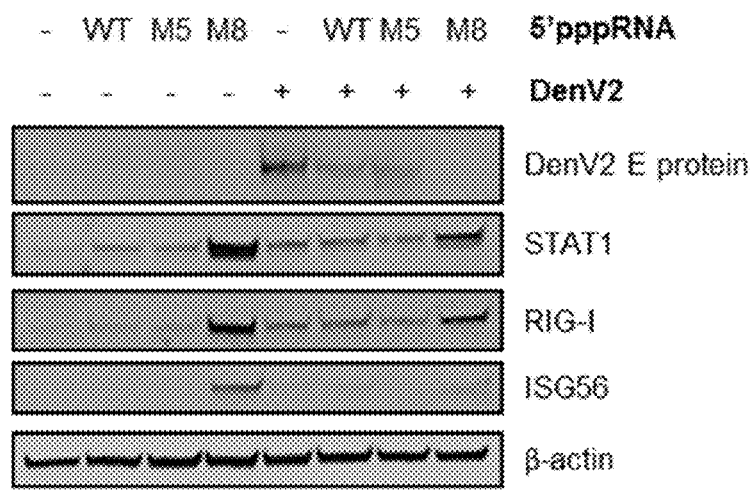
FIG. 19F is an image of an immunoblot showing the results of human monocyte-derived dendritic cells (Mo-DCs) that were transfected with WT, M5, or M8 5'pppRNA (10 ng/ml) using HiPerFect transfection reagent for 24 h then challenged with dengue virus (MOI 10). Whole cell extracts were prepared, analyzed by SDS-PAGE, and immunoblotted for DenV viral E protein, STAT1, RIG-I, ISG56, and β-actin. One representative Western blot from one experiment is shown.

M8 activates greater breadth and intensity of innate immune response: The response elicited by the optimized M8 RIG-I agonist was examined using monocyte-derived dendritic cells (Mo-DCs) transfected with RIG-I agonists at equimolar doses and examined induction of antiviral and inflammatory genes and inhibition of viral replication. Using a customized high-throughput BioMark chip, nearly all genes selected in a panel of antiviral and inflammatory genes, including type I interferons (IFNβ 1), type III interferons (IL28RA and IL-29), proinflammatory cytokines and chemokines (CCL5, IL1B, and IL-6), and interferon-stimulated genes (DDX56, IFIT1, ISG15, and MX1), were upregulated by M8 (FIG. 19A). Selected genes from the BioMark chip are represented in FIG. 19B. Induction of inflammatory markers was accompanied by an increase in pSTAT1, as measured by flow cytometry (geomean fluorescence [P=0.03]) (FIG. 19C). M8 inhibited influenza virus replication in Mo-DCs, as exhibited by a decrease in NS1 protein (FIG. 19D) and a 2-log-fold decrease in viral titer (FIG. 19E), recapitulating the results observed in A549 cells. Dengue viral replication was completely inhibited in M8-treated cells, whereas WT and M5 at the same concentration reduced but did not completely eliminate DenV E protein expression (FIG. 19F). Increased expression of STAT1, RIG-I, and ISG56 in M8-treated Mo-DCs accompanied the inhibition of dengue viral protein expression (FIG. 4F). Altogether, these results emphasize that both the intensity and the breadth of antiviral gene expression were increased dramatically in M8-treated primary human DCs, compared to treatment by other RNA agonists.

Figure 20A:
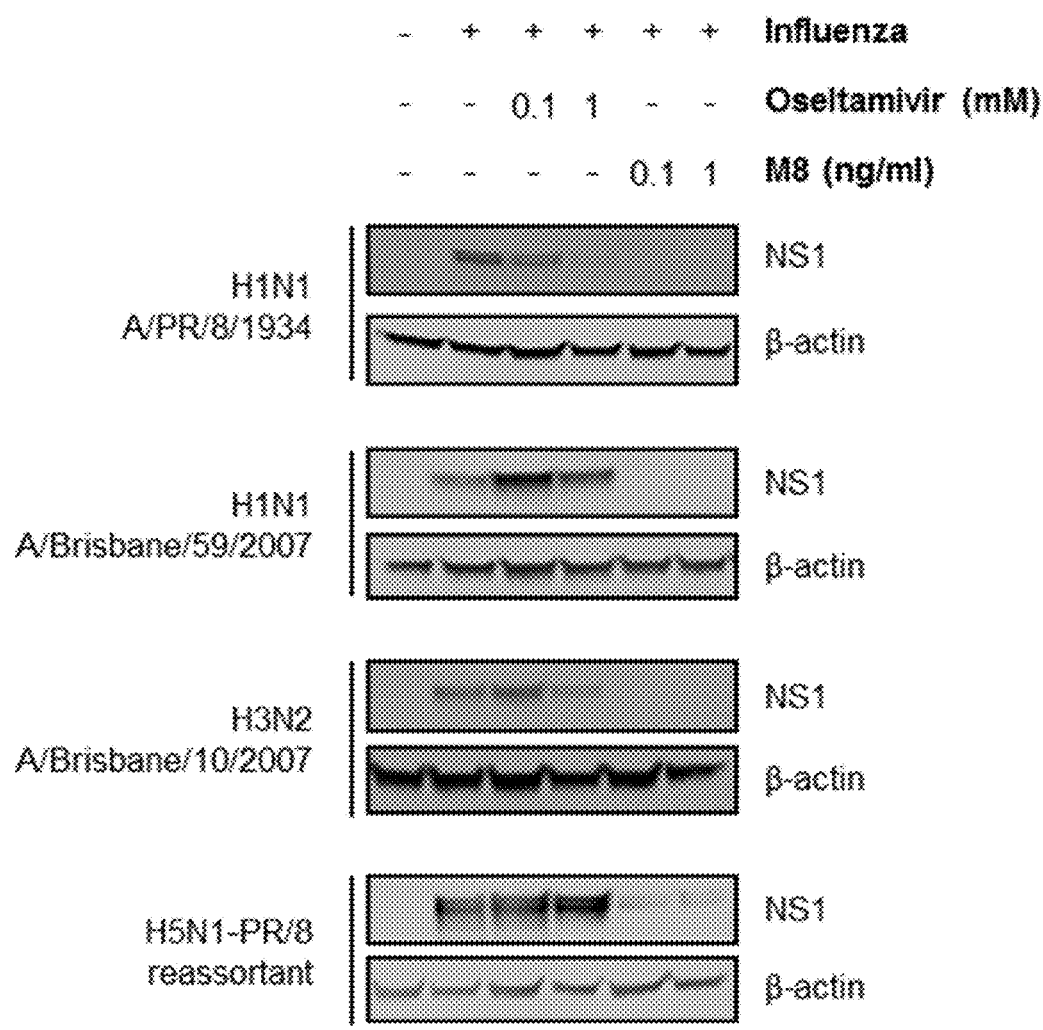
FIG. 20A is an image of an immunoblot showing the results of A549 cells that were treated with oseltamivir phosphate (0.1 or 1 mM) or transfected with M8 5'pppRNA (0.1 or 1 ng/ml) for 24 h then challenged with the indicated strains of influenza (MOI 2). Whole cell extracts were prepared 24 h post-infection, subjected to SDS-PAGE, and probed with antibodies for influenza viral protein NS1 and β-actin. One representative Western blot out of two independent experiments is shown.

M8 possesses enhanced antiviral activity against multiple strains of influenza virus compared to oseltamivir: As shown in FIG. 16F, M8 5'-pppRNA efficiently blocked H1N1 influenza virus A/Puerto Rico/8/1934 at concentrations 100-fold and 10-fold lower than those of the WT and M5, respectively. The capacity of the M8 agonist to inhibit three different pandemic and seasonal influenza A virus strains (H1N1 A/Brisbane/59/2007, H3N2 A/Brisbane/10/2007, and H5N1-PR/8 reassortant) in addition to H1N1/A/PR/8/1934, was evaluated. Some of the strains are resistant to oseltamivir, an FDA-approved antiviral drug for influenza virus and the current standard of care. Nearly all H1N1 A/Brisbane/59/2007-like strains have been reported to be resistant to oseltamivir due to an H274 mutation within the neuraminidase gene (Centers for Disease Control and Prevention, Morb Mortal, Wkly Rep 58, 115-119 (2009); incorporated by reference herein), while other strains remain susceptible to oseltamivir. Interestingly, all four influenza virus strains were either not inhibited or partially inhibited by oseltamivir, whereas M8 treatment of influenza virus-infected cells with M8 at a significantly lower molarity (~20 fmol) completely inhibited NS1 protein expression (FIG. 20A). Correspondingly, replication of the oseltamivir-resistant influenza virus strain, as measured by plaque assay, indicated that oseltamivir-treated cells were unable to reduce viral titer, whereas M8 at concentrations as low as 0.1 ng/ml reduced viral titer by ~2-log-fold (FIG. 20B, top right). Although the other three strains were susceptible to oseltamivir, only cells treated with M8 showed significantly reduced viral titers. These results indicate that M8 exhibits an enhanced broad-range antiviral activity against multiple unrelated influenza strains, including a drug-resistant strain of influenza virus.

Figure 21A:
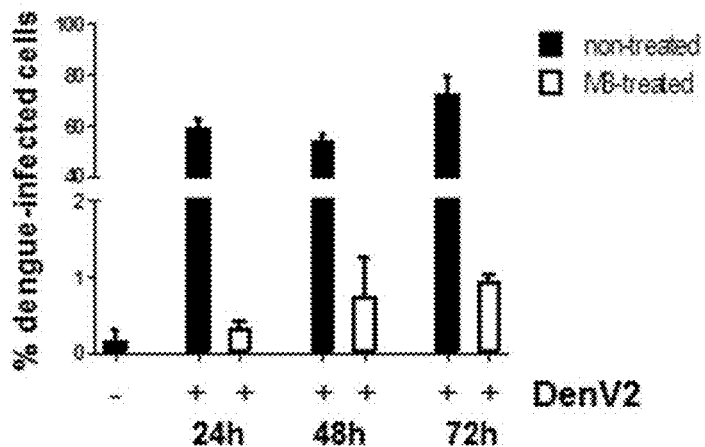
FIG. 21A is a bar graph of the results of A549 cells that were transfected with M8 5'pppRNA (1 ng/ml) for 24 h then challenged with dengue virus (MOI 0.5). Percentage of infected cells was determined 24, 48, and 72 h post-infection by intracellular staining of DENV E protein expression. Data are from one experiment performed in triplicate and represent the means±SEM.
Figure 21B:
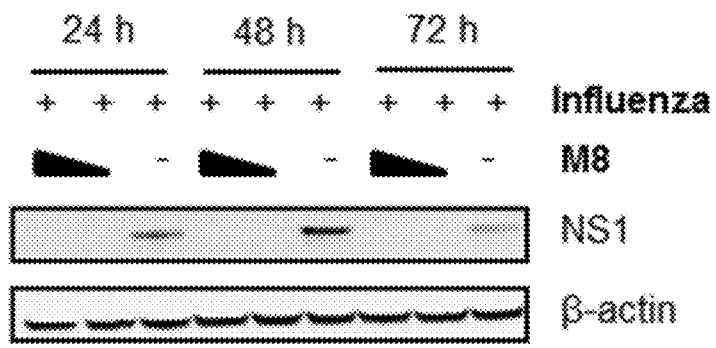
FIG. 21B is an image of an immunoblot showing the results of A549 cells that were transfected with 5'pppRNA (0.1, 1 ng/ml) for 24 h then challenged with H3N2 Brisbane 59/2007 (MOI 0.2). Whole cell extracts were prepared at different times after transfection (24, 48, 72 h), subjected to SDS-PAGE, and probed with antibodies for influenza viral protein NS1 and β-actin. One representative Western blot out of three independent triplicates is shown.
Figure 21C:
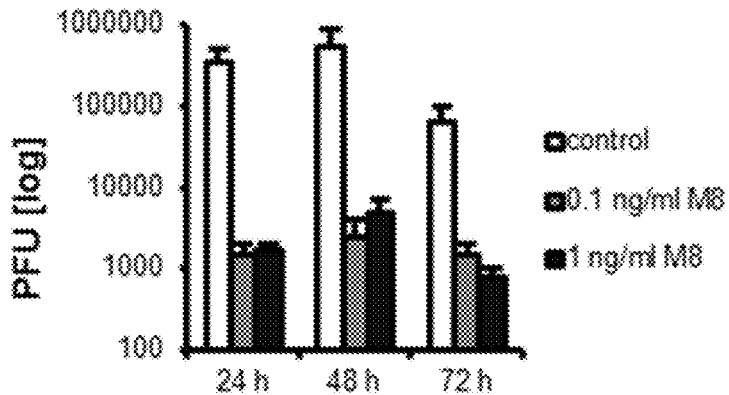
FIG. 21C is a bar graph showing viral titers in cell culture supernatants that were determined by plaque assay. Data are from two independent experiments performed in triplicate and represent the means±SEM.
Figure 21D:
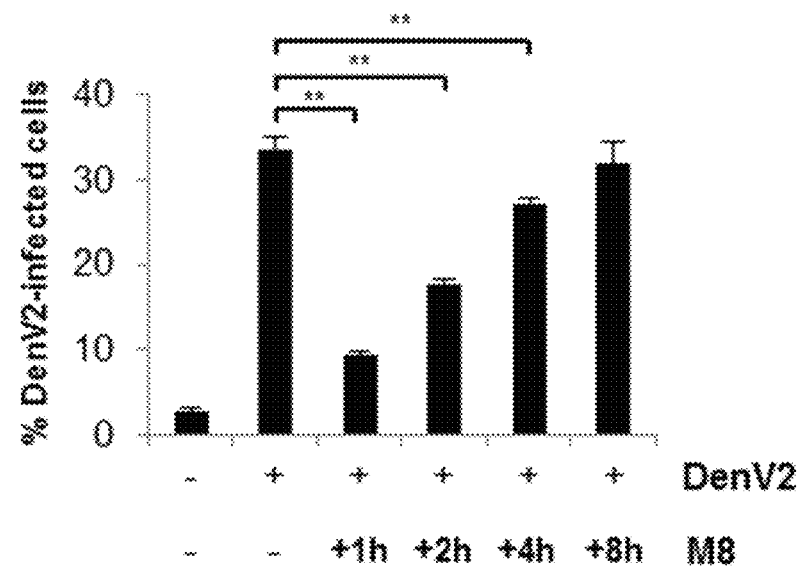
FIG. 21D is a bar graph showing the results of A549 cells that were infected with dengue (MOI 0.1) for 1 h then transfected with M8 5'pppRNA (0.01 ng/ml) at 1, 4, and 8 h post infection. Percentage of infected cells was determined 24 h post-infection by intracellular staining of DENV E protein expression.
Figure 21E:
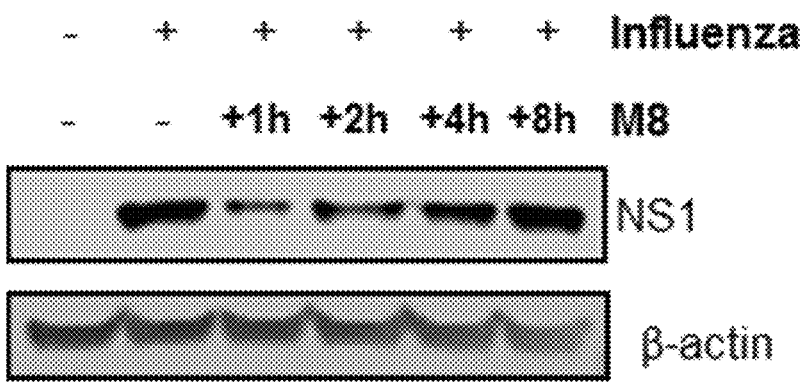
FIG. 21E is an image of an immunoblot showing the results of Mo-DCs that were infected with influenza (MOI 0.2) for 1 h followed by transfection of M8 5'pppRNA at 1, 2, 4, and 8 h post-infection. Whole cell extracts were prepared 24 h post-infection, subjected to SDS-PAGE, and probed with antibodies for NS1 and β-actin. One representative Western blot out of three independent triplicates is shown.

Prophylactic and therapeutic administration of M8 protects against viral replication: To ensure that M8 provided long-lasting protection against infection, cells treated with M8 were infected with influenza virus or DenV for up to 72 h. At 3 days postinfection, cells were still protected from viral infection, indicating that M8 had extended antiviral activity (FIGS. 21A to 21C). Additionally, viral replication was significantly controlled when M8 was transfected therapeutically, up to 4 h postinfection (FIGS. 21D and 21E), although prophylactic treatment was most effective at blocking viral replication. Cells infected with DenV had the lowest percentage of infected cells when they were treated with M8 immediately following a 1-h infection period, with an increase of infected cells with each subsequent treatment (FIG. 21D). At 1 hour postinfection, the percentage of DenV-positive cells was reduced from 33.7% to 9.3%, followed by increases in infected cells to 17.7%, 27.3%, and 32.0% at 2, 4, and 8 h postinfection, respectively. In the context of influenza virus infection, NS1 expression occurred at 1 hour postinfection with an increase in NS1 viral protein expression as time progressed (FIG. 21E), recapitulating the results established in the DenV model. These results further characterize the protective nature of M8 as both prophylactic and therapeutic, resulting in a sustained antiviral protection and prevention of viral spread over time.

Figure 22A:
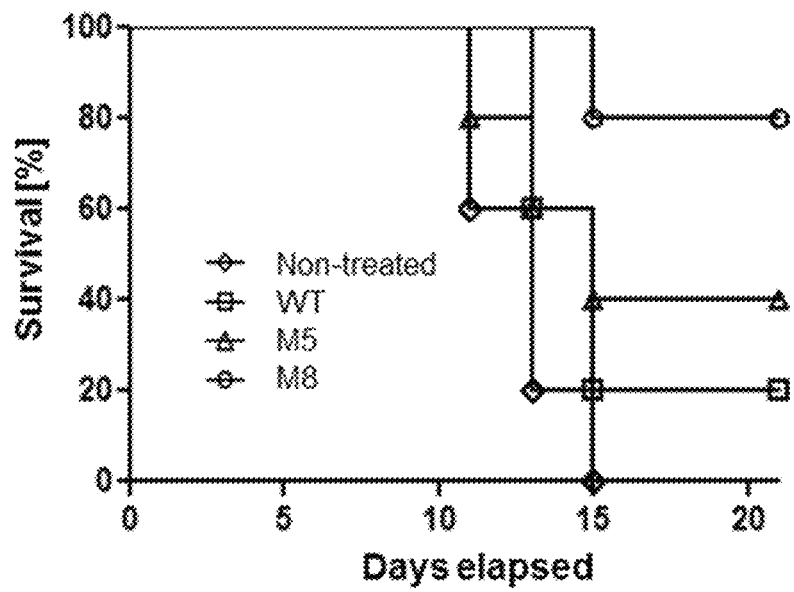
FIG. 22A is a plot showing the survival of BALB/c mice (n=5) that were injected IV with 5 μg of WT, M5 or M8 5'pppRNA complexed with in vivo-JetPEI one day prior to and on the day of infection with H5N1-RE influenza (5,000 PFU).
Figure 22B:
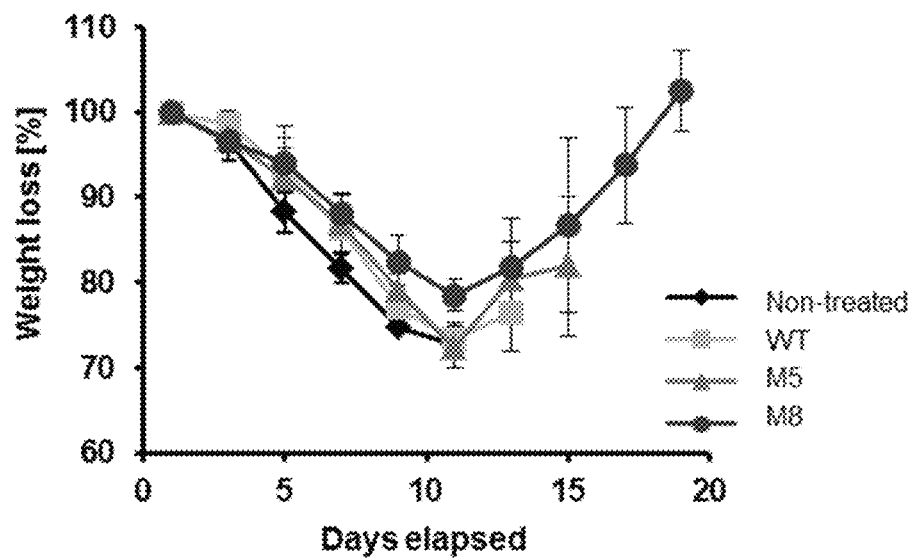
FIG. 22B is a plot showing the weight loss of BALB/c mice treated as in FIG. 22A.
Figure 22C:
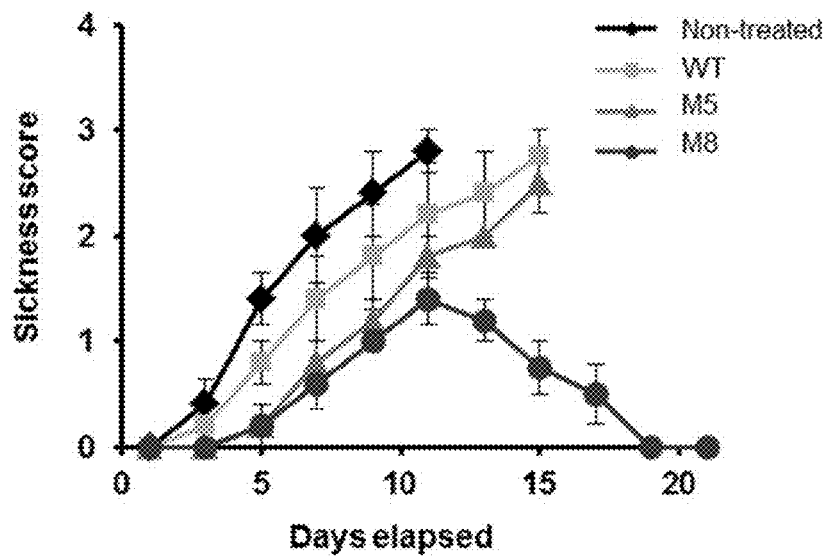
FIG. 22C is a plot showing the sickness score of BALB/c mice treated as in FIG. 22A.
Figure 22D:
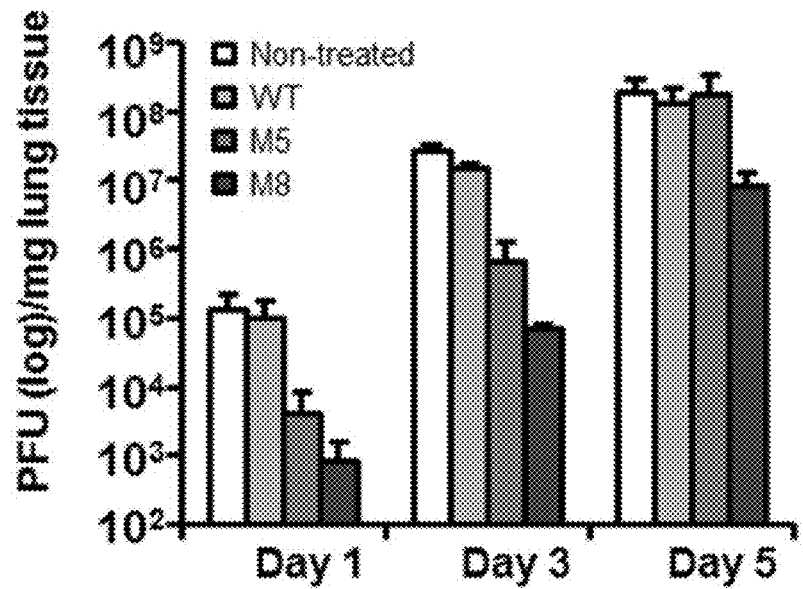
FIG. 22D is a bar graph showing the results of H5N1-RE viral replication in lungs of animals treated with WT, M5 or M8 was quantified by plaque assay at days 1, 3 and 5. Error bars indicate SEM for five animals.

M8 5'-pppRNA protects mice from lethal influenza virus and chikungunya virus infection: To determine the antiviral properties of M8 in vivo, an equal amount of WT, M5, or M8 5'-pppRNA was injected intravenously 24 h prior to and on the day of lethal H5N1-reassorted influenza virus challenge. Untreated, infected mice succumbed to influenza infection by day 15, while at day 20, at least some mice from each 5'-pppRNA treatment group survived; animals treated with M8 had the highest survival rate (80%), compared to those mice in the WT and M5 treatment groups (20% and 40%, respectively) (FIG. 22A). Statistical significance was achieved between the nontreated and M8 groups (log rank test for trend; P_0.0124). All groups experienced weight loss, with a rebound at day 11; however, animals treated with M8 5'-pppRNA experienced a delay in the onset of weight loss and lost less weight compared to the control group (FIG. 22B). Although the M8 group showed symptoms of influenza-like illness, as determined by appearance and activity, the onset of symptoms was delayed and symptoms were milder compared to the other treatment groups, and mice recovered fully (FIG. 22C). Finally, lung viral titers as determined by plaque assay revealed a 2-log decrease in viral replication in M8-treated mice, a 1.5-log decrease in M5-treated mice, and almost no difference in WT-treated mice 1 day postinfection compared to controls (FIG. 22D). At 3 and 5 days postinfection, lung viral titers increased across all groups, but the lowest virus titers were observed in mice treated with M8.

Figure 22E:
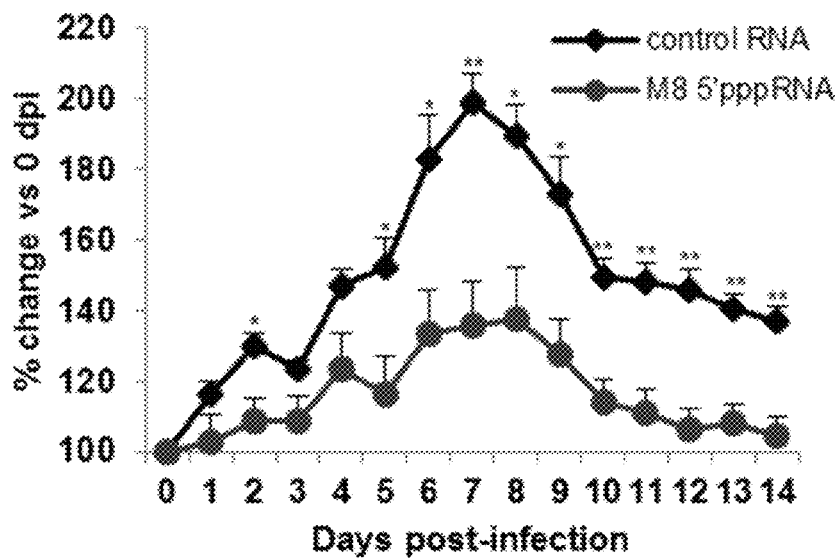
FIG. 22E is a plot showing the results where control RNA or M8 5'pppRNA (2 μg) complexed with in vivo JetPEI was injected intramuscularly into adult mice on the day prior to and day of viral infection. Mice were infected with chikungunya via footpad injection. Footpad swelling was monitored and measured daily by caliper during the course of 14 days.
Figure 22F:
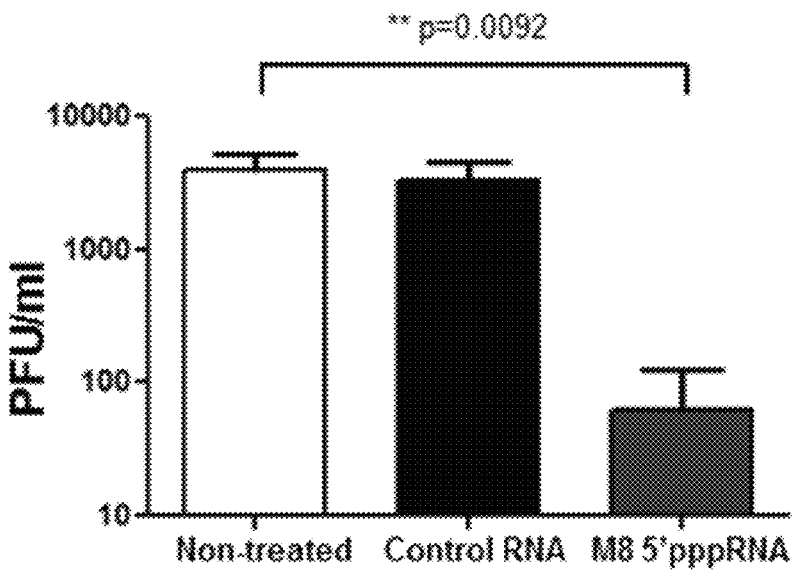
FIG. 22F is a bar graph of serum viral load at day 3 for the animals treated as described in FIG. 22E.

In complementary in vivo studies, a chikungunya virus (CHIKV) infection model (Pal P et al, J Virol 88, 8213-8226 (2014); incorporated by reference herein) was used to examine the antiviral effect of M8 on chikungunya-associated footpad swelling and viremia as well as surrogate markers for CHIKV arthritis and pathogenesis. Over 14 days, the percent change in foot swelling, a phenotypic result of viral infection, was reduced in mice treated with M8, while footpad swelling in untreated mice peaked at day 7 (FIG. 22E). Analysis of viral RNA in serum revealed an ~1.5-log decrease in virus titer in M8-treated mice versus control RNA-treated mice (FIG. 22F). These data demonstrate that prophylactic treatment with low-dose M8 5'-pppRNA protected mice from lethal influenza virus infection, reduced CHIKV induced arthritic swelling, and reduced viral yield of both viruses by 1 to 2 logs, compared to other treatment groups.

Stimulation of the evolutionarily conserved RIG-I pathway using optimized RIG-I agonists to induce antiviral, inflammatory, and immune modulatory gene networks is an attractive strategy for the development of novel antiviral compounds. Indeed, several studies have shown that nucleic acids, such as antisense oligonucleotides and siRNA, are promising agents for highly pathogenic RNA viruses, such as influenza virus, Ebola virus, and West Nile virus (Spurgers K B et al, Antiviral Res, 78, 26-36 (2008); incorporated by reference herein), yet many are restricted to targeting steps of viral replication and do not exploit the innate immune response of the host. Furthermore, RIG-I agonists have the advantage of dual functionality, acting as a specific sensor that triggers the innate immune response and as a direct antiviral factor which can counteract the interaction of polymerase with pregenomic RNA in response to HBV infection (Sato, 2015 supra), suppressing viral replication. The ability to inhibit viral replication of dengue, influenza, and chikungunya viruses in vitro and in vivo highlights the efficacy of M8 5'-pppRNA and potential development of an RNA-based therapeutic.

It was previously demonstrated that a 5'-pppRNA derived from the 5' and 3' UTRs of the VSV genome blocked replication of a broad spectrum of viruses and stimulated a large and unique transcriptome profile of inflammatory and antiviral genes (27, 28). We hypothesized that a rationally designed RNA agonist with enhanced antiviral activity could be constructed through deliberate sequence and structure alterations while maintaining the necessary requirements of a RIG-I ligand. In the initial generation of RIG-I agonists, a 59-nucleotide hairpin structure with maximal complementarity and free of loops, termed M5, was found to enhance cytokine production and inhibit viral replication compared to the original WT when human epithelial lung cells were pretreated with the RNA. An RNA sequence with similar structure but shorter length (M4) was the least effective of the newly modified sequences, confirming that a minimum length is required for RIG-I stimulation (Binder M et al, J Biol Chem 286, 27278-27287 (2011); Kato H et al, J Exp Med 205, 1601-1610 (2008); Patel J R et al, EMBO Rep 14, 780-787 (2013); and Uzri D and Gehrke L, J Virol 83, 4174-4184 (2009); all of which are incorporated by reference herein. However, further elongation of the M5 sequence enhanced the inflammatory and antiviral properties 2 log-fold compared to the WT (FIG. 16). At concentrations as low as 10 pg/ml, M8 completely abrogated dengue virus and influenza virus replication, and at comparable concentrations, M8 strongly induced cytokines and antiviral genes.

In primary human dendritic cells, replication of both dengue and influenza viruses was inhibited when cells were pretreated with 5'-pppRNA, accompanied by the induction of virtually all antiviral and inflammatory genes screened by high-throughput quantitative PCR (qPCR). Previously we showed that WT 5'-pppRNA induced a unique transcriptome profile compared to IFN-α-2b treatment, including the upregulation of CCL3, CCL5, IL-29, CXCL10, and IL-6 (Goulet et al, 2013 supra). M8 induced a striking antiviral response compared to WT treatment (FIGS. 19A and 19B), suggesting that M8 functions to broadly activate the innate immune response even in the absence of viral infection. In contrast to the previously published study (Goulet et al, 2013 supra), here we used considerably lower concentrations of M8 to induce a more robust inflammatory response compared to the original WT 5'-pppRNA. Induction of an antiviral response was increasingly heightened between the 59-nucleotide M5 and the 99-nucleotide M8, again highlighting the importance of RNA length to activate RIG-I. Additionally, the immense upregulation of the expression of nearly all type I and III interferons, inflammatory cytokines and chemokines, and interferon-stimulated genes tested suggests that M8 induces a complete interferon response in preparation of viral infection. Additionally, this robust triggering of the innate immune response resulted in a concomitant antiviral protection in A549 cells (FIGS. 16A-16G) and Mo-DCs (FIGS. 19A-19F). The enhanced antiviral properties of M8 in vitro were confirmed in vivo, as M8 administration increased survival of mice challenged with a lethal dose of influenza virus and decreased viral titers in influenza virus- and chikungunya virus-infected mice (FIGS. 22A-22F).

Prophylactic administration of M8 not only enhanced viral inhibition in vitro and in vivo compared to the prototype VSV derived WT 5'-pppRNA but also surpassed the antiviral activity of oseltamivir, the current standard of care for influenza. Due to concerns about widespread resistance of circulating influenza viruses to current antiviral drugs such as zanamivir and oseltamivir, the constant need to monitor influenza virus strains for these changes in resistance and, more importantly, to develop novel, more effective treatments without side effects remains. M8 reduced viral protein expression and titers of a known oseltamivir-resistant strain, H1N1 A/Brisbane/59/2007, at a low concentration (FIGS. 20A and 20B), indicating that it would be an effective therapeutic to control viral infection of drug-resistant strains.

One of the more interesting conclusions of these studies is the apparent role that sequence plays in enhancing antiviral activity. Others have shown differences in activity with regard to RNA origin, motifs, length, and structure, whereas the effect of primary RNA sequence has not been considered. Primary sequence modification was sufficient to differentially trigger an innate response, although increased length of the sequence via additional UA pairings also enhanced the response. It has been reported that a poly(U) motif is required to produce an interferon response that establishes an antiviral state (Hwang S Y et al, Nucleic Acids Res 40, 2724-2733 (2012); incorporated by reference herein), and others observed enhanced activity with a poly (U) sequence, although they determined that it was not necessary to elicit a response (Uzri and Gehrke 2009 supra; Saito T et al, Nature 454, 523-527 (2008); and Schnell G et al, PLoS Pathog 8, e1002839 (2012); both of which are incorporated by reference herein). However, RIG-I-mediated immunity is not dependent on this specific moiety, as a number of RNA molecules trigger RIG-I without it. Here we reveal that RNA disruption of any part of the poly(U) sequence reduced antiviral and inflammatory activity, suggesting a crucial role for the poly(U) moiety in RNA-RIG-I binding (FIG. 17A-17E).

The results described in this study demonstrate that 5'-pppRNA can be rationally designed to achieve a maximal RIG-I mediated protective antiviral response against a number of RNA viruses, including influenza strains not inhibited by oseltamivir, in vitro. In vivo studies demonstrate that novel RIG-I agonists reduced viral load and improved survival of animals when they were treated with the 5'-pppRNA and then subsequently infected with influenza virus or chikungunya virus. The current global need for antiviral treatment persists, as there is presently no cure for dengue or chikungunya virus infections and current treatments for influenza are often ineffective and can produce harmful side effects.

Additionally, the compositions described herein can be used as a vaccine adjuvant Ichinohe T et al, J Virol 79, 2910-2919 (2005); Kulkarni R R et al, J Virol 88, 13990-14001 (2014); and Martinez-Gil L et al, J Virol 87, 1290-

1300); all of which are incorporated by reference herein) and could fill the growing need for novel therapeutics against infectious diseases.

Materials and methods: In vitro transcription and gel analysis. RIG-I agonists were synthesized by designing complementary forward (F) and reverse (R) primers with a T7 promoter (Integrated DNA Technologies). Primers are exemplified by SEQ ID NOs: 18-43. Primers were annealed then synthesized with an in vitro transcription kit (Ambion) for 16 h. RNA transcripts were DNase digested for 15 min at 37° C. and then purified with an miRNeasy kit (Qiagen). RNA was analyzed on a denaturing 15% Tris-borate-EDTA (TBE)-urea polyacrylamide gel (Bio-Rad) following digestion with 50 ng/µl of RNase A (Ambion) or 100 mU/µl of DNase I (Ambion) for 30 min. Control wild-type RNA is the dephosphorylated form of the WT sequence purchased from IDT. Secondary structure was predicted using the RNAfold Webserver (University of Vienna).

Cell culture, transfections, and luciferase assays: Lung epithelial A549 cells were grown in F12K (ATCC) supplemented with 10% fetal bovine serum (FBS) (Access Cell Culture). Transfection of RNA and small interfering RNA (siRNA) in A549 cells was performed with Lipofectamine RNAiMax® (Invitrogen) for 18 to 24 h and 48 h, respectively. Transfections of RNA and siRNA in monocyte-derived dendritic cells (Mo-DCs) were performed with HiPerFect transfection reagent (Qiagen). Poly(I•C) LMW was purchased from Invivogen. For siRNA knockdown, A549 cells were transfected with 30 pmol of control siRNA (sc-37007), human RIG-I (sc-61480), TLR3 (sc-36685), MDA5 (sc-61010), TLR7 (sc-40266), or TLR8 (sc-40268) (Santa Cruz Biotechnologies) using Lipofectamine RNAiMax according to the manufacturer's guidelines. For luciferase assays, 200 ng IFN-γ/pGL3 and 100 ng pRL-TK plasmids were cotransfected with 5'-pppRNA using Lipofectamine RNAiMax for 24 h. Reporter gene activity was measured by a dual-luciferase reporter assay (Promega) according to the manufacturer's instructions. Relative luciferase activity was measured as fold induction. Oseltamivir was purchased from AvaChem Scientific.

Monocyte isolation and differentiation into monocyte-derived dendritic cells: Human peripheral blood mononuclear cells (PBMC) were isolated from buffy coats of healthy, seronegative volunteers in a study approved by the institutional review board (IRB) and by the Vaccine & Gene Therapy Institute of Florida (VGTI-FL) Institutional Biosafety Committee (2011-6-JH1). Written informed consent approved by the VGTI-FL, Inc., ethics review board (FWA number 161) was provided to study participants. Research conformed to ethical guidelines established by the ethics committee of the Oregon Health and Science University (OHSU), VGTI, and Martin Health System. Briefly, PBMC were isolated from freshly collected blood using Ficoll-Paque Plus medium (GE Healthcare Bio) as per the manufacturer's instructions. CD14 monocytes were isolated by positive selection using CD14 microbeads and a magnetic cell separator as per kit instructions (Miltenyi Biotech). Purified CD14 monocytes were cultured for 7 days in 100-mm dishes ($15 \times 10^6$ cells) in 10 ml of complete monocyte differentiation medium (Miltenyi Biotech). On day 3, the medium was replenished with fresh medium. Differentiation was confirmed by flow cytometry analysis on day 7. $CD14^{low}$ $CD1a^{high}$ DC-$SIGN^{high}$ cells were used for experiments.

Quantitative real-time RT-PCR: Total RNA was isolated from cells using an RNeasy kit (Qiagen) according to the manufacturer's instructions. RNA was reverse transcribed using the SuperScript VILO cDNA synthesis kit (Invitrogen) according to the manufacturer's instructions. PCR primers were designed using Roche's Universal Probe Library Assay Design Center and purchased from Integrated DNA Technology. Quantitative RT-PCR was performed on a LightCycler 480 Probes Master (Roche.) All data are presented as a relative quantification with efficiency correction based on the relative expression of target gene versus GAPDH as the invariant control.

Fluidigm BioMark assay: The 5'-pppRNA BioMark experiment was performed with Mo-DCs derived from 3 independent healthy donors. Total RNA and cDNA were prepared as described above. cDNA along with the entire pool of primers were preamplified for 18 cycles using TaqMan PreAmp master mix as per the manufacturer's protocol (Applied Biosystems). Preamped cDNA was treated with Exonuclease I (New England BioLabs) and then combined with 2× FastStart TaqMan Probe MasterRoche), GE sample loading buffer (Fluidigm), and Taq polymerase (Invitrogen). Assays were prepared with 2 assay loading reagent (Fluidigm), primers (IDT), and probes (Roche). Samples and assays were loaded in their appropriate inlets on a 48.48 BioMark chip. The chip was run on the BioMark HD System (Fluidigm) for 40 cycles. Raw cycle threshold ($C_T$) values were calculated by the real-time PCR analysis software (Fluidigm), and software-designated failed reactions were discarded from analysis. All data are presented as relative quantifications with efficiency corrections based on the relative expression of target gene versus the geomean of (GAPDH+actin+β2-microglobulin) as the invariant control. The n-fold differential expression of mRNA gene samples was expressed as $2^{-\Delta\Delta C_T}$. The heatmaps were produced with the pheatmap Pretty Heatmaps package and R package version 0.7.7 (http://CRAN.R-project.org/package_pheatmap). Gene level expression is shown as $2^{-\Delta\Delta C_T}$ or genewise standardized expression (Z score). The sequences of forward (F) and reverse (R) primers used are SEQ ID NOs: 45-111.

Immunoblot analyses: Whole-cell extracts were separated in 4 to 20% acrylamide Mini-Protean TGX precast gels (Bio-Rad) by SDS-PAGE and transferred to an Immobilon-PSQ polyvinylidene difluoride (PVDF) membrane (Millipore) for 1 h at 100 V in a buffer containing 30 mM Tris, 200 mM glycine, and 20% methanol. Membranes were blocked for 1 h at room temperature in blocking buffer (Odyssey) and then probed with the following primary antibodies: anti-RIG-I (EMD Millipore), anti-IFIT1 (Thermo Fisher Scientific), anti-ISG56 (Cell Signaling), anti-STAT1 (Cell Signaling), anti-pIRF3 S396 (Cell Signaling), anti-IRF3 (Cell Signaling), anti-TLR3 (Cell Signaling), anti-MDA5 (Cell Signaling), anti-β-actin (Odyssey), anti-dengue virus (DenV) 2E protein (Santa Cruz Biotechnology), and anti-NS1 (Santa Cruz Biotechnology). Antibody signals were detected by immunofluorescence using the IRDye 800CW and IRDye 680RD secondary antibodies (Odyssey) and the LI-COR imager (Odyssey).

Flow cytometry analysis: The percentage of dengue virus-infected cells was determined by standard intracellular staining (ICS) using a mouse IgG2a monoclonal antibody (MAb) specific for dengue virus E protein (clone 4G2) followed by staining with a secondary anti-mouse antibody coupled to phycoerythrin (PE) (BioLegend). pSTAT1 geomean fluorescence was determined by PhosFlow staining as previously reported (Olagnier D et al, PLoS Pathog 10: e1004566 (2014); incorporated by reference herein) with pSTAT1 Y701 Pacific Blue antibody (BD Biosciences). Cells were analyzed on an LSRII flow cytometer (Becton Dickinson).

Calculations and population analyses were done using FACSDiva software.

Virus production and in vitro infection: Dengue serotype 2 strain New Guinea C (NGC) was used to infect confluent monolayers of C6/36 insect cells at a multiplicity of infection (MOI) of 0.5. Virus was allowed to adsorb for 1 h at 28° C. in serum-free Dulbecco's modified Eagle medium (DMEM). Serum-free DMEM was used to wash the monolayer and then replaced with DMEM-2% FBS. After 7 days of infection, the medium was harvested and cleared by centrifugation (1,100×g for 10 min), and the supernatant was concentrated by centrifugation (1,100 g) through a 15-ml Amicon centrifugal filter unit (Millipore). The virus was concentrated by ultracentrifugation on a sucrose density gradient (20% sucrose cushion) using a SorvallWX100 Ultracentrifuge (ThermoScientific) for 2 hours at 134,000 g and 10° C. with the brake turned off. Concentrated virus was then washed to remove sucrose using a 15-ml Amicon tube. After 2 washes, the virus was resuspended in DMEM-0.1% bovine serum albumin (BSA). Titers of dengue stocks were determined by fluorescence activated cell sorting (FACS) after infection of Vero cells and immunofluorescence staining of intracellular dengue E protein 24 h postinfection. For dengue virus challenge experiments, A549 cells and Mo-DCs were infected using dengue virus at an MOI of 0.5 in serum-free medium for 1 h at 37° C. Medium was replaced with complete medium for 24 h prior to analysis.

For in vitro influenza virus challenge experiments, A549 cells and Mo-DCs were infected with various influenza virus strains (MOI of 0.2 or 2) in a small volume of serum-free medium for 1 h at 37° C. Medium was replaced with complete medium for 24 h prior to analysis.

Reassortant H5N1 influenza virus (H5N1-PR8) was generated using hemagglutinin (HA) and neuraminidase (NA) genes derived from the H5N1 virus [HA from influenza A/Vietnam/1203/2004 and NA from influenza A/Thailand/1(KAN-1)/2004]. The internal viral proteins were derived from the A/Puerto Rico/8/1934 (PR8) mouse-adapted influenza A virus. The H5N1-PR8 reassortant viruses were propagated using MDCK cells. All procedures with live dengue and influenza viruses were performed in a biosafety level 2 facility at the Vaccine & Gene Therapy Institute of Florida.

Plaque assay: The plaque assay was performed on supernatants from influenza-infected A549 cells. MDCK cells in 6-well plates were grown to confluence and washed twice with DMEM containing 1% penicillin streptomycin (Life Technologies). Serial dilutions of virus (1:10) were inoculated on MDCK cells in a volume of 100 μl and adsorbed for 1 h at room temperature, with rocking every 15 min. Wells were washed twice with DMEM containing antibiotics. Leibovitz's L-15 medium (2, with L-glutamine) (Cambrex) was prepared with HEPES, 7.5% sodium bicarbonate, gentamicin, and TPCK (tosylsulfonyl phenylalanyl chloromethyl ketone)-trypsin (0.6 mg/ml) (Sigma-Aldrich), combined with 1.6% agarose, and overlaid on infected cells. Plates were incubated at 37° C. and monitored daily for plaques. At 48 h postinfection, plaques were stained with 1% crystal violet-20% ethanol and counted, and viral titers were calculated.

In vivo administration of 5'-pppRNA and viral infection: BALB/c mice (6 to 8 weeks of age; Jackson Laboratories) were housed in cage units, fed ad libitum, and cared for under USDA guidelines for laboratory animals. Prior to 5'-pppRNA injections and viral challenge, mice were anesthetized with IsoSol (Patterson Veterinary), and 5 μg of purified 5'-pppRNA was injected intravenously via a tail vein. The 5'-pppRNA was complexed with in vivo-jetPEI (PolyPlus, France) at an N/P ratio of 8 according to the manufacturer's instructions. Mice were then challenged with H5N1-RE (5,000 PFU in 50 μl of phosphate-buffered saline [PBS]). Animals were monitored for survival and morbidity (weight loss, ruffling fur, hunched back, and lethargy) each day during the viral challenge. Lungs were isolated from mice postmortem and snap-frozen in dry ice/ethanol bath. DMEM (10 volumes to grams) of was then added to the tissue placed in a 0.7-μm cell strainer in a petri dish, and the sample was muddled until it had been broken down. The remaining liquid was collected from the petri dish in a sample tube for stock lung homogenate sampling. All procedures with reassortant influenza virus H5N1-PR8 were performed in a biosafety level 2 facility at the Vaccine & Gene Therapy Institute of Florida.

Control RNA and M8 5'-pppRNA were administered to adult mice using a protocol similar to that of the influenza virus infection in vivo model. Mice were injected intraperitoneally with 2 μg RNA in combination with in vivo JetPEI for 24 h and then infected with 1,000 PFU chikungunya virus via footpad injection in 20 μl RPMI. Treatments were assessed via caliper for footpad swelling or viral titer of blood as determined by plaque assays on confluent monolayers of Vero cells as previously reported (Pal et al, 2014 supra). All procedures with chikungunya virus were performed at Oregon Health and Science University.

Statistical analyses: Values were expressed as the means±standard errors of the means, and statistical analysis was performed using Prism software (GraphPad software) or Microsoft Excel using an unpaired, two tailed Student's t test to determine significance. Differences were considered significant at a P value of <0.05.

Example 4

Enhanced Influenza VLP Vaccination with a Structurally Optimized RIG-I Agonist as Adjuvant The molecular interaction between viral RNA and the cytosolic sensor RIG-I represents the initial trigger in the development of an effective immune response against infection with RNA viruses, resulting in the activation of innate antiviral factors and subsequent induction of adaptive responses. In the present study, the adjuvant properties of a sequence-optimized 5'pppRNA RIG-I agonist (termed M8 herein) were examined in combination with influenza virus-like particles (VLP) as immunogens. A formulation comprising both VLP and M8 resulted in a higher antibody response than that of VLP alone. Furthermore, this formulation protected mice against lethal reassortant H5N1 influenza challenge more readily than controls. M8-VLP immunization also resulted in long term protective responses against influenza infection in mice. M8-VLP immunization also increased endpoint and antibody titers and inhibited influenza replication in lungs, when compared with other adjuvants such as Alum, AddaVax, and poly(I:C).

Immunization with M8-VLP stimulated a $T_H1$-biased CD4 T cell response, as determined by higher $T_H1$ cytokine levels in CD4 T cells and increased IgG2 levels in sera than controls lacking M8. Collectively, these data demonstrate that RIG-I agonists are potent adjuvants. The development of novel adjuvants to increase vaccine immunogenicity is an important goal that seeks to improve vaccine efficacy and thus prevent infections that endanger human health and safety. This example demonstrates the adjuvant properties of a RIG-I agonist using influenza virus-like particles (VLP) as antigens.

Annual vaccination with the trivalent inactivated influenza vaccine (TIV), quadrivalent inactivated influenza vaccine (QIV), or the live attenuated influenza vaccine (LAIV) are the primary strategies for reducing the morbidity and mortality associated with human influenza infection (Hannoun C, *Exp Rev Vaccines* 12, 1085-1094 (2013 and McKeage K, *Drugs* 73, 1587-1594 (2013); both of which are incorporated by reference herein). The protection provided by the TIV vaccine is strong in young adults, but its efficacy decreases in the elderly due to immunosenescence, which is characterized by decreases in effector cell number and function, as well as alterations in production of inflammatory and antiviral cytokines (Metcalf T U et al, *Aging Cell* 14, 421-432 (2015); Baldwin S L et al, *J Immunol* 188, 2189-2197 (2012); and Atmar R L and Keitel W A, *Curr Top Microbiol Immunol* 333, 323-344 (2009); all of which are incorporated by reference herein). Additionally, individual immune responses vary dramatically because of multiple factors, including the immunogen, route of administration, age of the subject, and virus type. Thus, an additional immune stimulation is frequently necessary to enhance vaccine efficacy. With increasing emphasis on subunit and/or peptide-based immunization and the ultimate need to develop a universal influenza vaccine, new approaches to improve vaccine efficacy are warranted (McLean H Q et al, *J Infect Dis doi:*10.1093/infdis/jiu647 (2014); incorporated by reference herein).

Virus-like particles (VLP) are an attractive alternative to more traditional live-attenuated or split vaccines. VLP mimic the virus in structure and morphology, but are non-infectious, and thus possess a high safety profile that enhances their potential for future vaccine development against highly pathogenic strains (Schneider-Ohrum K and Ross T M, *Curr Top Microbiol Immunol* 354, 53-73 (2012); incorporated by reference herein). As with live, attenuated virus vaccination, VLP stimulate the immune system, leading to both humoral and cellular immune responses. An effective VLP-based vaccine typically includes a strong immunogen (e.g. a viral surface glycoprotein such as hemagglutinin) and a potent adjuvant for inducing antiviral signals (Alving C R et al, *Curr Opin Immunol* 24, 310-315 (2012) and Osterholm M T et al, *Lancet Infect Dis* 12, 36-44 (2012); both of which are incorporated by reference herein). Importantly, VLP can be genetically engineered to express vaccine antigens that represent a population of sequences and elicit cross-protective immune responses against multiple pathogens (Giles B M and Ross T M, *Exp Rev Vaccines* 11, 267-269 (2012); incorporated by reference herein). Influenza VLP can be formed following co-expression of just three viral proteins—matrix, haemagglutinin (HA), and neuraminidase (NA)—in a mammalian expression system; VLP express the major surface influenza proteins in the same conformation as found in the influenza virion and have been shown to stimulate a potent immune response (Schneider-Ohrum and Ross, 2012 supra).

Addition of an adjuvant is a key strategy that: 1) enhances immunogenicity of the antigen; 2) permits a reduction in the amount of viral epitope per vaccine (termed "antigen sparing"); and 3) stimulates immune responsiveness in the elderly, thus increasing vaccine efficacy in this population (Leroux-Roels I et al, *Lancet* 370, 580-589 (2007); incorporated by reference herein). The most commonly used FDA-approved adjuvant is aluminum salts (Alum) although it is not included in any of the current influenza formulations in the US. In addition to Alum, vaccines can be formulated with adjuvants such as MF59, AF03 and AS03, vaccine antigen delivery vehicles, virosomes, (Schwendener R A, *Ther Adv Vaccines* 2, 159-182 (2014); incorporated by reference herein), and the adjuvant combination AS04 (Lee Y N et al, *Vaccine* 32, 4578-4585 (2014); incorporated by reference herein) All of these adjuvants act by creating an antigen depot, activating antigen-presenting cells, and triggering an innate immune response by stimulation of danger signals (Reed S G et al, *Nat Med* 19, 1597-1608 (2013); incorporated by reference herein). Given the wide range of vaccine strategies currently under study, a high priority for the development of influenza vaccines is the identification of novel adjuvants that elicit a broad and robust immune response to increase immunogenicity of antigens and to enhance the antigen sparing effect (Reed, 2013 supra, Coffman R L et al, *Immunity* 33, 492-503 (2010); and Jiang F et al, *Nature* 479, 423-427 (2011); both of which are incorporated by reference herein).

Influenza infection is sensed by RIG-I, a cytosolic sensor that detects viral RNA during replication through its helicase domain (Jiang F et al, *Nature* 479, 423-427 (2011); incorporated by reference herein). RIG-I also possesses an effector caspase activation and recruitment domain (CARD) that forms a complex with the mitochondrial adaptor MAVS (Komuro A et al, *Cytokine* 43, 350-358 (2008); incorporated by reference herein). MAVS serves as a signaling platform for protein complexes that activates transcription factors NF-κB, IRF3 and IRF7 Belgnaoui S M et al, *Curr Opin Immunol* 23, 564-572 (2011) and Loo Y M and Gale Jr. M, *Immunity* 34, 680-692 (2011); both of which are incorporated by reference herein) that induce the expression and production of type I interferon (IFN), as well as pro-inflammatory cytokines and antiviral proteins (Takeuchi O and Akira S, *Cell* 140, 805-820 (2010); incorporated by reference herein). A secondary response involving hundreds of IFN stimulated genes (ISGs) is induced by secreted IFN binding to the type I IFN receptors on adjacent cells and tissues, leading to amplification of the antiviral immune response via the JAK-STAT pathway (Schoggins J W et al, *Nature* 472, 481-485 (2011); incorporated by reference herein). This stimulation of the innate antiviral response also contributes to the maturation of dendritic cells and clonal expansion of CD4+ and CD8+ T-cells (Longhi M P et al, *J Exp Med* 206, 1589-1602 (2009); incorporated by reference herein), all of which contribute to the establishment of long-term adaptive immunity against infection. The use of natural or synthetic 5'-triphosphate-containing RNA (5'pp-pRNA) that activate innate immunity via RIG-I could therefore be an attractive strategy for the development of broad-spectrum antivirals and vaccine adjuvants.

It has been previously demonstrated that intravenous injection of a short, double-stranded RNA containing a 5'triphosphate (5'ppp) moiety, derived from the 5' and 3'-un-translated regions of the vesicular stomatitis virus VSV genome (WT 5'pppRNA) stimulated innate responses in lungs and protected mice from lethal H1N1 influenza challenge (Goulet M L et al, *PLoS Pathol* 9, e1003298 (2013); incorporated by reference herein). Transcriptional profiles of lung epithelial cells treated in vitro with the oligoribonucleotide termed WT 5'pppRNA herein identified overlapping and unique transcriptional signatures associated with genes capable of mobilizing multiple arms of innate and adaptive responses. Specific modifications in the structure of the oligoribonucleotide—modifications to the primary RNA sequence that eliminated mismatch in the double stranded RNA region—removed the panhandle structure and introduced additional bases—resulted in a 59-nucleotide double-stranded RNA structure (M5) with improved antiviral properties compared to WT 5'pppRNA. Further improvement of M5 antiviral properties was achieved by the addition of AU base pairs to increase the length of the dsRNA stem structure. The resulting sequence-optimized agonist, M8, further increased breath and magnitude of the antiviral and inflammatory response observed in primary human dendritic cells compared to WT 5'pppRNA or M5. As an antiviral agent, M8 efficiently inhibited influenza and dengue virus replication in vitro and decreased both chikungunya and influenza virus replication in vivo.

Because of its capacity to stimulate a potent antiviral and inflammatory response, we hypothesized that M8 may also function as an adjuvant in a VLP-based influenza vaccine formulation. In the present study, we demonstrate that M8-VLP increased antibody levels, protected against lethal influenza H5N1 challenge, stimulated formation of germinal center B cells, and induced a $T_H1$-predominant cellular immune phenotype upon vaccination. These results illustrate that agonist-specific stimulation of the RIG-I pathway can be used as an adjuvant in influenza VLP vaccination and dramatically improve humoral and cellular mediated protective responses against influenza challenge.

In vitro synthesis of 5'pppRNA. RIG-I agonists were synthesized using in vitro RNA transcription kit (Ambion) as previously described (Goulet et al, 2013 supra). RNA transcripts were digested with DNase for 15 minutes at 37° C. then purified using miRNeasy kit (Qiagen). Integrity of the purified 5'pppRNA was analyzed on a denaturing 15% TBE-urea polyacrylamide gel (Bio-Rad) and compared to the 5'pppRNA digested with RNase A or DNase (Ambion).

Isolation and transfection of monocyte-derived dendritic cells (MDDC). Human peripheral blood mononuclear cells (PBMC) were isolated from buffy coats of healthy volunteers. PBMC were isolated using the Ficoll-Paque™ PLUS medium (GE Healthcare Bio). CD14+ monocytes were isolated by positive selection using CD14 microbeads (Miltenyi Biotech) and a magnetic cells separator. Purified CD14+ monocytes were cultured for 7 days in in 10 mL of complete monocyte differentiation medium (Miltenyi Biotech). On day 3, the medium was replenished with fresh medium. Only cells with the $CD14^{lo}CD1a^{hi}DC$-$SIGN^{hi}$ phenotype after 5-7 days differentiation were used in subsequent experiments. MDDCs were transfected with various amounts of WT, M5, or M8 5'pppRNA or poly (I:C) for 24 h using HiPerfect Transfection Reagent (Qiagen) for 24 h. MDDCs were stained for 5 minutes with human TruStain FcX (Biolegend) followed by staining with CD83-PE (Biolegend), CD86-Pacific Blue (Biolegend), CD80-PE, or CD40-PE, for 15 minutes at 4° C. Cells were analyzed on an LSRII flow cytometer (Becton Dickinson). Calculations and population analyses were done using FACS Diva software.

Quantitative real-time RT-PCR. Total RNA was isolated from cells using RNeasy kit (Qiagen) and RNA was reverse transcribed using the SuperScript® VILO cDNA synthesis kit (Invitrogen). PCR primers were designed using Roche's Universal Probe Library Assay Design Center (www.universalprobelibrary.com). Quantitative RT-PCR was performed on a LightCycler® 480 Probes Master (Roche.) All data are presented as a relative quantification with efficiency correction based on the relative expression of target gene versus GAPDH as the invariant control. The sequences of forward and reverse primers used are listed as SEQ ID NOs: 112-127 above.

Virus propagation and challenge: Influenza reassortant mouse adapted H5N1 virus (H5N1) expressing H5 haemagglutinin (HA) A/Vietnam/1203/2004 and neuraminidase (NA) A/Thailand/1(KAN-1)/2004 and internal viral genes from mouse adapted A/Puerto Rico/8/1934 (PR8), was propagated using MDCK cells as previously described (Bright R A et al, PLoS One 3, e1501 (2008); incorporated by reference herein). In animal challenge experiments, anesthetized female BALB/c mice were infected intranasally with the lethal dose ($5 \times 10^3$ PFU in 50 µL PBS) of the H5N1. This dose represents approximately 50 $LD_{50}$ doses in mice.

Virus like particle vaccine: H5N1 virus like particles were purified from HEK293T cells which were transfected using Lipofectamine2000 (Invitrogen) with 5 µg of each plasmid DNA expressing H5N1 A/Vietnam/1203/2004 HA and H5N1 A/Thailand/1(KAN-1)/2004 NA (codon optimized); and 10 µg of plasmid DNA expressing HIV gag. Cells were incubated for 72 h at 37° C. and supernatants containing VLP were collected, sterile filtered, and purified by centrifugation at 100,000×g through a 20% glycerol cushion and resuspended in PBS. Total protein was quantified using BCA protein assay (Thermo Fisher Scientific) and VLP were aliquoted in PBS and stored at −80° C. HA content was quantified by densitometry as described previously (Giles B M and Ross T M, Vaccine 29, 3043-3054 (2011); incorporated by reference herein).

Immunization: BALB/c mice (6-8 weeks of age, Jackson Laboratories) were housed in cage units, fed ad libitum, and cared for under USDA guidelines for laboratory animals. For immunization, mice were anesthetized with IsoSol (Patterson Veterinary) and immunized via the intramuscular route (IM) with 0.5 µg-2 µg (based on HA content) of purified VLP (in 50 µl PBS) with or without 0.1 µg-5 µg 5'pppRNA as adjuvant and then challenged at week 3. The 5'pppRNA was delivered with in vivo-jetPEI (PolyPlus, France) at an N/P ratio of 8 according to the manufacturer instructions. Imject Alum (Fishersci, Pittsburgh, Pa.) and AddaVax (Invivogen, San Diego, Calif.) were added to 50% volume of VLP in PBS solution per manufacturer's recommendation. Animals were monitored for survival and morbidity weekly during the immunization regimen and each day during the viral challenge. Blood samples for serological analysis were collected from anesthetized mice via retro-orbital sinus. Blood was allowed to clot at room temperature and sera was removed and frozen at −80° C. after centrifugation.

Sickness score. After infection, mice were monitored daily for weight loss, disease signs and death for up to 21 days after infection. Individual body weights, sickness scores and death were recorded for each mouse after inoculation. The sickness score was generated by evaluating activity (0=normal, 1=reduced, 2=severely reduced), hunched back (0=absent, 1=present) and ruffled fur (0=absent, 1=present) as described previously (27). The final score was the addition of each individual score resulting in the minimum score 0 for a healthy mouse and 1-4 for a sick mouse.

Virus plaque assay. Lungs were isolated from mice postmortem and snap frozen in dry ice/ethanol bath. Dulbecco's modified Eagle medium (DMEM, 10 volumes to grams) of was then added to the tissue placed in a 0.7 µm cell strainer in a petri dish and sample was muddled until tissue was fully disaggregated. Remaining liquid was collected from petri dish in sample tube for stock lung homogenate sample. Confluent MDCK cells plated in 6-well tissue culture plates were inoculated with 0.2 ml of virus or lung cell supernatant serially diluted (1:10) in DMEM. Virus was adsorbed for 1 h, with shaking every 15 min. Wells were overlaid with 1.6% (w/v) Bacto agar (BD Diagnostic Systems) mixed 1:1 with L-15 media (Cambrex) containing 1% Pen Strep (Life Technologies), with 0.6 mg/ml TPCK-Trypsin (SigmaAldrich). Plates were incubated for 2 days at 37° C. and plaques were visualized with crystal violet.

Hemagglutination inhibition activity. The hemagglutination inhibition (HAI) assay was used to assess functional antibodies to the HA able to inhibit agglutination of horse red blood cells. The procedure was adapted from the Center for Disease Control influenza surveillance manual and performed as previously described (Bright et al 2008 supra).

Serological assays. ELISA plates (BD biosciences) were coated with 25 ng per well of purified recombinant hemagglutinin encoded by A/Vietnam/1203/2004 in carbonate buffer pH 9.4 containing 5 µg/mL BSA Fraction V at 4° C. overnight. Plates were then blocked with ELISA blocking buffer (PBS containing 5% BSA Fraction V, 2% bovine gelatin and 0.05% Tween 20) for >90 min at 37° C. Serial dilutions of immune sera were incubated for >90 min and plates washed five times with PBS. Total HA-specific IgG was detected using horseradish peroxidase conjugated Goat anti-mouse IgG (γ-chain specific) (Southern Biotech, Birmingham, Ala.) diluted to 1:2500 in ELISA blocking buffer. Following additional PBS washes, 2,2'-azino-bis(3-ethylbenzothiazoline-6-sulphonic acid) (ABTS) substrate was added and plates incubated 10-20 min at 37° C. Colorimetric conversion was measured as the optical density (O.D. at 414 nm) by a spectrophotometer (BioTek, Winooski, Vt., USA). O.D. values from BSA only coated wells were subtracted to determine HA-specific reactivity. HA-specific IgG subclasses were measured in sera samples diluted to 1:50 in ELISA blocking buffer and detected using horseradish peroxidase conjugated goat anti-mouse IgG1, IgG2a IgG2b, and IgG3 antibodies (Southern Biotech, Birmingham, Ala.) diluted to 1:1000 in blocking buffer.

Assessment of T and B cell responses: Spleens from mice immunized intraperitoneally 8 days prior with 1 µg VLP (based on HA content) were harvested in cold RPMI. Spleens were mechanical dissociated through 70 µm cell strainers and the resulting single-cell suspension washed in cold RPMI. The cell suspensions were then incubated with ACK buffer to lyse RBC and counted following a washing step. For assessment of B cell responses, $2-5\times10^6$ splenocytes were stained directly ex vivo. For assessment of T cell responses, $5\times10^6$ splenocytes were cultured in RPMI containing vehicle, VLP (1 µg/mL) or the HA-derived peptide (IYSTVASSL) (10 µg/mL) for 21 h. Brefeldin A (Ebioscience) was added 6 hr prior to harvest. The following monoclonal antibodies were used: FITC anti-mouse TNF-α (MP6-XT22) PE anti-mouse Il-2 (clone JES6-5H4), PE-Cy7 anti-mouse IFN-γ (clone XMG1.2), Pacific Blue anti-mouse CD8a (clone 53-6.7), APC anti-mouse CD4 (clone GK1.5), PE-Dazzle594 anti-mouse B220 (clone RA3-6B2), Pacific Blue anti-mouse CD44 (clone IM7), PerCP anti-mouse CD19 (clone eBio1D3), FITC anti-mouse CD38 (clone 90), and Alexa Fluor647 anti-mouse IgG1 (clone RMG1-1, 1:500) (all from BioLegend). Additional antibodies were biotin anti-mouse CD95 (clone Jo1) and PE anti-CD138 (clone 281-2) (both from BD biosciences). Both LIVE/DEAD fixable dead cell stain (Invitrogen) and intracellular staining using BD Cytofix/Cytoperm™ Kit were performed according to the manufacturers' instructions.

Histology. Lungs were harvested and prepared for immunohistochemistry using a modified protocol (Olagnier D and Hiscott J, *Hepatology* 59, 1225-1228 (2014); incorporated by reference herein). After euthanasia, the chest cavity was opened and the lungs were gently inflated intratracheally with 4° C. 4% paraformaldehyde in PBS, removed and immersed in 4% paraformaldehyde at 4° C. overnight. The next day, the solution was replaced with 70% ethanol and tissues were kept at 4° C. for up to 2 weeks. Tissue sections were embedded in paraffin, sectioned into slices (~5 µm in thickness), and stained with hematoxylin and eosin (H&E) or left unstained. Tissue sections were imaged with a Qimaging Micropublisher 5.0 RTV digital camera on an Olympus BX61 fluorescence microscope. To quantify the number of apoptotic lung cells, representative sections were deparaffinized and rehydrated in xylene and graded alcohols, respectively, using standard procedures, and TUNEL assay was performed according to manufacturer's instructions (Roche, Mannheim, Germany). The percentages of TUNEL-positive cells within the tissue sections were determined by counting at least 100 cells each from eight randomly selected fields.

Statistical analyses: Values are expressed as mean±SEM, and statistical analysis was performed using PRISM software (GraphPad software) using one-way ANOVA followed by Tukey post-hoc test to determine significance.

M8 Potentiates DC Maturation and Anti-Viral Signaling in Human MDDC. The most efficient antigen-presenting cells are mature, immunologically competent dendritic cells (DC) (Schraml B U and Reis E S C, Curr Opin Immunol 32C, 13-20 (2014); incorporated by reference herein) and it is now accepted that the adjuvant component of vaccines contributes to vaccine efficacy by triggering DC maturation and antigen presentation (Palucka K and Banchereau J, Nat Rev Cancer 12, 265-277 (2012); incorporated by reference herein. To determine whether selected 5'pppRNA sequences differ in their ability to induce DC maturation ex vivo, the mRNA expression of selected genes involved in DC maturation and activation was assessed. Chemokine CCL4, activation and/or co-stimulation markers CD40, CD80, CD83 and CD86, 4-1BB, HLA-DRA, HLA-DQA, and CD74 expression were all upregulated by treatment of primary DC cultures with M8 (FIG. 23A). These data were confirmed by measuring the protein expression of several DC activation/maturation markers in MDDC treated with WT 5'pppRNA, M5, M8, and poly(I:C) (FIG. 23A) (Yu M and Levine S J, Cytokine Growth Factor Rev 22, 63-72 (2011); incorporated by reference herein). M8 treatment resulted in a ~5-fold increase in the protein expression of CD40, and CD86, a ~3-fold increase in the expression of CD83, and a ~2-fold increase in expression of CD80, compared to cells treated with WT, M5 or poly(I:C). Collectively, these data indicated that M8 was a potent inducer of DC maturation and activation.

M8 potentiates influenza VLP immunogenicity. To determine if M8 possessed adjuvant activity in an in vivo model of vaccination, BALB/c mice were vaccinated by intramuscular injection with VLP co-expressing the HA and NA from H5N1 and HIV GAG protein, in combination with M8, M5 or poly(I:C) (which was previously shown to potentiate responses to influenza antigens (Goff P H et al, PLoS One 8, e79194 (2013); incorporated by reference herein). Three weeks later, mouse sera were collected and analyzed for HAI activity [hemagglutination inhibition assay (HAI) or receptor blocking titers]; mice immunized with VLP combined with M8, M5 or poly(I:C) displayed 2-3-fold greater HA-specific IgG titers and 2-3 fold higher HAI antibody titers ($p<0.005$) (FIG. 24A) compared to mice immunized with VLP alone. M8 was a more potent stimulator of HA-specific IgG and HAI antibody titers compared to M5 or poly(I:C) (FIG. 24A).

Next, vaccinated mice were challenged with a lethal dose of influenza H5N1, and lungs were harvested for assessment of influenza replication and histopathological analysis three days post-infection (FIG. 24B). Immunization with VLP alone resulted in a 4-log decrease in viral plaques, while adjuvantation of VLP with M8, M5 or poly (I:C) resulted in an additional f-log reduction in viral titer (p<0.05). When compared to M5-VLP or poly(I:C)-VLP, mice immunized with M8-VLP had the lowest virus titer in the lungs. These data were further corroborated by histopathological examination and assessment of lung tissue apoptosis. TUNEL staining revealed that the number of apoptotic cells was approximately 3-fold lower in VLP-immunized mice compared to control, and a further 5-10 fold lower when M8, M5 or poly (I:C) were used as an adjuvant (p<0.05, FIG. 24C). Mice immunized with M8-VLP had ~50% fewer apoptotic cells compared to M5-VLP or poly(I:C)-VLP immunized mice. Similarly, H&E staining of lung cross-sections indicated complete absence of edema and inflammation in mice immunized with VLP-adjuvanted with M8, while non-vaccinated, adjuvant-only vaccinated, and to a lesser extent VLP-vaccinated mice, had signs of inflammation around airways (FIG. 24D). Altogether, these data indicate that VLP combined with M8, M5 or poly(I:C) efficiently blocked influenza virus replication, decreased virus-induced apoptosis, and decreased inflammation in the lungs of vaccinated animals. Of the adjuvants tested, M8-VLP elicited the highest level of HAI antibody titers and demonstrated the lowest level of influenza-induced lung tissue damage, highlighting the improved design and activity of M8.

Antigen sparing capacity of M8 in Combination with VLP. Antigen sparing is regarded as a crucial parameter for pandemic vaccine development. Because the addition of adjuvant to a vaccine is an important antigen-sparing strategy (Dormitzer P R et al, *Immunol Rev* 239, 167-177 (2011); incorporated by reference herein), the capacity of M8 to stimulate immune responses to decreasing doses of VLP was determined. Mice were immunized with 0.5, 1 or 2 µg VLP (as measured by HA content) alone or in combination with M8 (5 µg). Analysis of the HAI antibody titers three weeks showed that 0.5 µg VLP+5 µg M8 resulted in a similar titer to 2 µg VLP (FIG. 25A). Next, mice were challenged with a lethal inoculum of influenza H5N1 (5,000 pfu/mouse). Similar to the results seen with HAI antibody titers, lung virus titers measured three days post-challenge were comparable between immunized with VLP alone (2 µg) or VLP (0.5 µg) formulated with M8 (FIG. 25B). To determine the minimal dose of M8 that was able to elicit a protective immune response, BALB/c mice were immunized with a single low dose inoculum of VLP (0.5 µg), and with varying concentrations of M8 (0.1-5 µg). Three weeks post-immunization, sera were collected to determine antibody titers and mice were challenged with H5N1. Three days after the challenge, lungs were collected to determine virus titers. Addition of as little as 0.5 µg M8 resulted in 1.5-fold higher HAI antibody titers compared to VLP alone (FIG. 25C) and greater antibody titers were observed in a dose-dependent manner with still higher concentrations of M8. A reciprocal relationship was observed with lung virus titers—higher concentrations of M8 resulted in lower lung viral loads. The effect was maximal in mice immunized with 5 µg M8-VLP (FIG. 25D). Finally, mice immunized with 0.5-5 µg M8 in combination with VLP all survived the H5N1 challenge, although limited weight loss was observed at lower M8 concentrations (FIGS. 25E,25F), indicating that M8 (0.5 µg or higher) functioned as an antigen-sparing adjuvant in protecting BALB/c mice from a lethal influenza challenge.

Adjuvant properties of M8, alum, addavax and poly(I:C). The adjuvant activity of M8 was next assessed relative to the FDA-approved adjuvant Alum, AddaVax—an MF59-like adjuvant (Mbow M L et al, Curr Opin Immunol 22, 411-416 (2010); incorporated by reference herein), and to poly(I:C)—by examining antibody titers, influenza lung titers, sickness score, weight loss and survival (illustrated schematically in FIG. 26A). Assessment of HA-specific IgG by ELISA revealed ~2-fold higher antibody levels in mice immunized with M8-VLP compared to mice immunized with Alum-VLP, AddaVax-VLP or poly(I:C)-VLP (FIG. 26B). Similarly, the HAI assay revealed a ~1.5-fold higher HAI antibody titer in M8-VLP vaccinated mice (FIG. 26C), compared to Alum-VLP, AddaVax-VLP, or poly(I:C)-VLP. Furthermore, levels of HA-specific IgM were also higher in M8-VLP immunized animals at five days after vaccination (FIG. 26D).

All animals immunized with an adjuvant+VLP formulation survived lethal influenza H5N1 challenge (FIG. 27A). Furthermore, animals immunized with VLP in combination with one of the four adjuvants showed no signs (M8-VLP) or temporary slight weight loss after challenge ([LP-Alum, VLP-AddaVax, and VLP-poly(I:C)] (FIG. 27B). In contrast, median survival for non-immunized animals or animals immunized with adjuvant-only was 9-10.5 days. Animals immunized with VLP had a median survival of 12 days (three animals survived influenza challenge). Post-immunization, the control VLP-immunized and adjuvant-immunized animals all lost weight (FIG. 5B). The health of the animals, as determined by the sickness score, was better in animals immunized with M8-VLP, even when compared to the animals immunized with Alum-VLP, AddaVax-VLP or poly(I:C)-VLP (FIG. 27C). M8-VLP treatment resulted in a ~1 log-fold lower viral titers three days post-infection compared to mice immunized with Alum-VLP, AddaVax-VLP, or poly(I:C)-VLP (FIG. 27D). Overall, use of M8 as an adjuvant in a formulation with VLP protected mice completely from a lethal influenza challenge and performed better than Alum-VLP, AddaVax-VLP, or poly(I:C)-VLP.

Figure 28E:
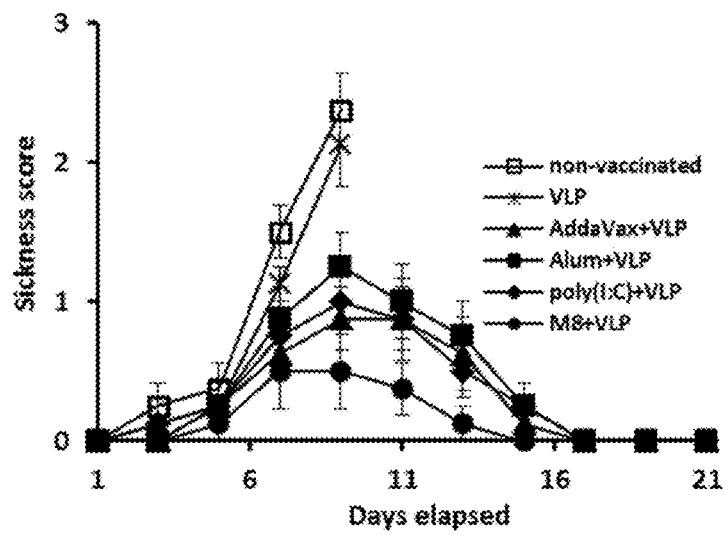

M8 stimulates prolonged immune responses. VLP vaccine adjuvanted with M8, Alum, AddaVax or poly(I:C) were tested in order to determine which would best induce a prolonged memory response against influenza challenge. Sera were collected at four weeks and again at four months after immunization. After the second serum collection, mice were challenged with H5N1 and their weights, survival and sickness score were assessed (FIG. 28A-28E). At four months after immunization, all animals immunized with adjuvanted VLP had detectable antibody titers, although 5-10 fold lower endpoint titers and ~50% lower in HAI antibody titers were observed in all cases (FIGS. 28A and 28B). Mice immunized with VLP adjuvanted with M8, Alum, AddaVax, or poly(I:C) all survived challenge, with only a 10-15% weight loss (FIGS. 28C and 28D); animals also had comparable sickness scores during the weight loss period (FIG. 28E). In contrast, VLP-immunized mice without adjuvant had no detectable antibody titers and were not protected from the lethal challenge. Altogether, these data indicate that M8, similarly to Alum, AddaVax and poly(I:C), stimulated a prolonged immune response capable of protecting mice against homologous influenza challenge.

M8-VLP promotes germinal center formation. Next, the capacity of M8 and other adjuvants to drive germinal center (GC) formation when co-administered with VLP was determined. Initially mice were immunized IM but no changes were observed with regard to GC formation between different groups and controls. So mice were immunized by intraperitoneal inoculation with VLP (1 µg, based on HA content), formulated with M8 or poly(I:C) (5 µg), or mixed 1:1 with Alum or AddaVax. Splenocytes from immunized mice were harvested on day 8 and evaluated by flow cytometry ex vivo for the presence of B220$^{hi}$CD19$^{hi}$CD95$^{hi}$CD38$^{lo}$GC B cells (FIG. 29A). Compared to mice immunized with VLP alone, a 2.2-fold increase in the frequency of GC B cells was observed for M8 ($p<0.05$), 3.5-fold for Alum ($p<0.01$), 4.5-fold for AddaVax ($p<0.005$), and 1.5-fold for poly(I:C) (FIG. 29B). In addition, the number of IgG1$^+$ GC B cells was also determined by intracellular staining. As shown in the bottom panel, the number of IgG1+GC B cells was elevated in mice immunized with Alum-VLP ($p<0.005$) or AddaVax-VLP ($p<0.005$) compared to VLP alone (FIG. 29C), indicating that these two adjuvants induced a $T_H2$-biased response.

M8-VLP biases CD4+ T cell effector function. To establish whether M8 induces $T_H1$ or $T_H2$ responses, the levels of four IgG subclasses (IgG1, IgG2a, IgG2b, and IgG3) were determined after immunization using HA coated ELISA plates and respective IgG secondary antibodies. Immunization of mice with VLP in combination with either Alum or AddaVax induced higher levels of IgG1, while immunization with M8-VLP induced higher levels of IgG2 (FIG. 30A), indicating that M8 preferentially induced a $T_H1$-biased response, whereas Alum or AddaVax preferentially induce $T_H2$-biased response (Viscaino M L et al, J Transl Med 10, 4 (2012); incorporated by reference herein). To further examine whether M8 promoted $T_H1/Tc1$ cytokine secretion, splenocytes from immunized mice were incubated with either HA$_{518-526}$ (10 µg/mL, IYSTVASSL) peptide or VLP (1 µg/mL, based on HA content). B220$^{neg}$ cells were segregated based on surface CD4 and CD8 expression and intracellular staining for IFNγ, IL-2, and TNFα (FIGS. 30B-30E). In vitro re-stimulation of splenocytes with VLP stimulated secretion of IFNγ in CD8+ T cells (FIG. 30B) and induced the secretion of all three cytokines in CD4+ T cells (FIGS. 30C-30E). The highest induction of these three cytokines was observed in splenocytes originating from M8-VLP immunized animals, followed Alum-VLP, AddaVax-VLP and poly(I:C)-VLP ($p<0.05$ between M8-VLP vs. Alum-VLP and $p<0.005$ between M8-VLP vs. AddaVax-VLP for IL-2 and TNFα). These data indicate that M8-VLP promoted $T_H1$ priming of VLP-stimulated CD4 T cells compared to Alum-VLP, AddaVax-VLP and poly(I:C)-VLP. Additionally, low intracellular levels of the $T_H2$ cytokine IL-10 were observed in animals vaccinated with M8-VLP (FIG. 30F), indicating that M8 does not induce a $T_H2$ biased response. Re-stimulation of splenocytes from M8-VLP immunized mice with HA$_{518-526}$ (IYSTVASSL) peptide did not elicit cytokine production by CD8+ T cells, indicating that IP vaccination with M8-VLP did not promote cross-presentation (Joffre O P et al, Nat Rev Immunol 12, 557-569 (2012); incorporated by reference herein).

---

The invention claimed is:

1. A synthetic oligoribonucleotide at least 41 nucleotides in length that can form a hairpin structure comprising at least 17 base pairs, the synthetic oligonucleotide further comprising a triphosphate group at a 5' end of the oligoribonucleotide wherein the synthetic oligoribonucleotide comprises SEQ ID NO: 13.

2. The synthetic oligoribonucleotide of claim 1 incorporated into a pharmaceutically acceptable carrier.

3. A pharmaceutical composition comprising a synthetic oligoribonucleotide of claim 1, a pharmaceutically acceptable carrier, and a viral antigen.

4. The pharmaceutical composition of claim 3 wherein the viral antigen comprises an influenza virus like particle.

5. A method of treating a viral infection, the method comprising administering an effective amount of the pharmaceutical composition of claim 3 to a subject.

6. An antiviral composition comprising a synthetic oligoribonucleotide of claim 1.

7. A method of inducing an antiviral response against a viral infection comprising administering to a subject an effective amount of the antiviral composition of claim 6.

8. The method of claim 7, wherein the viral infection is caused by dengue virus, chikungunya virus, or influenza virus.

* * * * *